United States Patent
Kikuchi et al.

(10) Patent No.: US 6,498,251 B1
(45) Date of Patent: *Dec. 24, 2002

(54) TETRAHYDROBENZINDOLE DERIVATIVES

(75) Inventors: Chika Kikuchi, Kanagawa (JP);
Takashi Ando, Kanagawa (JP);
Kazuyuki Fuji, Kanagawa (JP);
Masayo Okuno, Kanagawa (JP); Eriko Morita, Kanagawa (JP); Masako Imai, Kanagawa (JP); Osamu Ushiroda, Kanagawa (JP); Masao Koyama, Kanagawa (JP); Toyokazu Hiranuma, Kanagawa (JP)

(73) Assignee: Meiji Seika Kaisha, Ltd., Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 09/582,416
(22) PCT Filed: Dec. 22, 1998
(86) PCT No.: PCT/JP98/05827
§ 371 (c)(1),
(2), (4) Date: Mar. 8, 2001
(87) PCT Pub. No.: WO99/33804
PCT Pub. Date: Aug. 7, 1999

(30) Foreign Application Priority Data

Dec. 25, 1997 (JP) .......................................... 9-358380
Dec. 25, 1997 (JP) .......................................... 9-358381
Mar. 31, 1998 (JP) .......................................... 10-085913
May 19, 1998 (JP) .......................................... 10-136872
Aug. 14, 1998 (JP) .......................................... 10-229709
Nov. 10, 1998 (JP) .......................................... 10-319336

(51) Int. Cl.$^7$ .................... C07D 209/90; C07D 401/06; C07D 403/06; A61K 31/47; A61K 31/495
(52) U.S. Cl. .................. 544/254.08; 544/373; 514/339; 514/307; 514/301; 514/292; 546/276.7; 546/148; 546/114; 546/85
(58) Field of Search .................... 544/373; 514/254.08, 514/339, 307, 301, 292; 546/276.7, 148, 114, 85

(56) References Cited

FOREIGN PATENT DOCUMENTS

EP         0 937 715 A1    8/1999
WO         WO 99/54303     10/1999

OTHER PUBLICATIONS

XP–000941428, Ottoni et al, "Efficient and Simple Methods for the Introduction of the Sulfonyl, Acyl and Alkyl Protecting Groups on the Nitrogen of Indole and its Derivatives", Tetrahedron (1998), 54, (46), p. 13915–13928.

XP–00094304, Ihara, et al. "Novel One Step Transformation of Carbamates into Amides", Heterocycles, vol. 33, No. 2, 1992, p. 851–858.

Preliminary Partial Search Report—European Patent Office.

Leysen, Jose E. et al., "Alniditan, a new 5–hydroxytryptamine agonist and migrane–abortive agent: ligand–binding properties of human 5–hydroxytryptamine, human 5–hydroxytryptamine and calf 5–hydroxytryptamine receptors investigated with [3H]5–hydroxytryptamine and [3H] alniditan", Mol. Pharmacol., 50 (6), (1996), p. 1567–80.

Carter, David et al., "Characterization of a postjunctional 5–HT receptor mediating relaxation of guinea–pig isolated ileum", Eur. J. Pharmacol., 280(3), (1995), p. 243–50.

Bonate, Peter L., "Serotonin Receptor Subtypes: Functional, Physiological, and Clinical Correlates", Clinical Neuropharmacology, vol. 14, No. 1, pp. 1–16 (1991).

Ward, R.P. et al., "Localization of Serotonin Subtype 6 Receptor Messenger RNA in the Rat Brain by IN SITU Hybridization Histochemistry", Neuroscience vol. 64, No. 4, 1995, pp. 1105–111.

Roth, Bryan L., et al, "Binding of Typical and Atypical Antipsychotic Agents to 5–Hydroxytryptamine–6 and 5–Hydroxytryptamine–7 Receptors", The Journal of Pharmacology and Experimental Therapeutics, vol. 268, No. 3, (1994), pp. 1403–1410.

Tollefson, Gary D. et al., "The Association of Buspirone and Its Metabolite 1–Pyrimidinylpiperazine in the Remission of Comorbid Anxiety With Depressive Features and Alcohol Dependency" vol. 27, No. 2, 1991, pp. 163–170.

Gaster, Laramie M. et al., "N–[(1–Butyl–4–piperidinyl)methyl]–3, 4–dihydro–2H–[1,3] oxazino [3,2–a] indole–10–carboxamide Hydrochloride: The First Potent and Selective 5–HT Receptor Antagonist Amide with Oral Activity", J. Med. Chm, 1995, 38, pp. 4760–4763.

Lovenberg, Timothy W. et al., "A Novel Adenylyl Cyclase–Activating Serotonin Receptor (5–HT7) Implicted in the Regulation of Mammalian Circadian Rhythms", Neuron, vol. 11, Sep. 1993, pp. 449–458.

*Primary Examiner*—Mukund J. Shah
*Assistant Examiner*—Hong Liu
(74) *Attorney, Agent, or Firm*—Sughrue Mion, PLLC

(57) ABSTRACT

Compounds containing tetrahydrobenzindole which bind to serotonin receptor and are useful in treatment or prevention of disease induced by abnormality of central peripheral serotonin controlling functions.

12 Claims, No Drawings

TETRAHYDROBENZINDOLE DERIVATIVES

TECHNICAL FIELD

This invention relates to a tetrahydrobenzindole derivative or an intermediate thereof. Since this tetrahydrobenzindole derivative has the ability to bind to serotonin receptors in the living body, it also relates to the treatment and prevention of various diseases which are induced by the abnormality of serotonin controlling functions.

BACKGROUND ART

In the present society, the environment which surrounds us is sharply changing, and adaptation for it is becoming more and more difficult. Thus, a part which is too much for adaptation for the social environment is accumulated in our bodies as stress and sometimes causes abnormality of not only body functions but also mental functions. Under such circumstances, importance of drug therapy has been increasing more and more, so that development of effective drugs has been put forward.

Since the indication about the action of serotonin (5-HT) in the central nervous system, classification and distribution of serotonin receptors have been revealed gradually. By the detailed analysis of serotonin receptors using molecular biological means in recent years, 5-HT$_1$ and its subtypes, 5-HT$_2$ and its subtypes, 5-HT$_3$, 5-HT$_4$, 5-HT$_6$, 5-HT$_7$ and the like have been specified and a total of 14 different serotonin receptors have been proposed [R. D. Ward et al., *Neuroscience*, 64, 1105–1111 (1995)].

Studies on the physiological functions of serotonin receptors have also been making progress, and not only their relation to appetite, body temperature regulation, blood pressure regulation and the like body functions but also their relation to depression, anxiety, schizophrenia, sleep disorders and the like mental functions have been revealed [P. L. Bonate et al., *Clinical Neuropharmacology*, 14, 1–16 (1991)]. Actually, 5-HT$_{1A}$ receptor agonists, 5-HT$_2$ receptor inhibitors and 5-HT re-uptake inhibitors are now used in the clinical field. It has been reported also that, since a drug group classified as atypical among already known schizophrenia treating drugs has the affinity particularly for serotonin receptor 5-HT$_6$, the serotonin receptor 5-HT$_6$ is closely related to the efficacy of these drugs [R. D. Ward et al., *Neuroscience*, 64, 1105–1111 (1995)].

It has been reported that several atypical schizophrenia treating drugs including clozapine have strong affinity for the 5HT$_6$ receptor, and several typical schizophrenia treating drugs show high affinity for both of the 5HT$_6$ and 5HT$_7$ receptors [B. L. Roth et al., *J. Pharmacol. Exp. Ther.*, 268 (3), 1403–1410, 1994]. Also, it has been reported that a 5HT$_{1A}$ partial agonist, buspirone, has high therapeutic effect for patients having both symptoms of depression and anxiety [Tollefson G. D. et al., *Psychopharmacol. Bull.*, 27, 163–170, 1991]. In addition, the importance of serotonin receptors in various physiological functions was been reported in a large number, for example, it has been reported that certain N-butylpiperidines inhibit serotonin receptor 5-HT$_4$ selectively and are useful for the treatment of irritable bowel syndrome [L. M. Gaster et al., J. Med. Chem., 38, 4760–4763, 1995], and it has been assumed that 5-HT$_7$ exerts an important function in the human circadian rhythm regulation [T. W. Lovenberg et al., *Neuron*, 11, 449–458, 1993].

In addition, it is considered that they are exerting various physiological functions by distributing not only in human and animal brains but also broadly in smooth muscle tissues such as the spleen, stomach, ileum, small intestines, coronary vessel and the like [A. J. Sleight, *DN & P*, 214–223, 1997]. In consequence, creation of a substance which acts upon 5-HT$_7$ receptor is considerably profitable for the studies of physiological functions in these organs and the treatment and prevention of diseases induced by functional abnormality in these organs.

The present inventors have already found a substance which has strong ability to bind to the 5-HT$_7$ receptor in the living body. That is, according to the inventions by the present inventors (WO 98/00400, Japanese Patent Application No. 9-358380, Japanese Patent Application No. 9-358381, Japanese Patent Application No. 10-85913, Japanese Patent Application No. 10-136872, Japanese Patent Application No. 10-229709 and Japanese Patent Application No. 10-319336), there are provided novel tetrahydrobenzindole derivatives which strongly bind to 5-HT$_7$ receptor in the living body and pharmaceutical compositions which comprise these compounds.

As described above, novel tetrahydrobenzindole derivatives which strongly bind to 5-HT$_7$ receptor in the living body have been provided, but creation of a compound which selectively binds to the 5-HT$_7$ receptor will be useful for the treatment and prevention of various diseases which are considered to be induced by the abnormality of central and peripheral serotonin controlling functions, such as mental diseases (manic-depressive psychosis, anxiety, schizophrenia, epilepsy, sleep disorders, biological rhythm disorders, migraine and the like), cardiovascular diseases (hypertension and the like) and gastrointestinal disorders, and will also provide medicaments having high safety that can prevent generation of unexpected side effects. It will also provide compounds which have high utility value in studies on the elucidation of physiological functions of 5-HT$_7$ receptor whose functions are not clear yet.

Thus, the object of the invention is to provide a compound which has strong affinity for the 5-HT$_7$ receptor in the living body and binds selectively to the 5-HT$_7$ receptor.

DISCLOSURE OF THE INVENTION

In order to solve these problems, the present inventors have examined on various compounds. As a result, it was found that certain tetrahydrobenzindole derivatives have strong affinity for 5-HT$_7$ receptor in the living body and selectively bind to 5-HT$_7$ receptor, thereby resulting in the accomplishment of the invention. That is, according to the invention, novel tetrahydrobenzindole derivatives and pharmaceutical compositions which comprise these compounds are provided, and intermediates useful in producing these compounds are also provided. Accordingly, the invention comprises the following constructions.

1. A compound represented by formula (1):

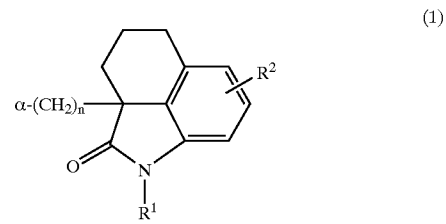

wherein $R^1$ represents a hydrogen atom, a lower alkyl group or an aralkyl group; $R^2$ represents a hydrogen atom, a halogen atom, a lower alkyl group, a hydroxy group, an alkoxy group, an acyl group, an acyloxy group, an alkoxycarbonyl group, a nitro group, an amino group, a substituted amino group, a carbamoyl group or an alkylcarbamoyl group, and n is an integer of from 2 to 6; and α represents the following formula (a), (b), (c), (d) or (e):

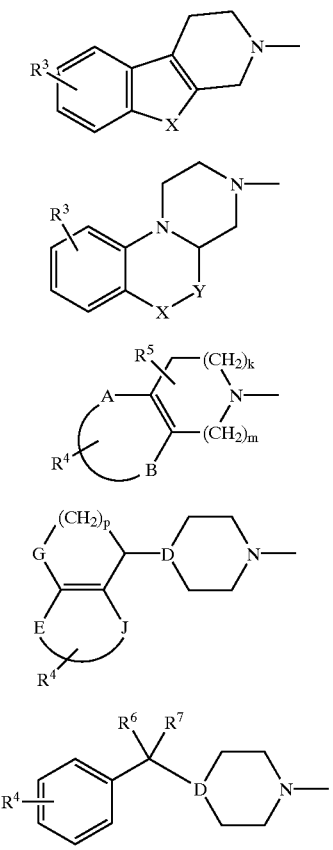

wherein
in formulae (a) and (b), $R^3$ represents a hydrogen atom, a halogen atom, a lower alkyl group, a hydroxy group or an alkoxy group, X represents $NR^{10}$, $NCONR^{11}R^{12}$, S, SO, $SO_2$ or O, $R^{10}$ represents a hydrogen atom, a lower alkyl group, an alkenyl group, an oxoalkyl group, an aralkyl group, a cyanoalkyl group, a hydroxyalkyl group, an alkoxyalkyl group, an aminoalkyl group, a substituted aminoalkyl group, an alkoxycarbonylalkyl group, a carbamoylalkyl group, an alkylcarbamoylalkyl group, an acyl group or an alkoxycarbonyl, $R^{11}$ and $R^{12}$ independently represent a hydrogen atom or a lower alkyl group, and Y represents a methylene group or a carbonyl group, in formula (c), $R^4$ represents a hydrogen atom, a halogen atom, a lower alkyl group, a hydroxy group, a cyano group, a trihalomethyl group, an alkoxy group, an alkylthio group, an alkylsulfinyl group, an alkylsulfonyl group, an alkoxycarbonyl, a sulfamoyl group, an amino group, a substituted amino group, a carbamoyl group, an alkylcarbamoyl group, an acyl group or a carboxy group, $R^5$ represents a hydrogen atom, a lower alkyl group, a hydroxy group, an alkoxy group, an acyl group, a phenyl group or a substituted phenyl group, k is 0 or an integer of from 1 to 3, m is 0 or an integer of from 1 to 3, and each of A and B represents a group which forms a benzene ring, a thiophene ring, a furan ring, an imidazole ring or a pyrazole ring via a double bond, with the proviso that k+m is an integer of from 1 to 3, and in formulae (d) and (e), $R^4$ is as defined in the foregoing, G represents $CH_2$, S, O or C=O, D represents CH or N, p is an integer of from 1 to 3, each of E and J represents a group which forms a benzene ring or a pyridine ring via a double bond, and $R^6$ and $R^7$ independently represent a hydrogen atom, a lower alkyl group, a hydroxy group, an alkoxy group, an acyl group, a phenyl group or a substituted phenyl group or a pharmaceutically acceptable salt thereof.

2. A compound according to the aforementioned item 1, which is represented by formula (1a):

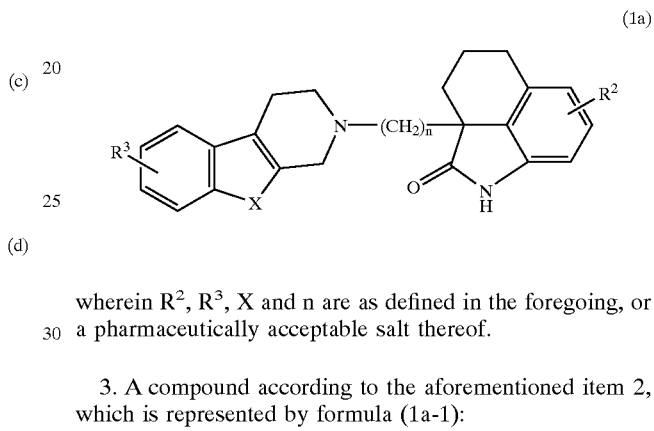

wherein $R^2$, $R^3$, X and n are as defined in the foregoing, or a pharmaceutically acceptable salt thereof.

3. A compound according to the aforementioned item 2, which is represented by formula (1a-1):

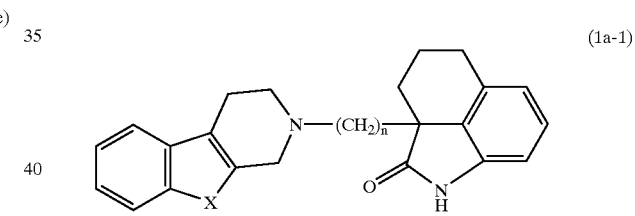

wherein X and n are as defined in the foregoing, or a pharmaceutically acceptable salt thereof.

4. A compound according to the aforementioned item 1, which is represented by formula (1b):

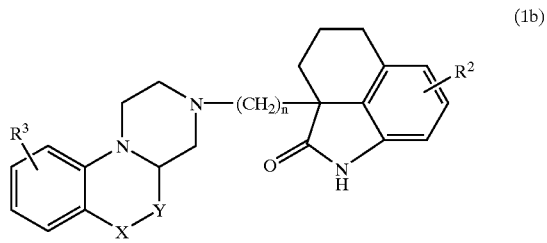

wherein $R^2$, $R^3$, X, Y and n are as defined in the foregoing, or a pharmaceutically acceptable salt thereof.

5. A compound according to the aforementioned item 4, which is represented by formula (1b-1):

(1b-1)

wherein X, Y and n are as defined in the foregoing, or a pharmaceutically acceptable salt thereof.

6. A compound according to the aforementioned item 1, which is represented by formula (1c):

(1c)

wherein $R^1$, $R^4$, $R^5$, A, B, k, m and n are as defined in the foregoing, or a pharmaceutically acceptable salt thereof.

7. The compound or a pharmceutically acceptable salt thereof according to the aforementioned item 6, wherein k+m is 2.

8. The compound or a pharmaceutically acceptable salt thereof according to the aforementioned item 6 or 7, wherein n is 4.

9. A compound according to claim 1, which is represented by formula (1d):

(1d)

wherein $R^4$, G, D, E, J, p and n are as defined in the foregoing, or a pharmaceutically acceptable salt thereof.

10. A compound according to the aforementioned item 1, which is represented by formula (1e):

(1e)

wherein $R^4$, $R^6$, $R^7$, D and n are as defined in the foregoing, or a pharmaceutically acceptable salt thereof.

11. A pharmaceutical composition which comprises any one of the compounds of the aforementioned items 1 to 10 or a pharmaceutically acceptable salt thereof.

12. A pharmaceutical composition for treatment or prevention of mental diseases, which comprises any one of the compounds of the aforementioned items 1 to 10 or a pharmaceutically acceptable salt thereof.

13. A compound represented by formula (aQ):

(aQ)

wherein Z represents $NR^{13}$, $NCONR^{11}R^{12}$, SO or $SO_2$, $R^{13}$ represents a carbamoylalkyl group, an alkylcarbamoylalkyl group, an alkenyl group or an oxoalkyl group, $R^{11}$ and $R^{12}$ independently represent a hydrogen atom or a lower alkyl group, Q represents a hydrogen atom or a protecting group and $R^3$ is as defined in the foregoing, or a salt thereof.

14. A compound represented by formula (bQ):

(bQ)

wherein $R^3$, Y, Z and Q are as defined in the foregoing, or a salt thereof.

MODE FOR CARRYING OUT THE INVENTION

In the descriptions of this specification concerning the chemical substances and production methods thereof, the term halogen atom means each atom of fluorine, chlorine, bromine and iodine, the term lower alkyl means methyl, ethyl or the like straight chain alkyl having from 1 to 4 carbon atoms and isopropyl, isobutyl, t-butyl or the like branched-chain alkyl or a halogen-substituted compound thereof, and the term base to be used as a catalyst means sodium hydroxide, potassium carbonate, triethylamine or the like. In addition, the term substituent group means a group other than hydrogen atom.

In the formula (1), each symbol has the following meaning;

$R^1$ represents hydrogen atom, lower alkyl or aralkyl, $R^2$ represents hydrogen atom, halogen atom, lower alkyl, hydroxy, alkoxy (preferably having from 1 to 4 carbon atoms, such as methoxy or ethoxy), acyl (preferably having from 1 to 4 carbon atoms), acyloxy (preferably having from 1 to 4 carbon atoms), alkoxycarbonyl (the alkyl moiety preferably having from 1 to 4 carbon atoms), nitro, amino, substituted amino (preferably, amino substituted by lower alkyl, such as dimethylamino or diethylamino), carbamoyl or alkylcarbamoyl (the alkyl moiety preferably having from 1 to 4 carbon atoms), and n is an integer of from 2 to 6.

In the formulae (a) and (b)

$R^3$ represents hydrogen atom, halogen atom, lower alkyl, hydroxy or alkoxy (preferably having from 1 to 4 carbon atoms, such as methoxy or ethoxy), X represents $NR^{10}$, $NCONR^{11}R^{12}$, S, SO, $SO_2$ or O, $R^{10}$ represents hydrogen atom, lower alkyl, alkenyl (preferably having from 1 to 4 carbon atoms), oxoalkyl (preferably having from 1 to 4 carbon atoms), aralkyl, cyanoalkyl (the alkyl moiety preferably having from 1 to 4 carbon atoms), hydroxyalkyl (preferably having from 1 to 4 carbon atoms), alkoxyalkyl (each alkyl moiety preferably having from 1 to 4 carbon atoms), aminoalkyl (preferably having from 1 to 4 carbon atoms), substituted aminoalkyl (preferably an alkylaminoalkyl in which each alkyl moiety has from 1 to 4 carbon atoms, such as dimethylaminoethyl), alkoxycarbonylalkyl (each alkyl moiety preferably having from 1 to 4 carbon atoms), carbamoylalkyl (the alkyl moiety preferably having from 1 to 4 carbon atoms, such as carbamoylmethyl or carbamoylethyl), alkylcarbamoylalkyl (each alkyl moiety preferably having from 1 to 4 carbon atoms), acyl (preferably having from 1 to 4 carbon atoms) or alkoxycarbonyl (the alkyl moiety preferably having from 1 to 4 carbon atoms, such as methoxycarbonyl or ethoxycarbonyl), $R^{11}$ and $R^{12}$ independently represent hydrogen atom or lower alkyl, and Y represents methylene or carbonyl.

In the compounds represented by the formula (aQ) or (bQ), which are novel intermediates among compounds in which the free valency N of the group represented by the formula (a) or (b) is substituted with Q (represents hydrogen atom or a protecting group), $R^3$ represents hydrogen atom, halogen atom, lower alkyl, hydroxy or alkoxy (preferably having from 1 to 4 carbon atoms, such as methoxy or ethoxy), Z represents $NR^{13}$, $NCONR^{11}R^{12}$, SO or $SO_2$, $R^{13}$ represents carbamoylalkyl (the alkyl moiety preferably having from 1 to 4 carbon atoms, such as carbamoylmethyl or carbamoylethyl), alkylcarbamoylalkyl (each alkyl moiety preferably having from 1 to 4 carbon atoms), alkenyl (preferably having from 1 to 4 carbon atoms, such as allyl) or oxoalkyl (preferably having from 1 to 4 carbon atoms, such as 2-oxo-propyl), and $R^{11}$ and $R^{12}$ independently represent hydrogen atom or lower alkyl.

In the formula (c),
$R^4$ represents hydrogen atom, halogen atom, lower alkyl, hydroxy, cyano, trihalomethyl (wherein the halogen atom is as defined in the foregoing and the three halogen atoms may be the same or different from one another, preferably trifluoromethyl or the like), alkoxy (preferably having from 1 to 4 carbon atoms, such as methoxy or ethoxy), alkylthio (preferably having from 1 to 4 carbon atoms, such as methylthio or ethylthio), alkylsulfinyl (preferably having from 1 to 4 carbon atoms), alkylsulfonyl (preferably having from 1 to 4 carbon atoms), alkoxycarbonyl (the alkyl moiety preferably having from 1 to 4 carbon atoms), sulfamoyl, amino, substituted amino (preferably amino substituted by lower alkyl, such as dimethylamino or diethylamino), carbamoyl, alkylcarbamoyl (preferably the alkyl moiety is lower alkyl, such as dimethylcarbamoyl), acyl (preferably having from 1 to 4 carbon atoms, such as acetyl) or carboxy,
$R^5$ represents hydrogen atom, lower alkyl, hydroxy, alkoxy (preferably having from 1 to 4 carbon atoms, such as methoxy or ethoxy) acyl (preferably having from 1 to 4 carbon atoms, such as acetyl), phenyl or substituted phenyl, and
k is 0 or an integer of from 1 to 3, m is 0 or an integer of from 1 to 3, with the proviso that k+m is an integer of from 1 to 3. Namely, the nitrogen atom binding to the methylene chain forms a five- to seven-membered ring, preferably a six-membered ring, and the nitrogen-containing hetero ring is condensed, via its double bond, with benzene ring, thiophene ring, furan ring, imidazole ring or pyrazole ring formed by A and B, so that the formula (c) as a whole represents indolinyl, tetrahydroquinolyl, tetrahydro isoquinolyl, 2,3,4,5-tetrahydro-3H-benzo[b]azepinyl, 2,3,4,5-tetrahydro-1H-benzo[c]azepinyl, 2,3,4,5-tetrahydro-1H-benzo[d] azepinyl, 4,5,6,7-tetrahydrothieno[3,2-c]pyridyl, 4,5,6, 7-tetrahydrofuro[3,2-c]pyridyl, 4,5,6,7-tetrahydropyrazolo[4,3-c]pyridyl and the like. Preferably, n is 4.

In the formulae (d) and (e),
$R^4$ is as defined in the aforementioned formula (c) and similar group is desirable, G represents $CH_2$, S, O or C=O, D represents CH or N, p is an integer of from 1 to 3, each of E and J represents a group which forms benzene ring or pyridine ring via a double bond, and $R^6$ and $R^7$ independently represent hydrogen atom, lower alkyl, hydroxy, alkoxy (preferably having from 1 to 4 carbon atoms, such as methoxy or ethoxy), acyl (preferably acetyl or the like), phenyl or substituted phenyl (preferably phenyl substituted by halogen, such as chlorophenyl or bromophenyl).

In this connection, in the formula (1), $R^2$, $R^3$, $R^4$ or $R^5$ is a symbol which can represent all hydrogen atoms on the ring, and when $R^2$, $R^3$, $R^4$ or $R^5$ is a substituent group, it can be substituted on any hydrogen atom on the ring independently, so that there will be no substitution or one or more positions will be substituted by the same or different groups.

The compounds provided by the invention are produced by the chemical synthesis methods described in the following.

The compound represented by the formula (1) (to be referred to as "compound (1) of the invention" hereinafter) can be obtained by allowing a compound represented by a formula (5) [in the formula, α is as defined in the foregoing] or a salt thereof prepared in advance to react with a compound represented by a formula (4) [in the formula, W is a halogen atom, an alkylsulfonic ester residue such as methanesulfonyloxy or ethanesulfonyloxy or an arylsulfonic acid ester residue such as benzenesulfonyloxy or p-toluenesulfonyloxy, and $R^1$, $R^2$ and n are as defined in the foregoing] (to be referred to as "compound (4)" hereinafter, the compounds represented by other formulae are also expressed in the same manner) prepared in advance (reaction formula 1).

Reaction Formula 1

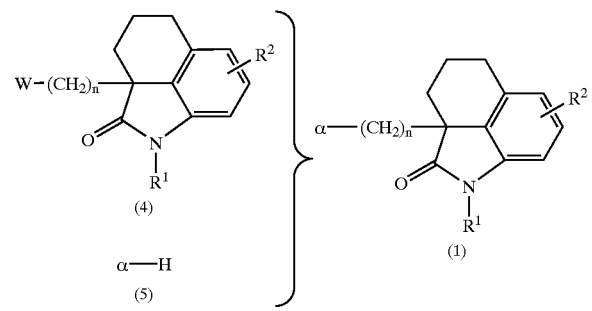

The above reaction is carried out in the presence or absence of a base without solvent or after dilution with an inert solvent at a temperature within the range of from ordinary temperature to heating temperature. Examples of the inert solvent to be used include dioxane, tetrahydrofuran, acetone, methyl ethyl ketone, acetonitrile, dimethylformamide and the like, and examples of the base to be used include salts of alkali metals, such as sodium carbonate, potassium carbonate and the like carbonates and sodium bicarbonate, potassium bicarbonate and the like bicarbonates, and trialkylamines, pyridine bases and the like.

The aforementioned compounds (1a), (1a-1), (1b), (1b-1), (1c), (1d) and (1e) can be produced by appropriately selecting respective substituent groups of the above compounds (4) and (5).

When $R^1$ is hydrogen atom in the compound (4) of the aforementioned reaction formula 1, a compound (4-2) is obtained by carrying out substitution reaction of respective aromatic ring of an organic synthesis material 2a,3,4,5-tetrahydrobenz[cd]indol-2-(1H)one [compound (2-1)] to obtain a compound (2-2) which is then allowed to react with a compound (3) [in the formula (3), W and n are as defined in the foregoing], or the compound (4-2) can be obtained by carrying out substitution reaction of respective aromatic ring of a compound (4-1) derived from the compounds (2-1) and (3) (reaction formula 2). In addition, the substituent group introduced on the aromatic ring may be converted into other substituent group by a chemical reaction before or after its reaction with the compound (5).

Reaction Formula 2

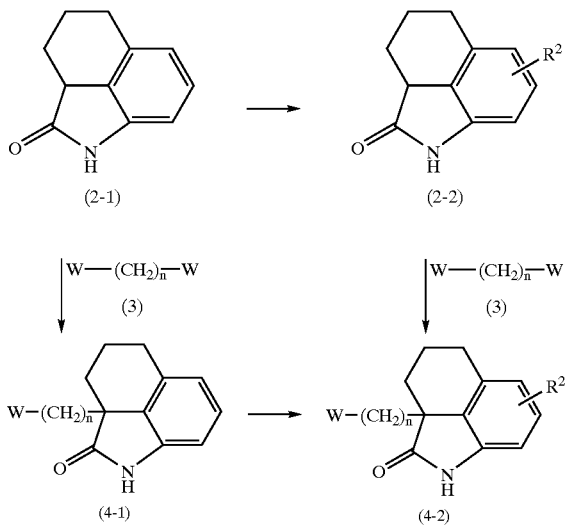

Also, when $R^1$ is a lower alkyl or an aralkyl, the following reaction step can be used.

Benz[cd]indol-2 (1H) one [compound (2-0)] is used as the starting material and allowed to react with a compound (6) [in the formula (6), W is as defined in the foregoing, and R is a lower alkyl group or an aralkyl group] in the presence of a base to obtain a compound (2-0-1),

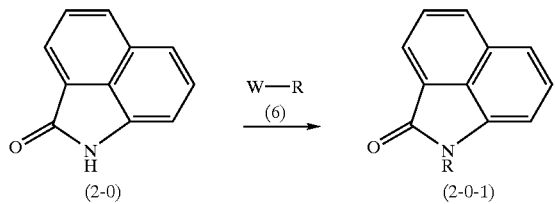

and then the compound (2-0-1) is allowed to undergo the reaction in an atmosphere of hydrogen using Raney nickel as a catalyst to obtain a compound (2-3).

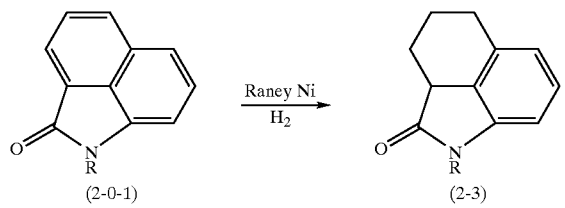

When the compound (2-3) is used instead of the compound (2-1) in the above reaction formula 2, a compound (4-3) in which $R^1$ in the compound (4) is R or a compound (4-4) in which $R^2$ is a substituent group can be obtained (reaction formula 3)

Reaction Formula 3

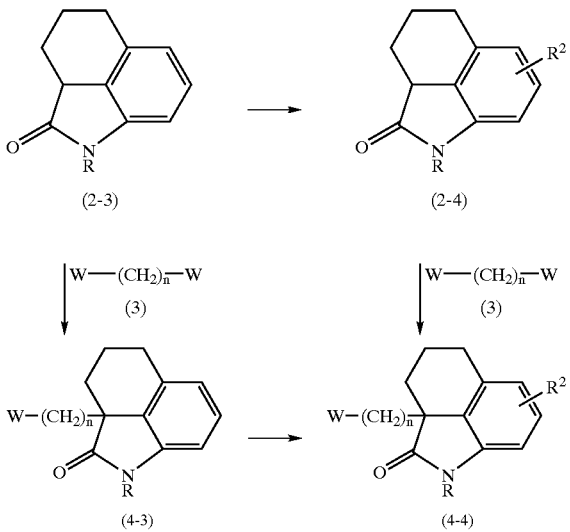

Also, it is possible to carry out synthesis of the compound (1) of the invention using the following compound (4-5) instead of the compound (4) in the aforementioned reaction formula 1.

The compound (4-5) is synthesized using an alkene represented by $CH_2=CH-(CH_2)_{n-1}-W$ [wherein n and W are as defined in the foregoing] or $-(CH_2)_{n-1}-W$ [wherein q is protected hydroxyl group, and n and W are as defined in the foregoing] instead of the compound (3) in the aforementioned reaction formula 2 or 3.

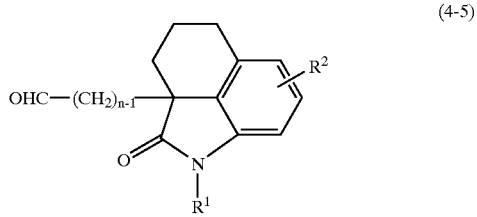

The compound (2-1-4) is allowed to react with $CH_2=CH-(CH_2)_{n-1}-W$ or $q-(CH_2)_n-W$ in the presence of a base and then converted into an aldehyde compound by allowing the alkene to react with osmium tetroxide and sodium periodate, or converted into an aldehyde compound represented by the compound (4-5) by, for example, carrying out deprotection and oxidation of q, and the desired compound (1) can be obtained by carrying out reductive aminoalkylation reaction of the aldehyde compound with a secondary amine represented by the compound (5) using sodium triacetoxyborohydride.

It is desirable to introduce the substituent group $R^2$ into aromatic ring by a generally known aromatic electrophilic substitution reaction. Examples of the aromatic electrophilic substitution reaction include halogenation, Friedel-Crafts' reaction-based alkylation and acylation and nitration.

In a preferred example of the halogenation, the reaction is carried out at a temperature of from 0° C. to reflux temperature in carbon disulfide, carbon tetrachloride, chloroform, dichloromethane, 1,2-dichloroethane, acetic acid, water or the like solvent in the presence or absence of an appropriate catalyst. Examples of the halogenation agent to be used include fluorine, chlorine, bromine and iodine, as well as 1-fluoropyridinium trifurate, 1-fluoro-2,6-dichloropyridinium tetrafluoroborate and the like unsubstituted or substituted N-fluoropyridinium salts, N-fluoro-N-propyl-p-toluenesulfonamide and the like N-fluoro-N-alkyl-sulfonamides, N-fluorobenzenesulfonimide and the like N-fluorosulfonimides, sodium hypochlorite, N-bromosuccinimide and the like.

The Friedel-Crafts' reaction is carried out at a temperature of from 0° C. to reflux temperature in carbon disulfide, chloroform, dichloromethane, 1,2-dichloroethane, nitrobenzene or the like solvent in the presence of a catalyst. Examples of the alkylation agent to be used include halogenated hydrocarbons, as well as methanol, ethanol and the like alcohols and propene and the like olefin compounds. Examples of the acylation agent to be used include acetyl chloride, propyl chloride and the like acyl halides, as well as acetic anhydride and the like acid anhydrides and acetic acid, propionic acid and the like carboxylic acids. Alternatively, an acid chloride derivative is obtained using oxalic acid chloride, triphosgene or the like and then hydrolyzed using water, alcohol, amines and the like to convert it into respective carboxylic acid derivative, ester derivative and amide derivative. Examples of the catalyst to be used desirably include aluminum chloride, iron chloride, boron trifluoride, tin chloride, zinc chloride and the like Lewis acids, as well as hydrogen fluoride, sulfuric acid, polyphosphoric acid and the like proton acids.

In an example of the nitration, the reaction is carried out using concentrated nitric acid and concentrated sulfuric acid or using nitric acid in water, acetic acid or acetic anhydride solution. In addition, ethyl nitrate and the like nitric acid esters, acetyl nitrate and the like mixed acids and nitronium tetrafluoroborate and the like nitronium salts can also be used.

As occasion demands, the substituent group $R^2$ introduced into the aromatic ring may be converted into other substituent group by a chemical reaction. The reaction may be carried out either before the reaction with the compound (5) or after completion of the reaction with the compound (5) in the reaction formula 1, with the proviso that it does not exert influence upon other functional groups, structures and the like. For example, acetyl group or the like acyl group can be converted into corresponding acyloxy group by allowing it to react with m-chloroperbenzoic acid, pertrifluoroacetic acid or the like peroxide in the presence of trifluoroacetic acid or the like acid catalyst as occasion demands, thereby effecting insertion of oxygen atom between the aromatic ring and carbonyl group. Thereafter, the acyloxy group can be converted into alkoxy group by removing the acyl group through hydrolysis or the like method and then allowing it to react with methyl iodide or the like alkylation agent in the presence of potassium carbonate, sodium bicarbonate or the like base. Also, methoxycarbonyl group or the like ester group can be converted into a carbamoyl derivative, an amide derivative or the like, when it is allowed to react, directly or after its hydrolysis into carboxylic acid, with ammonia, a primary amine, a secondary amine or the like via an active ester or the like reactive derivative.

In the aforementioned reaction formula 2, the compound (3) belongs to a so-called reaction intermediate and is generally available as a synthetic reagent or synthesized from diols represented by a formula HO—$(CH_2)_n$13 OH [wherein n is as defined in the foregoing]. That is, a diol is obtained as a dihalide by allowing it to react with thionyl chloride or thionyl bromide or as a disulfonate by allowing it to react with methanesulfonyl chloride or the like alkyl-sulfonic acid halide or benzenesulfonyl chloride or the like arylsulfonic acid halide. As another example of the halogenation reaction, halogenation using carbon tetrachloride or carbon tetrabromide in the presence of triphenylphosphine can also be used.

Next, the compound (5) (α-H) shown in the aforementioned reaction formula 1 is described.

The compound (5) is any one of the groups (a) to (e) in which hydrogen atom is substituted on the N having free valency.

In the following, a compound in which hydrogen atom is substituted on the free valency N of the group (a) is called compound (aH). In the same manner, compounds in which hydrogen atom is substituted on the free valency N of the groups (b) to (e) are called compounds (bH) to (eH).

Compound (aH) is described.

When X represents either $NR^{10}$ or $NCONR^{11}R^{12}$, the compound can be derived using commercially available 2,3,4,9-tetrahydro-1H-pyrido[3,4-b]indoles or from a commercially available tryptamine derivative and formaldehyde by, for example, the Pictet-Spengler reaction (e.g., *Organic Reactions*, 6, 151, 1951). Also, 9-position-modified products of 2,3,4,9-tetrahydro-1H-pyrido[3,4-b]indole, derived from them by various chemical reactions, may be used. Their examples include 9-alkyl derivatives, 9-acyl derivatives, 9-carbamoyl derivatives, 9-alkoxycarbonyl derivatives and the like.

The aforementioned 9-position-modified products of 2,3,4,9-tetrahydro-1H-pyrido[3,4-b]indole can be obtained by protecting the 2-position secondary amino group of 2,3,4,9-tetrahydro-1H-pyrido[3,4-b]indoles with a generally used protecting group, carrying out alkylation, acylation or the like chemical reaction and then effecting deprotection. It is desirable that the protecting group to be used is stable under alkylation, acylation and the like chemical reaction conditions and can be deprotected easily, and its examples include t-butoxycarbonyl group, benzyloxycarbonyl group or the like carbamate, as well as benzyl group and the like.

As an example of the synthesis of the aforementioned 9-position-modified product of 2,3,4,9-tetrahydro-1H-pyrido[3,4-b]indole, it is desirable to carry out the reaction of a 2-position amino group-protected 2,3,4,9-tetrahydro-1H-pyrido[3,4-b]indole derivative within the range of from low to heating temperature in the presence of sodium hydride, n-butyl lithium, lithium diisopropylamide or the like strong base, after its dilution with tetrahydrofuran, diethyl ether, toluene, 1,2-dimethoxyethane, dimethylformamide, dimethyl sulfoxide or the like inert solvent. Examples of the alkylation agent to be used include methyl iodide, ethyl bromide, allyl bromide or the like straight chain alkyl halide or straight chain alkenyl halide and isopropyl bromide, isobutyl bromide or the like branched-chain alkyl halide, as well as chloromethyl methyl ether, bromoacetonitrile, benzyl bromide, bromoacetamide, methyl bromoacetate, 2-chloro-N,N-dimethylethylamine and the like, and examples of the acylation agent to be used include acetyl chloride, propionyl chloride, isobutyryl chloride or the like acyl halide, as well as dimethylcarbamoyl chloride, diethylcarbamoyl chloride, methyl chloroformate, ethyl chloroformate and the like.

In addition, the 9-carbamoyl derivative and 9-alkoxycarbonyl derivative of 2,3,4,9-tetrahydro-1H-pyrido[3,4-b]indole can also be synthesized by subjecting the compound to chloroformylation with triphosgene and then allowing it to react with ammonia, methylamine and the like amines or methanol, ethanol and the like alcohols, in tetrahydrofuran, diethyl ether, toluene, 1,2-dimethoxyethane, dimethylformamide, dimethyl sulfoxide or the like inert solvent in the presence of sodium hydride, n-butyl lithium, lithium diisopropylamide or the like strong base.

Also, when X is any one of S, SO, $SO_2$ and O, the compound (aH) can be synthesized by a generally known method. For example, 3,4-dihydro-1H-benzo[4,5]thieno[2,3-c]pyridine can be synthesized via cyclization, amidation, amide reduction and Pictet-Spengler cyclization of 4-(phenylthio)acetoacetic acid ethyl ester which is obtained from substituted or unsubstituted thiophenol and 4-chloroacetoacetic acid ethyl ester (*J. Heterocyclic Chem.*, 16, 1321, 1979). In addition, it can be converted into a sulfoxide derivative or a sulfone derivative by oxidizing the 9-position sulfur atom. For example, 3,4-dihydro-9-oxo-9-$\lambda^4$-1H-benzo[4,5]thieno[2,3-c]pyridine or 3,4-dihydro-9,9-dioxo-9-$\lambda^6$-1H-benzo[4,5]thieno[2,3-c]pyridine can be obtained by protecting the 2-position amino group of 3,4-dihydro-1H-benzo[4,5]thieno[2,3-c]pyridine with t-butoxycarbonyl group, benzyloxycarbonyl group or the like protecting group, and then deprotecting the sulfur atom by its selective oxidation with m-chloroperbenzoic acid or hydrogen peroxide. On the other hand, 3,4-dihydro-1H-benzo[4,5]furo[2,3-c]pyridine can be synthesized, for example, via nitrile reduction, formamidation, cyclization and imine reduction of 3-cyanomethylbenzo[b]furan which is obtained from 3-(2H)-benzo[b]furanone and diethylcyanomethyl phosphate (JP-A-63-22581; the term "JP-A" as used herein means an "unexamined published Japanese patent application").

The compound (aQ) (Q is hydrogen atom or a protecting group) as a novel intermediate for the production of the compound (1) of the invention is a case in which the aforementioned X is Z and can be synthesized in the same manner as described above.

Next, the compound (bH) is described.

When X is O and Y is methylene, this can be synthesized by a generally known method. That is, as shown in the reaction formula 4, the primary amino group of a benzoxazine derivative (7) (Gupta, S. P. et al., *Synthesis*, 9, 660, 1974) is protected with benzyloxycarbonyl group or the like appropriate protecting group (Q) to obtain a compound (8), and then a compound (bH-1) can be synthesized via a chloroacetylated derivative (9), its cyclization to a pyrazinobenzoxazine derivative (10), a compound (11) by amide reduction and removal of the protecting group (Q) (E. W. Baxter et al., *Bioorg. Med. Chem. Lett.*, 7, 763, 1997).

Also, when X is any one of S, SO and SO and Y is methylene, 1,2,3,4,4a,5-hexahydropyrazino[2,1-c]-1,4-benzthiazine can be synthesized in accordance with the method shown in the reaction formula 4 from a generally known compound 3,4-dihydro-3-aminomethyl-2H-1,4-benzthiazine (P. Melloni et al., *J. Heterocyclic Chem.*, 20, 139, 1983), and a sulfoxide derivative and a sulfone derivative of the compound (bH) can be obtained by deprotecting the 6-position sulfur atom of the compound (11) through its selective oxidation with m-chloroperbenzoic acid or hydrogen peroxide.

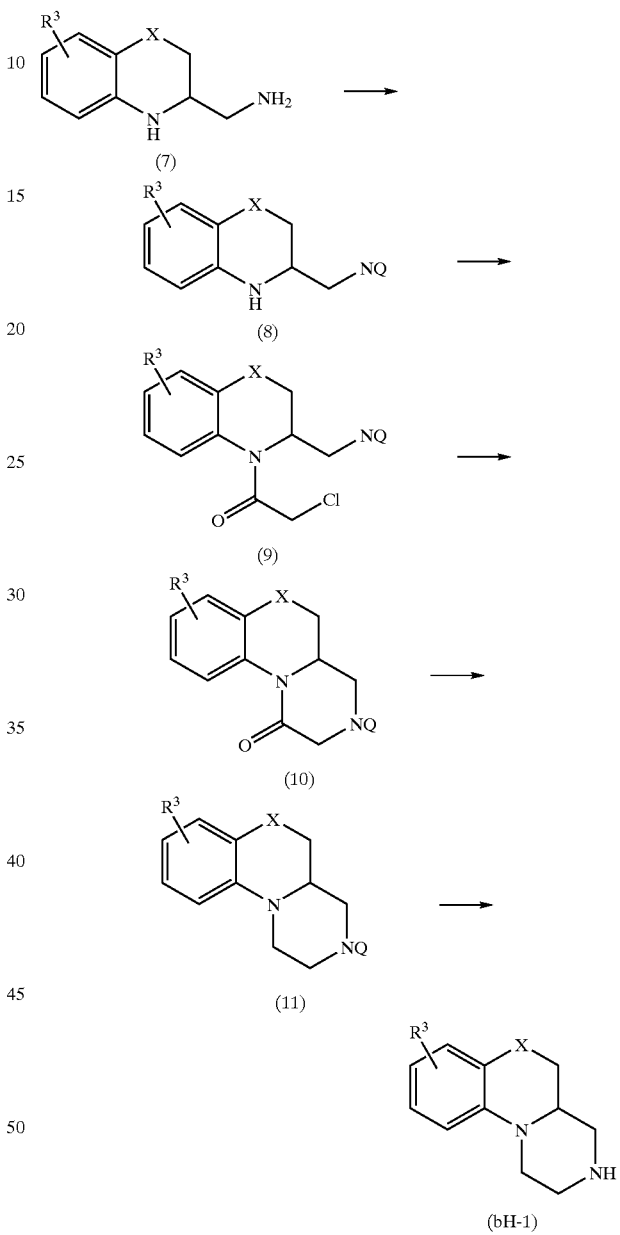

Reaction Formula 4

Also, when X is either $NR^{10}$ or $NCONR^{11}R^{12}$ and Y is carbonyl or methylene, the compound (bH) can be synthesized from a generally known compound 2,3,4,4a-tetrahydro-1H-pyrazino[1,2-a]quinoxalin-5(6H)-one derivative or 2,3,4 ,4a,5,6-hexahydro-1H-pyrazino[1,2-a] quinoxaline derivative (JP-A-52-114000) by carrying out alkylation, acylation or the like chemical modification. For example, an alkyl group can be introduced to the amido nitrogen by allowing a compound in which the 3-position of 2,3,4,4a-tetrahydro-1H-pyrazino[1,2-a]quinoxalin-5(6H)-one is protected with benzyloxycarbonyl group or the like appropriate protecting group to react with methyl iodide, ethyl bromide or the like alkylation agent in the presence of sodium hydride or the like base. Also, the compound (bH) as a 6-position-modified product can be obtained by allowing a compound in which the 3-position of 2,3,4,4a,5,6-hexahydro-1H-pyrazino[1,2-a]quinoxaline is protected with benzyloxycarbonyl group or the like appropriate protecting group to react with acetyl chloride, propionyl chloride, isobutyryl chloride or the like acyl halide and trifluoroacetic acid anhydride, dimethylcarbamoyl chloride, diethylcarbamoyl chloride, methyl chloroformate, ethyl chloroformate or the like acylation agent, in the presence of triethylamine or the like base.

The compound (bQ) (Q is hydrogen atom or a protecting group) as a novel intermediate for the production of the compound (1) of the invention is a case in which the aforementioned X is Z and can be synthesized in the same manner as described above.

Next, the method for synthesizing the compound (cH) which is an intermediate for the production of the compound (1) of the invention is described in detail.

When benzene ring is formed by a carbon-carbon double bond of the nitrogen-containing hetero ring and the groups A and B which bind to its constituting carbon atoms, and also when k+m is 3, it can be derived from a generally known compound 2,3,4,5-tetrahydro-benzo[c]azepin-1-one or 1,3,4,5-tetrahydro-benzo[b]azepin-2-one [*Tetrahedron*, 49, 1807, 1993].

Also, when thiophene ring is formed by a carbon-carbon double bond of the nitrogen-containing hetero ring and the groups A and B which bind to its constituting carbon atoms, various derivatives of the compound (cH) can be synthesized from a generally known compound 4,5,6,7-tetrahydrothieno[3,2-c]pyridine-2-carboxylic acid [JP-A-5-60836], 4,5,6,7-tetrahydrothieno[2,3-c]pyridine-2-carboxylic acid, 5,6,7,8-tetrahydro-4H-thieno[3,2-c]azepine-2-carboxylic acid or 5,6,7,8-tetrahydro-4H-thieno[2,3-c]azepine-2-carboxylic acid [WO 94/21599].

Also, when furan ring is formed by a carbon-carbon double bond of the nitrogen-containing hetero ring and the groups A and B which bind to its constituting carbon atoms, various derivatives of the compound (cH) can be synthesized from a generally known compound such as 4,5,6,7-tetrahydrofuro[3,2-c]pyridine, 4,5,6,7-tetrahydrofuro[2,3-c]pyridine, 5,6,7,8-tetrahydro-4H-furo[2,3-c]azepine or 5,6,7,8-tetrahydro-4H-furo[2,3-d]azepine [JP-A-9-118681].

Also, when pyrazole ring is formed by a carbon-carbon double bond of the nitrogen-containing hetero ring and the groups A and B which bind to its constituting carbon atoms, and also when k is 0, it can be synthesized by a generally known method. That is, as shown in the following reaction formula 5, the compound (cH-1) (a compound in which $Q^1$ of the compound (cQ-1) is H) can be synthesized by firstly obtaining a compound (13) by allowing a protected ketocyclic amine (12) [wherein $Q^1$ is benzyl or the like protecting group, and m is an integer of from 1 to 3] to react with excess amount of an N,N-dialkylformamidodimethylacetal derivative generally at from 50° C. to 150° C. for a period of from 30 minutes to 10 hours, subsequently obtaining the compound (cQ-1) by condensing the compound (13) with from 1 to 5 equivalents of hydrazine or a lower alkylhydrazine generally at from 20° C. to 100° C. for from 10 minutes to 30 hours using methanol or the like lower alcohol as the solvent, and then removing the protecting group [JP-A-6-73056].

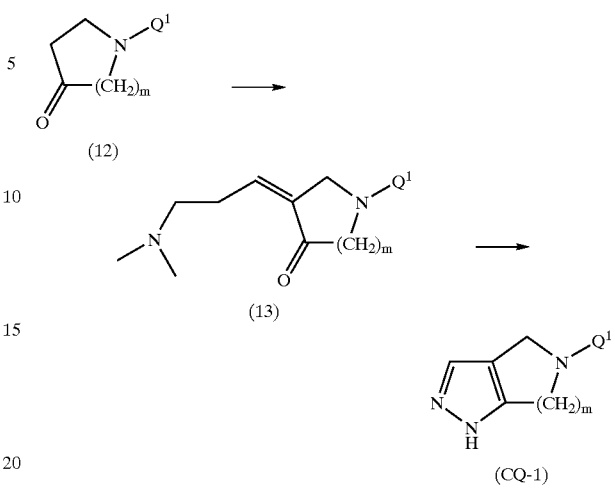

Reaction Formula 5

In the above synthesis method of the compound (cH), the substituent groups $R^4$ and $R^5$ of the compound (cH) can be optionally selected from those which are present on the ring of a compound to be used as the material, with the proviso that they do not hinder the above reactions, and these substituent groups can be substituted after synthesis of the compound (cH). Their typical examples include, as $R^4$, halogen atom, lower alkyl, hydroxy, cyano, trihalomethyl (wherein the halogen atom is as defined in the foregoing and the three halogen atoms may be the same or different from one another, preferably trifluoromethyl or the like), alkoxy (preferably having from 1 to 4 carbon atoms, such as methoxy or ethoxy), alkylthio (preferably having from 1 to 4 carbon atoms, such as methylthio or ethylthio), alkylsulfinyl (preferably having from 1 to 4 carbon atoms), alkylsulfonyl (preferably having from 1 to 4 carbon atoms), alkoxycarbonyl (the alkyl moiety preferably having from 1 to 4 carbon atoms), sulfamoyl, amino, substituted amino (preferably amino substituted by lower alkyl, such as dimethylamino or diethylamino), carbamoyl, alkylcarbamoyl (preferably the alkyl moiety is lower alkyl, such as dimethylcarbamoyl), acyl (preferably having from 1 to 4 carbon atoms, such as acetyl) and carboxy, and as $R^5$, hydrogen atom, lower alkyl, hydroxy, alkoxy (preferably having from 1 to 4 carbon atoms, such as methoxy or ethoxy), acyl (preferably having from 1 to 4 carbon atoms, such as acetyl), phenyl and substituted phenyl.

The secondary amines represented by the compound (cH) are shown below more illustratively;

indoline, 2-methylindoline, 2,3-dimethylindoline, 1,2,3,4-tetrahydroquinoline, 6-fluoro-1,2,3,4-tetrahydro-2-methylquinoline, 1,2,3,4-tetrahydroisoquinoline, 6,7-dimethoxy-1,2,3,4-tetrahydroisoquinoline, 6,7-dihydroxy-1,2,3,4-tetrahydroisoquinoline,
6,7-dihydroxy-1,2,3,4-tetrahydro-1-methylisoquinoline,
1-[5-chloro-2-(methylamino)-phenyl]-1,2,3,4-tetrahydroisoquinoline,
2,3,4,5-tetrahydro-1H-benzo[b]azepine,
2,3,4,5-tetrahydro-1H-benzo[c]azepine,
5-phenyl-2,3,4,5-tetrahydro-1H-benzo[c]azepine,
4,5,6,7-tetrahydrothieno[3,2-c]pyridine,
4,5,6,7-tetrahydrothieno[2,3-c]pyridine,
2-methyl-4,5,6,7-tetrahydrothieno[3,2-c]pyridine,
3-methyl-4,5,6,7-tetrahydrothieno[3,2-c]pyridine,
2,3-dimethyl-4,5,6,7-tetrahydrothieno[3,2-c]pyridine,
4,5,6,7-tetrahydrothieno[3,2-c]pyridine-2-carboxylic acid,
4,5,6,7-tetrahydrothieno[3,2-c]pyridine-2-carboxylic acid methyl ester,
2-carbamoyl-4,5,6,7-tetrahydrothieno[3,2-c]pyridine,
2-dimethylcarbamoyl-4,5,6,7-tetrahydrothieno[3,2-c]pyridine,
4,5,6,7-tetrahydrofuro[3,2-c]pyridine,
4,5,6,7-tetrahydrofuro[2,3-c]pyridine,
4,5,6,7-tetrahydro-1H-pyrazolo[4,3-c]pyridine,
4,5,6,7-tetrahydro-2-methyl-2H-pyrazolo[4,3-c]pyridine,
4,5,6,7-tetrahydro-3-methyl-1H-pyrazolo[4,3-c]pyridine,
4,5,6,7-tetrahydro-3H-imidazo[4,5-c]pyridine and the like.

Next, methods for the synthesis of the compounds (dH) and (eH) as intermediates for the production of the compound (1) of the invention are described in detail.

Regarding the compound (dH), ketone of a corresponding compound (14) [wherein $R^4$, G, E, J and p are as defined in the foregoing] is converted into alcohol form of a compound (15) by reducing it with sodium borohydride (reaction formula 6).

Reaction Scheme 6

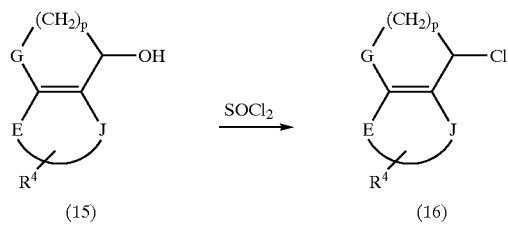

(14) → (15)

Next, the compound (15) is converted into a compound (16) by its chlorination using thionyl chloride (reaction formula 7).

Reaction Scheme 7

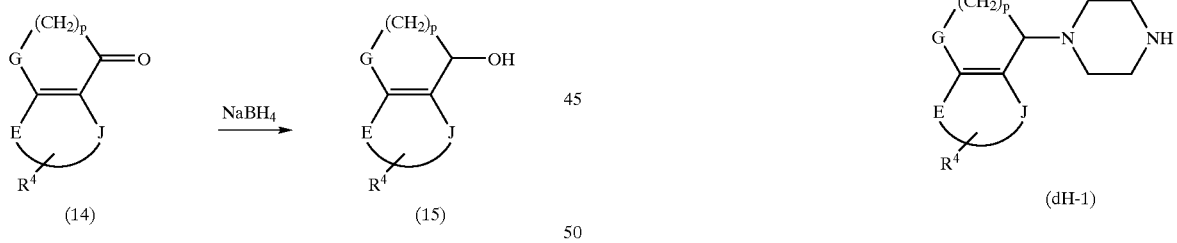

(15) → (16)

The compound (16) is condensed with a compound (17) N-t-butoxycarbonylpiperazine in the presence of a base to obtain a compound (18) (reaction formula 8).

Reaction Formula 8

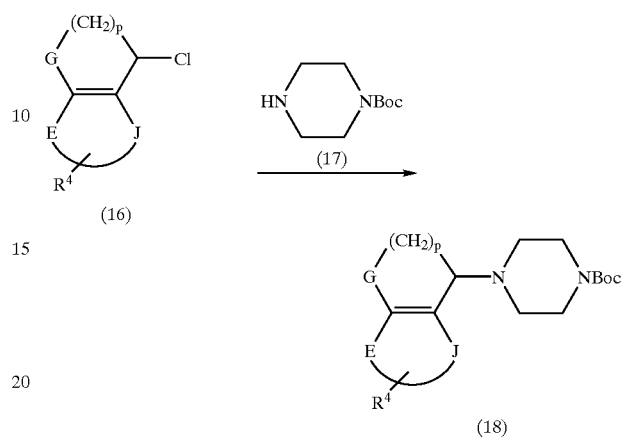

(16) + (17) → (18)

By further subjecting the compound (18) to de-t-butoxycarbonylation under an acidic condition, a compound (dH-1) is synthesized (reaction formula 9).

Reaction Formula 9

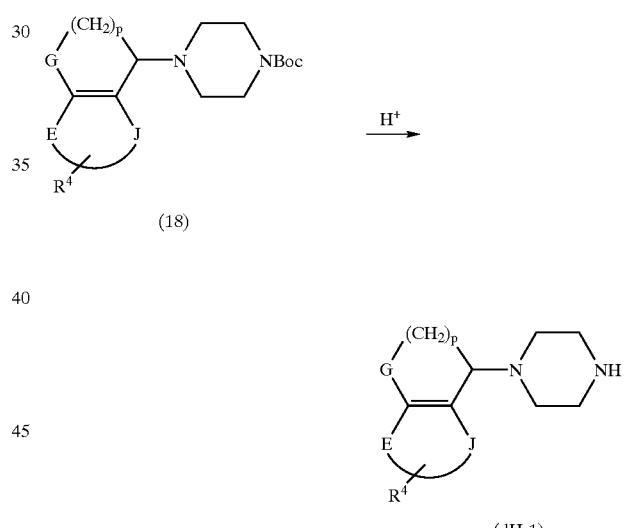

(18) → (dH-1)

As another example of the synthesis of the compound (dH), firstly, 4-bromopyridine as a compound (19) is allowed to react with the corresponding ketone compound (14) in ether using n-butyl lithium to obtain a compound (20) (reaction formula 10).

Reaction Formula 10

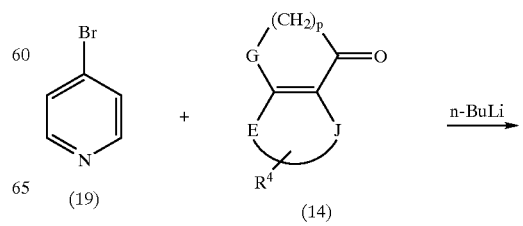

(19) + (14) → (n-BuLi)

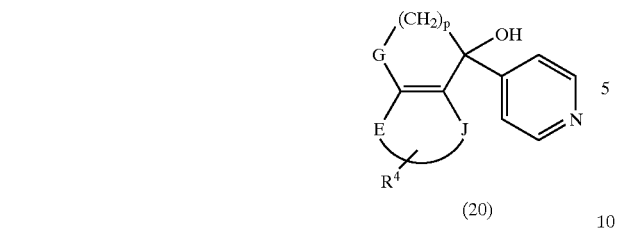

(20)

By reducing the compound (20) in an atmosphere of hydrogen using platinum oxide as a catalyst, a compound (dH-2) is synthesized (reaction formula 11).

Reaction Formula 11

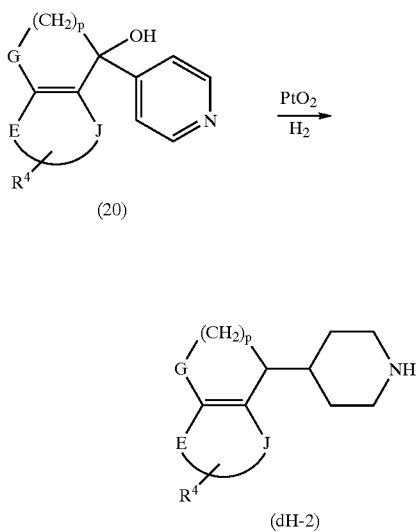

Regarding the compound (eH), a compound (21) [wherein y is a halogen atom, and $R^4$, $R^6$ and $R^7$ are as defined in the foregoing] is condensed with the compound (17) N-t-butoxycarbonylpiperazine in the presence of a base to obtain a compound (22).

Reaction Formula 12

By further subjecting the compound (22) to de-t-butoxycarbonylation under an acidic condition, a compound (eH-1) is synthesized (reaction formula 13).

Reaction Formula 13

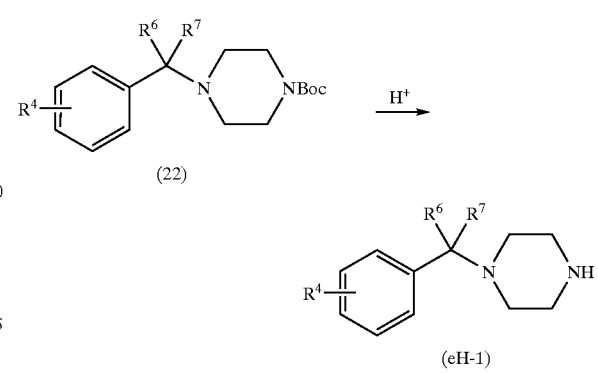

As another example of the synthesis of the compound (eH), firstly, 4-bromopyridine as the compound (19) is allowed to react with a corresponding ketone represented by a compound (23) [wherein $R^4$ is as defined in the foregoing, and $R^8$ is lower alkyl, phenyl or substituted phenyl group] in ether using n-butyl lithium to obtain a compound (24) (reaction formula 14).

Reaction Scheme 14

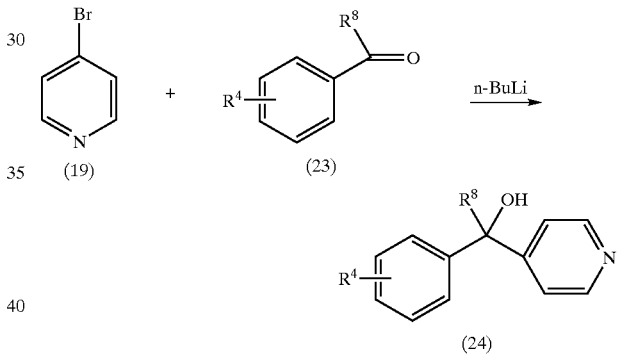

By reducing the compound (24) in an atmosphere of hydrogen using platinum oxide as a catalyst, a compound (eH-2) is synthesized (reaction formula 15).

Reaction Formula 15

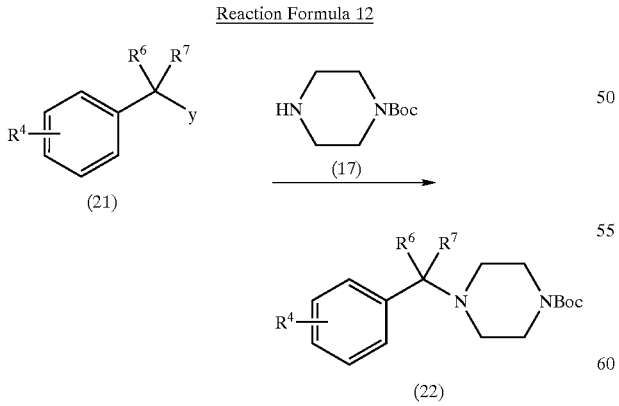

By further reducing the compound (eH-2) in an atmosphere of hydrogen using palladium-carbon as a catalyst, a compound (eH-3) is synthesized (reaction formula 16).

Reaction Formula 16

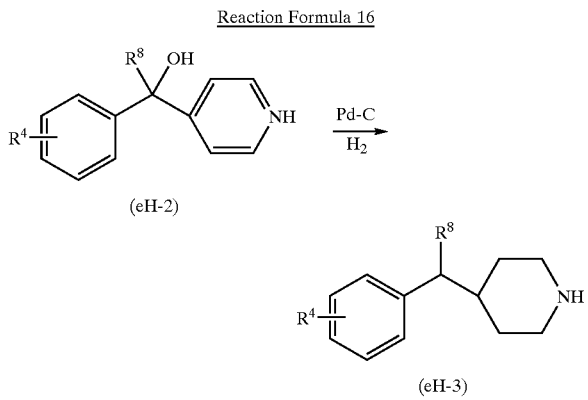

(eH-2)

(eH-3)

As shown in the aforementioned reaction formula 6, the compound (14) can be converted into the compound (15) using sodium borohydride. This reaction is generally carried out after dilution with an alcohol or water and progresses within the range of from ordinary temperature to heating. Examples of the alcohol to be used include methanol, ethanol and the like.

As shown in the aforementioned reaction formula 7, the compound (16) is obtained by chlorinating the compound (15) using thionyl chloride. This reaction is carried out without solvent or by diluting with a chlorinated solvent or an aromatic solvent. Examples of the solvent to be used include dichloromethane or chloroform as the chlorinated solvent and benzene, toluene or the like as the aromatic solvent.

As shown in the aforementioned reaction formulae 8 and 12, the compound (16) or (21) is converted into the desired compound (18) or (22) by carrying out its reaction with the compound (17), N-t-butoxycarbonylpiperazine. This reaction is carried out without solvent or after dilution with an inert solvent and progresses in the presence or absence of a base, in the presence or absence of a catalytically effective amount of potassium iodide or sodium iodide and within the range of from ordinary temperature to heating temperature. Examples of the inert solvent to be used include dioxane, tetrahydrofuran, acetonitrile, dimethylformamide, methyl ethyl ketone and the like, and examples of the base to be used include salts of alkali metals, such as sodium carbonate, potassium carbonate and the like carbonates and sodium bicarbonate, potassium bicarbonate and the like bicarbonates, and trialkylamines, pyridine bases and the like, or the secondary amine itself to be used as the material substance may also serve as the base when used in an excess amount.

As shown in the aforementioned reaction formulae 9 and 13, the compound (18) or (22) can be converted into the compound (dH-1) or (eH-1) by removing the t-butoxycarbonyl group under an acidic condition. Examples of the acid to be used include hydrochloric acid, trifluoroacetic acid and the like. As shown in the aforementioned reaction formulae 10 and 14, the compound (19) can be converted into the compound (20) or (24) by allowing it to react with the compound (14) or (23) using n-butyl lithium. The reaction is carried out after dilution with an ether solvent and progresses within the range of from −78° C. to room temperature. Examples of the ether solvent to be used include diethyl ether, tetrahydrofuran, dimethoxyethane and the like.

As shown in the aforementioned reaction formulae 11 and 15, the compound (20) or (24) can be converted into the compound (dH-2) or (eH-2) by its catalytic hydrogen reduction in the presence of platinum oxide. As shown in the aforementioned reaction formula 16, the compound (eH-3) is obtained from the compound (eH-2) by its catalytic hydrogen reduction in the presence of Pd-C.

These reactions are carried out after dilution with a polar solvent or a non-polar solvent and progress under ordinary pressure or under compression. Examples of the solvent to be used include water, an alcohol or acetic acid as the polar solvent and ether, benzene, hexane or the like as the non-polar solvent.

In the aforementioned synthesis method of the compound (dH) or (eH), the substituent groups $R^4$, $R^6$ and $R^7$ can be optionally selected from those which are present on the benzene and pyridine ring of the compound (14), (21) or (23) to be used as the material, with the proviso that they do not hinder the above reactions.

The compound (14) as the synthesis material ketones of the compound (dH) is shown below more illustratively;

1-indanone,
6-methyl-1-indanone,
4-methyl-1-indanone,
5-fluoro-1-indanone,
5-chloro-1-indanone,
5-bromo-1-indanone,
4-hydroxy-1-indanone,
4-methoxy-1-indanone,
5-methoxy-1-indanone,
6-methoxy-1-indanone,
α-tetralone,
5-hydroxy-1-tetralone,
5-methoxy-1-tetralone,
6-methoxy-1-tetralone,
7-methoxy-1-tetralone,
1-benzosuberone,
8-fluoro-1-benzosuberone,
4-chromanone,
thiochromanone-4-one,
6-fluoro-4-chromanone,
6-methyl-4-chromanone,
6-chloro-4-chromanone.

The compound (21) as the synthesis material halides of the compound (eH) is shown below more illustratively;

benzyl chloride,
benzyl bromide,
(1-bromoethyl)benzene,
2-fluorobenzyl chloride,
2-chlorobenzyl chloride,
2-chlorobenzyl bromide,
2-bromobenzyl bromide,
2-methylbenzyl bromide,
2-methylbenzyl chloride,
3-fluorobenzyl chloride,
4-fluorobenzyl bromide,
4-fluorobenzyl chloride,
3-fluorobenzyl bromide,
3-chlorobenzyl chloride,
4-chlorobenzyl chloride,
3-chlorobenzyl bromide,
3-bromobenzyl chloride, 3-bromobenzyl bromide,
4-bromobenzyl bromide,
3-methylbenzyl chloride,
3-methylbenzyl bromide,
4-methylbenzyl chloride,
4-methylbenzyl bromide,
4-t-butylbenzyl bromide,
2-trifluoromethylbenzyl chloride,
2-trifluoromethylbenzyl bromide,
4-trifluoromethylbenzyl chloride,
4-trifluoromethylbenzyl bromide,
4-vinylbenzyl chloride,
chloro-diphenylmethane,
bromo-diphenylmethane,
triphenylmethyl chloride,
triphenylmethyl bromide,
chloro(4-chlorophenyl)-phenylmethane,
chlorobis(4-fluorophenyl)-methane.

The compound (23) as the synthesis material ketones of the compound (eH) is shown below more illustratively;
acetophenone,
propiophenone,
butyrophenone,
isobutyrophenone,
valerophenone,
2,2-dimethylpropiophenone,
4'-methylpropiophenone,
3'-methylacetophenone,
4'-methylacetophenone,
4'-ethylacetophenone,
4'-butylacetophenone,
2'-methoxyacetophenone,
3'-methoxyacetophenone,
3'-(trifluoromethoxy)-acetophenone,
4'-(trifluoromethoxy)-acetophenone,
4'-ethyoxyacetophenone,
2'-nitroacetophenone,
4'-nitroacetophenone,
benzophenone,
2-methylbenzophenone,
3-methylbenzophenone,
4-methylbenzophenone,
4-benzobiphenyl,
2,4-diphenylbenzophenone,
2,5-diphenylbenzophenone,
3,4-diphenylbenzophenone,
3-(trifluoromethyl)-benzophenone,
4-(trifluoromethyl)-benzophenone,
3,3'-bis (trifluoromethyl)-benzophenone,
3,4'-bis (trifluoromethyl)-benzophenone,
4-methoxybenzophenone,
3,3'-dinitrobenzophenone.

In the synthesis of the compound (1) of the invention, purification of a compound of interest from the reaction mixture is carried out by employing usually used techniques in the field of chemical synthesis, namely by effecting separation extraction of the reaction product between water and an organic solvent which does not optionally mixed with water, such as benzene, toluene, ethyl acetate, butyl acetate, methyl isobutyl ketone, chloroform, dichloromethane or the like, and then carrying out concentration, crystallization and the like. Also, as occasion demands, fractional purification may be carried out for example by a column chromatography using alumina, silica gel, adsorption resin or the like.

Being an amine, the compound (I) of the invention exists as a base. In consequence, it forms salts with a number of inorganic and organic acids, and such a property is applied to the production of pure substance and its provisional forms as pharmaceutical preparations. That is, in its production process, acidification of the compound renders possible its solubilization and extraction purification in water or the like polar solvent so that it can be isolated as a salt having desirable physicochemical properties, and, in applying it to pharmaceutical preparations, it can form a pharmacologically acceptable salt. Examples of the salt to be formed include acid addition salts with hydrochloric acid, nitric acid, hydrobromic acid, sulfuric acid, phosphoric acid and the like inorganic acids or with aliphatic monocarboxylic acids, dicarboxylic acids, hydroxyalkanoic acids, hydroxyalkanoic diacids, amino acids and the like, as well as salts derived from aromatic acids, aliphatic and aromatic sulfonic acids and the like nontoxic organic acids. Examples of such acid addition salts include hydrochloride, hydrobromide, nitrate, sulfate, hydrogensulfate, phosphate, monohydrogenphosphate, dihydrogenphosphate, acetate, propionate, tartarate, oxalate, malonate, succinate, fumarate, maleate, mandelate, benzoate, phthalate, methanesulfonate, benzenesulfonate, toluenesulfonate, citrate, lactate, malate, glycolate and the like.

These acid addition salts described above are significant also as pharmacologically acceptable pharmaceutical compositions, and it seems that they have advantages as pharmaceutical compositions in terms of the preparation of medicaments and of the dispersing and absorbing abilities when administered to the human body.

A pharmaceutical composition which contains the compound of the invention as an active ingredient can be administered to human and animals other than human, through the route of either oral administration or parenteral administration (e.g., intravenous injection, intramuscular injection, subcutaneous injection, rectal administration or percutaneous absorption). Thus, the pharmaceutical composition containing the compound of the invention as an active ingredient can be made into appropriate dosage forms depending on each route of administration.

Illustrative examples of dosage forms include tablets, capsules, powders, granules, syrups and the like as oral preparations and intravenous, intramuscular and the like injections, rectal administration preparations, oleaginous suppositories, aqueous suppositories and the like as parenteral preparations.

Each of these various preparations can be produced in the usual way making use of generally used fillers, disintegrators, binders, lubricating agents, coloring agents and the like.

Lactose, glucose, corn starch, sorbitol, crystalline cellulose and the like can be exemplified as the fillers, starch, sodium alginate, gelatin powder, calcium carbonate, calcium citrate, dextrin and the like can be cited as the disintegrators, dimethyl cellulose, polyvinyl alcohol, polyvinyl ether, methyl cellulose, ethyl cellulose, acacia, gelatin, hydroxypropyl cellulose, polyvinyl pyrrolidone and the like can be exemplified as the binders and talc, magnesium stearate, polyethylene glycol, hardened plant oil and the like can be exemplified as the lubricating agents. In addition, the aforementioned injections can be produced by further adding a buffer, a pH adjusting agent, a stabilizing agent and the like as occasion demands.

Though the amount of the compound of the invention in the pharmaceutical composition varies depending on its dosage forms, it may be used in an amount of generally from 0.1 to 50% by weight, preferably from 0.1 to 20% by weight, based on the total camposition. Its dose is optionally decided in each case, taking age, body weight, sex, difference in diseases, degree of symptoms and the like of each patient into consideration, but the dose is within the range of generally from 0.1 to 100 mg, preferably from 0.1 to 30 mg, per day per adult, and the daily dose is administered once a day or by dividing it into several doses per day.

BEST MODE FOR CARRYING OUT THE INVENTION

The invention is described further in detail by the following inventive and test examples, but the invention is not limited thereto. In this connection, the following description "(the inventive compound)" means the compound (1) of the invention and the description "(the inventive intermediate)" means the compound (aQ) or (bQ).

EXAMPLES

1. Synthesis examples of the compound (1) of the invention having group (a) and its production intermediate Synthesis Example 1 (The Inventive Compound) 2a-[4-(2,3,4,9-Tetrahydro-1H-pyrido[3,4-b]indol-2-yl)-butyl]-2a,3,4,5-tetrahydro-1H-benz[cd]indol-2-one A 168 mg (0.98 mmol) portion of 2,3,4,9-tetrahydro-1H-pyrido[3,4-b]indole and 269 mg (1.96 mmol) of potassium carbonate were added to 3 ml of DMF solution containing 150 mg (0.49 mmol) of 2a-(4-bromobutyl)-2a,3,4,5-tetrahydro-1H-benz[cd]indol-2-one and stirred overnight at room temperature. The reaction solution was extracted with chloroform and washed with water. After drying ($Na_2SO_4$), the solvent was removed by evaporation under a reduced pressure and the residue was recrystallized from acetone to obtain 98 mg of the title compound (48% in yield). An oily material obtained by concentrating the mother liquid was purified by a silica gel column chromatography (30 cc; elution by chloroform-methanol=15:1) to obtain 73 mg of the title compound (38% in yield).

$^1$H-NMR ($CD_3OD$): δ 1.07 (1H, m), 1.27 (2H, m), 1.54 (2H, m), 1.87 (3H, m), 2.05 (1H, ddd), 2.19 (1H, m), 2.51 (2H, m), 2.64 (1H, ddd), 2.78–2.90 (5H, m), 3.63 (2H, s), 6.69 (1H, d), 6.79 (1H, d), 6.95 (1H, t), 7.02 (1H, t), 7.11 (1H, t), 7.25 (1H, d), 7.36 (1H, d), 7.85 (1H, s). Mass spectrum TSP m/z 400 (M+H)$^+$.

Synthesis Example 2a (The Inventive Compound) 2a-[3-(2,3,4,9-Tetrahydro-1H-pyrido[3,4-b]indol-2-yl)-propyl]-2a,3,4,5-tetrahydro-1H-benz[cd]indol-2-one By the method described in Synthesis Example 1a, 238 mg (91% in yield) of the title compound was obtained from 200 mg (0.68 mmol) of 2a-(3-bromopropyl)-2a,3,4,5-tetrahydro-1H-benz[cd]indol-2-one and 234 mg (1.36 mmol) of 2,3,4,9-tetrahydro-1H-pyrido[3,4-b]indole.

$^1$H-NMR ($CDCl_3$): δ 1.37 (2H, m)r, 1.61 (3H, m)), 1.88 (3H, m), 2.11 (2H, m), 2.48 (2H, t), 2.63 (1H, m), 2.74 (2H, s), 2.83 (1H, m), 3.51 (2H, s), 6.65 (1H, d), 6.80 (1H, d), 7.08 (3H, m), 7.27 (1H, d), 7.43 (1H, d), 7.61 (1H, br s), 7.78 (1H, br s). Mass spectrum TSP m/z 386 (M+H)$^+$.

Synthesis Example 3a (The Inventive Compound) 2a-[4-(6-Methoxy-2,3,4,9-tetrahydro-1H-prido[3,4-b]indol-2-yl)-butyl]-2a,3,4,5-tetrahydro-1H-benz[cd]indol-2-one A 295 mg (1.46 mmol) portion of 6-methoxy-2,3,4,9-tetrahydro-1H-pyrido[3,4-b]indole and 404 mg (2.91 mmol) of potassium carbonate were added to 7 ml of DMF solution containing 300 mg (0.97 mmol) of 2a-(4-bromobutyl)-2a,3,4,5-tetrahydro-1H-benz[cd]indol-2-one and stirred overnight at room temperature. The reaction solution was extracted with ethyl acetate and washed with water. After drying ($Na_2SO_4$), the solvent was removed by evaporation under a reduced pressure and the thus obtained oil was purified by a silica gel column chromatography (80 cc; elution by chloroform-methanol=15:1) and recrystallized from acetone-diisopropyl ether to obtain 369 mg of the title compound (88% in yield).

$^1$H-NMR ($CD_3OD$): δ 1.06 (1H, m), 1.28 (2H, m), 1.52 (2H, m), 1.86 (3H, m), 2.05 (1H, m), 2.19 (1H, m), 2.50 (2H, m), 2.64 (1H, ddd), 2.75–2.86 (5H, m), 3.60 (2H, s), 3.80 (3H, s), 6.69 (2H, m), 6.79 (1H, d), 6.88 (1H, d), 7.12 (2H, m). Mass spectrum TSP m/z 430 (M+H)$^+$.

Synthesis Example 4a (The Inventive Compound) 2a-[4-(6-Hydroxy-2,3,4,9-tetrahydro-1H-pyrido[3,4-b]indol-2-yl)-butyl]-2a,3,4,5-tetrahydro-1H-benz[cd]indol-2-one A 1.3 ml portion of dichloromethane solution containing 68 mg (0.16 mmol) of 2a-[4-(6-methoxy-2,3,4,9-tetrahydro-1H-pyrido[3,4-b]indol-2-yl)butyl]-2a,3,4,5-tetrahydro-1H-benz[cd]indol-2-one was cooled to 0° C. and mixed with 0.2 ml of dichloramethane solution containing 45 μl (0.48 mmol) of boron tribromide. After 6 hours of stirring at room temperature, the reaction solution was extracted with a solution of chloroform-methanol=5:1 and washed with sodium bicarbonate aqueous solution. After drying ($Na_2SO_4$), the solvent was removed by evaporation under a reduced pressure and the residue was recrystallized from methanol-ethyl acetate to obtain 20 mg of the title compound (30% in yield).

$^1$H-NMR ($CD_3OD$): δ 1.07 (1H, m), 1.29 (2H, m), 1.56 (2H, m), 1.88 (3H, m), 2.05 (1H, ddd), 2.19 (1H, m), 2.59 (2H, m), 2.75 (3H, m), 2.89 (3H, m), 3.69 (2H, s), 6.61 (1H, dd), 6.69 (1H, d), 6.78 (2H, m), 7.10 (2H, m), 7.87 (1H, s). Mass spectrum TSP m/z 416 (M+H)$^+$.

Synthesis Example 5a (The Inventive Compound) 6-Bromo-2a-[4-(2,3,4,9-tetrahydro-1H-pyrido[3,4-b]indol-2-yl)-butyl]-2a,3,4,5-tetrahydro-1H-benz[cd]indol-2-one A 31 mg (0.18 mmol) portion of 2,3,4,9-tetrahydro-1H-pyrido[3,4-b]indole and 62 mg (0.54 mmol) of potassium carbonate were added to 1 ml of DMF solution containing 58 mg (0.15 mmol) of 6-bromo-2a-(4-bromobutyl)-2a,3,4,5-tetrahydro-1H-benz[cd]indol-2-one and stirred overnight at room temperature. The reaction solution was extracted with ethyl acetate and washed with water. After drying ($Na_2SO_4$), the solvent was removed by evaporation under a reduced pressure and the residue was recrystallized from acetone-diisopropyl ether to obtain 50 mg of the title compound (70% in yield).

$^1$H-NMR ($CD_3OD$): δ 1.08 (1H, m), 1.28 (2H, m), 1.54 (2H, m), 1.84–1.95 (3H, m), 2.07 (1H, ddd), 2.21 (1H, m), 2.52 (2H, m), 2.72–2.82 (6H, m), 3.63 (2H, s), 6.64 (1H, d), 6.95 (1H, m), 7.02 (1H, m), 7.25 (1H, d), 7.35 (2H, m). Mass spectrum TSP m/z 478, 480 (M+H)+.

Synthesis Example 6a 2-t-Butoxycarbonyl-9-methyl-2,3,4,9-tetrahydro-1H-pyrido[3,4-b]indole A 66 mg (1.65 mmol) portion of sodium hydride was added to 10 ml of DMF solution containing 300 mg (1.10 mmol) of 2-t-butoxycarbonyl-2,3,4,9-tetrahydro-1H-pyrido[3,4-b]indole and stirred at room temperature for 30 minutes, and then 103 μl (1.65 mmol) of methyl iodide were added thereto and stirred overnight at room temperature. The reaction solution was extracted with ethyl acetate and washed with water. After drying ($Na_2SO_4$), the solvent was removed by evaporation under a reduced pressure and the resulting oil was purified by a silica gel column chromatography (60 cc; elution by ethyl acetate-hexane=1:5) to obtain 200 mg of the title compound (63% in yield).

$^1$H-NMR ($CDCl_3$): δ 1.42 (9H, s), 2.68 (2H, br s), 3.45 (3H, s), 3.70 (2H, br s), 4.50 (2H, br s), 6.98 (1H, m), 7.07 (1H, m), 7.13 (1H, d), 7.36 (1H, d).

Synthesis Example 7a (The Inventive Compound) 2a-[4-(9-Methyl-2,3,4,9-tetrahydro-1H-pyrido[3,4-b]indol-2-yl)-butyl]-2a,3,4,5-tetrahydro-1H-benz[cd]indol-2-one (1) A 1 ml portion of anisole and 0.7 ml of trifluoroacetic acid were added to 7 ml of dichloromethane solution containing 200 mg (0.70 mmol) portion of 2-t-butoxycarbonyl-9-methyl-2,3,4,9-tetrahydro-1H-pyrido[3,4-b]indole and stirred at room temperature for 4 hours. The solvent was removed by evaporation under a reduced pressure and the residue was recrystallized from acetone-diisopropyl ether to obtain 9-methyl-2,3,4,9-tetrahydro-1H-pyrido[3,4-b]indole quantitatively as trifluoroacetate.

(2) A 71 mg (57% in yield) of the title compound was obtained by the method described in Synthesis Example 3a from 80 mg (0.43 mmol) of the 9-methyl-2,3,4,6-tetrahydro-1H-pyrido[3,4-b]indole trifluoroacetate obtained by the above step (1) and 93 mg (0.30 mmol) of 2a-(4-bromobutyl)-2a,3,4,5-tetrahydro-1H-benz[cd]indol-2-one.

$^1$H-NMR ($CDCl_3$): δ 1.11 (1H, m), 1.33 (2H, m), 1.53 (2H, m), 1.84 (3H, m), 2.09 (2H, m), 2.51 (2H, m), 2.62 (1H, ddd), 2.75–2.87 (5H, m), 3.53 (3H, s), 3.60 (2H, s), 6.65 (1H, d), 6.77 (1H, d), 7.02–7.15 (3H, m), 7.22 (1H, d), 7.43 (1H, d), 8.76 (1H, s). Mass spectrum TSP m/z 414 (M+H)+.

Synthesis Example 8a 2-t-Butoxycarbonyl-9-acetyl-2,3,4,9-tetrahydro-1H-pyrido[3,4-b]indole A 245 mg (71% in yield) of the title compound was obtained by the method described in Synthesis Example 6a from 300 mg (1.10 mmol) of 2-t-butoxycarbonyl-2,3,4,9-tetrahydro-1H-pyrido[3,4-b]indole, 53 mg (1.32 mmol) of sodium hydride and 94 μl (1.32 mmol) of acetyl chloride.

$^1$H-NMR ($CDCl_3$): δ 1.50 (9 H. s), 2.74 (5H, br s), 3.74 (2H, br s), 4.89 (2H, br s), 7.27 (3H, m), 7.44 (1H, m).

Synthesis Example 9a (The Inventive Compound) 2a-[4-(9-Acetyl-2,3,4,9-tetrahydro-1H-pyrido[3,4-b]indol-2-yl)-butyl]-2a,3,4,5-tetrahydro-1H-benz[cd]indol-2-one (1) By the method described in Synthesis Example 7a (1), 9-acetyl-2,3,4,9-tetrahydro-1H-pyrido[3,4-b]indole was obtained quantitatively as trifluoroacetate from 244 mg (0.78 mmol) of 2-t-butoxycarbonyl-9-acetyl-2,3,4,9-tetrahydro-1H-pyrido[3,4-b]indole.

(2) By the method described in Synthesis Example 3a, 73 mg (56% in yield) of the title compound was obtained from 80 mg (0.30 mmol) of the 9-acetyl-2,3,4,9-tetrahydro-1H-pyrido[3,4-b]indole trifluoroacetate obtained in the above step (1) and 92 mg (0.37 mmol) of 2a-(4-bromobutyl)-2a,3,4,5-tetrahydro-1H-benz[cd]indol-2-one.

$^1$H-NMR ($CDCl_3$): δ 1.10 (1H, m), 1.34 (2H, m), 1.52 (2H, m), 1.83 (3H, m), 2.10 (2H, m), 2.51 (2H, m), 2.58–2.76 (8H, m), 2.83 (1H, m), 3.88 (2H, br s), 6.67 (1H, d), 6.77 (1H, d), 7.08 (1H, t), 7.24 (2H, m), 7.39 (1H, m), 7.78 (1H, m), 8.55 (1H, s). Mass spectrum TSP m/z 442 (M+H)+.

Synthesis Example 10a 2-t-Butoxycarbonyl-9-benzyl-2,3,4,9-tetrahydro-1H-pyrido[3,4-b]indole By the method described in Synthesis Example 6a, 217 mg (54% in yield) of the title compound was obtained from 300 mg (1.10 mmol) of 2-t-butoxycarbonyl-2,3,4,9-tetrahydro-1H-pyrido[3,4-b]indole, 66 mg (1.65 mmol) of sodium hydride and 197 μl (1.65 mmol) of benzyl bromide.

$^1$H-NMR ($CDCl_3$): δ 1.48 (9H, s), 2.83 (2H, br s), 3.74 (2H, br s), 4.52 (2H, br s), 5.21 (2H, s), 7.01–7.35 (8H, m), 7.52 (1 H, d).

Synthesis Example 11a (The Inventive Compound) 2a-[4-(9-Benzyl-2,3,4,9-tetrahydro-1H-pyrido[3,4-b]indol-2-yl)-butyl]-2a,3,4,5-tetrahydro-1H-benz[cd]indol-2-one (1) By the method described-in Synthesis Example 7a (1), 143 mg (91% in yield) of 9-benzyl-2,3,4,9-tetrahydro-1H-pyrido[3,4-b]indole was obtained as trifluoroacetate from 217 mg (0.60 mmol) of 2-t-butoxycarbonyl-9-benzyl-2,3,4, 9-tetrahydro-1H-pyrido[3,4-b]indole.

(2) By the method described in Synthesis Example 3a, 74 mg (49% in yield) of the title compound was obtained from 100 mg (0.38 mmol) of the 9-benzyl-2,3,4,9-tetrahydro-1H-pyrido[3,4-b]indole trifluoroacetate obtained in the above step (1) and 94 mg (0.30 mmol) of 2a-(4-bromobutyl)-2a, 3,4,5-tetrahydro-1H-benz[cd]indol-2-one.

$^1$H-NMR ($CDCl_3$): δ 1.05 (1H, m), 1.25–1.49 (4H, m), 1.80 (3H, m), 2.07 (2H, m), 2.45 (2H, m), 2.60 (1H, ddd), 2.80 (5H, m), 3.52 (2H, s), 5.16 (2H, s), 6.63 (1H, d), 6.76 (1 H. d), 6.97 (2H, d), 7.07 (2H, m), 7.20 (5H, m), 7.48 (1H, d), 8.41 (1H, s). Mass spectrum TSP m/z 490 (M+H)+.

Synthesis Example 12a (The Inventive Intermediate) 2-t-Butoxycarbonyl-9-dimethylcarbamoyl-2,3,4,9-tetrahydro-1H-pyrido[3,4-b]indole By the method described in Synthesis Example 6a, 434 mg (86% in yield) of the title compound was obtained from 400 mg (1.47 mmol) of 2-t-butoxycarbonyl-2,3,4,9-tetrahydro-1H-pyrido[3,4-b]indole, 70 mg (1.76 mmol) of sodium hydride and 162 μl (1.65 mmol) of N,N-dimethylcarbamoyl chloride.

$^1$H-NMR ($CDCl_3$): δ 1.50 (9H, s), 2.77 (2H, br s), 3.05 (6H, s), 3.77 (2H, br s), 4.70 (2H, br s), 7.15–7.27 (3H, m), 7.45 (1H, d).

Synthesis Example 13a (The Inventive Compound) 2a-[4-(9-Dimethylcarbamoyl-2,3,4,9-tetrahydro-1H-pyrido[3,4-b]indol-2-yl)-butyl]-2a,3,4,5-tetrahydro-1H-benz[cd]indol-2-one (1) A 434 mg (1.26 mmol) portion of 2-t-butoxycarbonyl-9-dimethylcarbamoyl-2,3,4,9-tetrahydro-1H-pyrido[3,4-b]

indole was dissolved in 10 ml of methanol, and the solution was mixed with 1 ml of 10% hydrochloric acid-methanol and stirred overnight. The solvent was removed by evaporation under a reduced pressure and the resulting residue was recrystallized from methanol-ethyl acetate to obtain 291 mg (82% in yield) of 9-dimethylcarbamoyl-2,3,4,9-tetrahydro-1H-pyrido[3,4-b]indole hydrochloride.

(2) By the method described in Synthesis Example 3a, 255 mg (90% in yield) of the title compound was obtained from 220 mg (0.79 mmol) of 9-dimethylcarbamoyl-2,3,4,9-tetrahydro-1H-pyrido[3,4-b]indole hydrochloride obtained in the above step (1) and 186 mg (0.60 mmol) of 2a-(4-bromobutyl)-2a,3,4,5-tetrahydro-1H-benz[cd]indol-2-one.

$^1$H-NMR (CDCl$_3$): δ 1.07 (1H, m), 1.32 (2H, m), 1.50 (2H, m), 1.83 (3H, m), 2.08 (2H, m), 2.48 (2H, m), 2.60 (1H, ddd), 2.75–2.85 (5H, m), 3.01 (6H, s), 3.70 (2H, br s), 6.65 (1H, d), 6.75 (1H, d), 7.06 (2 H. t), 7.10–7.21 (3H, m), 7.41 (1H, d), 8.98 (1H, s). Mass spectrum TSP m/z 471 (M+H)$^+$.

Synthesis Example 14a 2-t-Butoxycarbonyl-9-isopropyl-2,3,4,9-tetrahydro-1H-pyrido[3,4-b]indole By the method described in Synthesis Example 6a, 106 mg (31% in yield) of the title compound was obtained from 300 mg (1.10 mmol) of 2-t-butoxycarbonyl-2,3,4,9-tetrahydro-1H-pyrido[3,4-b]indole, 133 mg (3.30 mmol) of sodium hydride and 124 μl (1.32 mmol) of 2-bromopropane.

$^1$H-NMR (CDCl$_3$): δ 1.50 (9H, s), 1.56 (3H, s), 1.57 (3H, s), 2.79 (2H, br s), 3.73 (2H, br s), 4.54 (1H, m), 4.68 (2H, br s), 7.06 (2H, dt), 7.13 (2H, dt), 7.40 (1H, d), 7.46 (1H, d).

Synthesis Example 15a (The Inventive Compound) 2a-[4-(9-Isopropyl-2,3,4,9-tetrahydro-1H-pyrido[3,4-b]indol-2-yl)-butyl]-2a,3,4,5-tetrahydro-1H-benz[cd]indol-2-one (1) By the method described in Synthesis Example 13a (1), 57 mg (78% in yield) of 9-isopropyl-2,3,4,9-tetrahydro-1H-pyrido[3,4-b]indole hydrochloride was obtained from 106 mg (0.60mmol) of 2-t-butoxycarbonyl-9-isopropyl-2,3,4,9-tetrahydro-1H-pyrido[3,4-b]indole.

(2) By the method described in Synthesis Example 3a, the title compound was quantitatively obtained from 56 mg (0.26 mmol) of the 9-isopropyl-2,3,4,9-tetrahydro-1H-pyrido[3,4-b]indole hydrochloride obtained in the above step (1) and 67 mg (0.22 mmol) of 2a-(4-bromobutyl)-2a,3,4,5-tetrahydro-1H-benz[cd]indol-2-one.

$^1$H-NMR (CDCl$_3$): δ 1.12 (1H, m), 1.34 (2H, m), 1.53 (8H, m), 1.86 (3H, m), 2.10 (2H, m), 2.52 (2H, m), 2.61 (1H, ddd), 2.76 (4H, s), 2.80 (1H, m), 3.66 (2H, s), 4.47 (1H, m), 6.64 (1H, d), 6.76 (1H, d), 7.00–7.11 (3H, m), 7.37 (1H, d), 7.43 (1H, d), 8.75 (1H, s). Mass spectrum TSP m/z 442 (M+H)$^+$.

Synthesis Example 16a 2-t-Butoxycarbonyl-9-methoxycarbonyl-2,3,4,9-tetrahydro-1H-pyrido[3,4-b]indole By the method described in Synthesis Example 6a, 325 mg (67% in yield) of the title compound was obtained from 400 mg (1.47 mmol) of 2-t-butoxycarbonyl-2,3,4,9-tetrahydro-1H-pyrido[3,4-b]indole, 70 mg (1.76 mmol) of sodium hydride and 136 μl (1.76 mmol) of methyl chloroformate.

$^1$H-NMR (CDCl$_3$): δ 1.51 (9H, s), 2.70 (2H, br s), 3.71 (2H, br s), 4.01 (3H, s), 4.80 (2H, s), 7.25 (3H, m), 7.38 (1H, d).

Synthesis Example 17a (The Inventive Compound) 2a-[4-(9-Methoxycarbonyl-2,3,4,9-tetrahydro-1H-pyrido[3,4-b]indol-2-yl)-butyl]-2a,3,4,5-tetrahydro-1H-benz[cd]indol-2-one (1) By the method described in Synthesis Example 7a (1), 321 mg (95% in yield) of 9-methoxycarbonyl-2,3,4,9-tetrahydro-1H-pyrido[3,4-b]indole trifluoroacetate was obtained from 325 mg (0.98 mmol) of 2-t-butoxycarbonyl-9-methoxycarbonyl-2,3,4,9-tetrahydro-1H-pyrido[3,4-b]indole.

(2) By the method described in Synthesis Example 3a, the title compound was obtained quantitatively from 201 mg (0.58 mmol) of the 9-methoxycarbonyl-2,3,4,9-tetrahydro-1H-pyrido[3,4-b]indole trifluoroacetate obtained in the above step (1) and 150 mg (0.49 mmol) of 2a-(4-bromobutyl)-2a,3,4,5-tetrahydro-1H-benz[Cd]indol-2-one.

$^1$H-NMR (CDCl$_3$): δ 1.11 (1H, m), 1.35 (2H, m), 1.53 (2H, m), 1.85 (3H, m), 2.10 (2H, m), 2.52 (2H, m), 2.60–2.84 (6H, m), 3.85 (2H, br s), 4.00 (3H, s), 6.68 (1H, d), 6.78 (1H, d), 7.09 (1H, t), 7.23 (2H, m), 7.37 (1H, dd), 8.07 (1H, d), 8.49 (1H, s). Mass spectrum TSP m/z 458 (M+H)$^+$.

Synthesis Example 18a 2-t-Butoxycarbonyl-9-cyanomethyl-2,3,4,9-tetrahydro-1H-pyrido[3,4-b]indole By the method described in-Synthesis Example 6a, 116 mg (17% in yield) of the title compound was obtained from 600 mg (2.20 mmol) of 2-t-butoxycarbonyl-2,3,4,9-tetrahydro-1H-pyrido[3,4-b]indole, 132 mg (3.30 mmol) of sodium hydride and 230 μl (3.30 mmol) of bromoacetonitrile.

$^1$H-NMR (CDCl$_3$): δ 1.51 (9H, s), 2.77 (2H, br s), 3.74 (2H, br s), 4.63 (2H, s), 4.77 (2H, br s), 7.17 (1H, m), 7.26 (2H, m), 7.49 (1H, d).

Synthesis Example 19a (The Inventive Compound) 2a-[4-(9-Cyanomethyl-2,3,4,9-tetrahydro-1H-pyrido[3,4-b]indol-2-yl)-butyl]-2a,3,4.5-tetrahydro-1H-benz[cd]indol-2-one (1) By the method described in Synthesis Example 7a (1), 9-cyanomethyl-2,3,4,9-tetrahydro-1H-pyrido[3,4-b]indole trifluoroacetate was obtained quantitatively from 115 mg (0.37 mmol) of 2-t-butoxycarbonyl-9-cyanomethyl-2,3,4,9-tetrahydro-1H-pyrido[3,4-b]indole.

(2) By the method described in Synthesis Example 3a, 105 mg (74% in yield) of the title compound was obtained from 125 mg (0.38 mmol) of the 9-cyanomethyl-2,3,4,9-tetrahydro-1H-pyrido[3,4-b]indole trifluoroacetate obtained in the above step (1) and 99 mg (0.32 mmol) of 2a-(4-bromobutyl)-2a,3,4,5-tetrahydro-1H-benz[cd]indol-2-one.

$^1$H-NMR (CDCl$_3$): δ 1.11 (1H, m), 1.34 (2H, m), 1.52 (2H, m), 1.85 (3H, m), 2.11 (2H, m), 2.53 (2H, m), 2.63 (1H, ddd), 2.79 (5H, m), 3.62 (2H, s), 4.79 (2H, s), 6.67 (1H, d), 6.78 (1H, d), 7.09 (1H, t), 7.12–7.26 (3H, m), 7.45 (1H, d), 8.44 (1H, s). Mass spectrum TSP m/z 439 (M+H)$^+$.

Synthesis Example 20a 2-t-Butoxycarbonyl-9-methoxymethyl-2,3,4,9-tetrahydro-1H-pyrido[3,4-b]indole By the method described in Synthesis Example 6a, 419 mg (72% in yield) of the title compound was obtained from 500 mg (1.84 mmol) of 2-t-butoxycarbonyl-2,3,4,9-tetrahydro-1H-pyrido[3,4-b]indole, 110 mg (2.76 mmol) of sodium hydride and 210 μl (2.76 mmol) of chloromethyl methyl ether.

$^1$H-NMR (CDCl$_3$): δ 1.50 (9H, s), 2.78 (2H, br s), 3.24 (3H, s), 3.76 (2H, br s), 4.67 (2H, br s), 5.33 (2H, s), 7.12 (1H, dt), 7.20 (1H, dt), 7.40 (1H, d), 7.47 (1H, d).

Synthesis Example 21a (The Inventive Compound) 2a-[4-(9-Methoxymethyl-2,3,4,9-tetrahydro-1H-pyrido[3,4-b]indol-2-yl)-butyl]-2a,3,4,5-tetrahydro-1H-benz[cd]indol-2-one (1) A 1.8 ml portion of 5 N hydrochloric acid was added to 9 ml of methanol solution containing 395 mg (1.25 mmol)

of 2-t-butoxycarbonyl-9-methoxymethyl-2,3,4,9-tetrahydro-1H-pyrido[3,4-b]indole and allowed to stand at room temperature for 3 days. This was adjusted to pH 8 with 5 N sodium hydroxide solution. Methanol was removed by evaporation under a reduced pressure and the resulting residue was extracted with chloroform. The extract was washed with water, dried ($Na_2SO_4$) and then concentrated under a reduced pressure to obtain 9-methoxymethyl-2,3,4,9-tetrahydro-1H-pyrido[3,4-b]indole quantitatively.

(2) By the method described in Synthesis Example 3a, 141 mg (39% in yield) of the title compound was obtained from 195 mg (0.90 mmol) of the 9-methoxymethyl-2,3,4,9-tetrahydro-1H-pyrido[3,4-b]indole obtained in the above step (1) and 253 mg (0.82 mmol) of 2a-(4-bromobutyl)-2a,3,4,5-tetrahydro-1H-benz[cd]indol-2-one.

$^1$H-NMR ($CDCl_3$): δ 1.11 (1H, m), 1.33 (2H, m), 1.53 (2H, m), 1.84 (3H, m), 2.09 (2H, m), 2.53 (2H, m), 2.77 (1H, ddd), 2.81 (5H, m), 3.19 (3H, s), 3.67 (2H, br s), 5.30 (2H, s), 6.66 (1H, d), 6.77 (1H, d), 7.08 (2H, m), 7.16 (1H, dt), 7.37 (1H, d), 7.43 (1H, d), 8.56 (1H, br d). Mass spectrum TSP m/z 444 (M+H)$^+$.

Synthesis Example 22a (The Inventive Intermediate) 2-t-Butoxycarbonyl-9-carbamoylmethyl-2,3,4,9-tetrahydro-1H-pyrido[3,4-b]indole By the method described in Synthesis Example 6a, 384 mg (63% in yield) of the title compound was obtained from 500 mg (1.84 mmol) of 2-t-butoxycarbonyl-2,3,4,9-tetrahydro-1H-pyrido[3,4-b]indole, 110 mg (2.76 mmol) of sodium hydride and 380 mg (2.76 mmol) of bromoacetamide.

$^1$H-NMR ($CDCl_3$): δ 1.49 (9H, s), 2.75 (2H, br s), 3.72 (2H, br s), 4.54 (4H, s), 5.69 (1H, br s), 6.58 (1H, br s), 7.09–7.21 (3H, m), 7.45 (1H, d).

Synthesis Example 23a (The Inventive Compound) 2a-[4-(9-Carbamoylmethyl-2,3,4,9-tetrahydro-1H-pyrido[3,4-b]indol-2-yl)-butyl]-2a,3,4,5-tetrahydro-1H-benz[cd]indol-2-one (1) By the method described in Synthesis Example 7a (1), 362 mg (91% in yield) of 9-carbamoylmethyl-2,3,4,9-tetrahydro-1H-pyrido[3,4-b]indole trifluoroacetate from 384 mg (1.16 mmol) of 2-t-butoxycarbonyl-9-carbamoylmethyl-2,3,4,9-tetrahydro-1H-pyrido[3,4-b]indole.

(2) By the method described in Synthesis Example 3a, 202 mg (91% in yield) of the title compound was obtained from 200 mg (0.58 mmol) of the 9-carbamoylmethyl-2,3,4,9-tetrahydro-1H-pyrido[3,4-b]indole trifluoroacetate obtained in the above step (1) and 150 mg (0.49 mmol) of 2a-(4-bromobutyl)-2a,3,4,5-tetrahydro-1H-benz[cd]indol-2-one.

$^1$H-NMR ($CDCl_3$): δ 1.08 (1H, m), 1.29 (2H, m), 1.46 (2H, m), 1.82 (3H, m), 2.06 (2H, m), 2.48 (2H, t), 2.61 (1H, ddd), 2.80 (5H, m), 3.52 (2H, s), 4.58 (2H, s), 5.58 (1H, br s), 6.52 (1H, br s), 6.65 (1H, d), 6.76 (1H, d), 7.05–7.20 (4H, m), 7.44 (1H, d), 9.04 (1H, s). Mass spectrum TSP m/z 457 (M+H)$^+$.

Synthesis Example 24a (The Inventive Intermediate) 2-t-Butoxycarbonyl-9-diethylcarbamoyl-2,3,4,9-tetrahydro-1H-pyrido[3,4-b]indole By the method described in Synthesis Example 6a, 639 mg (78% in yield) of the title compound was obtained from 600 mg (2.20 mmol) of 2-t-butoxycarbonyl-2,3,4,9-tetrahydro-1H-pyrido[3,4-b]indole, 132 mg (3.30 mmol) of sodium hydride and 419 μl (3.30 mmol) of N,N-diethylcarbamoyl chloride.

$^1$H-NMR ($CDCl_3$): δ 1.20 (6H, t), 1.48 (9H, s), 2.77 (2H, br s), 3.44 (4H, m), 3.77 (2H, br s), 4.67 (2H, s), 7.14–7.29 (3H, m), 7.45 (1H, d).

Synthesis Example 25a (The Inventive Compound) 2a-[4-(9-Diethylcarbamoyl-2,3,4,9-tetrahydro-1H-pyrido[3,4-b]indol-2-yl)-butyl]-2a,3,4,5-tetrahydro-1H-benz[cd]indol-2-one (1) By the method described in Synthesis Example 7a (1), 522 mg (79% in yield) of 9-diethylcarbamoyl-2,3,4,9-tetrahydro-1H-pyrido[3,4-b]indole trifluoroacetate was obtained from 639 mg (1.72 mmol) of 2-t-butoxycarbonyl-9-diethylcarbamoyl-2,3,4,9-tetrahydro-1H-pyrido[3,4-b]indole.

(2) By the method described in Synthesis Example 3a, 216 mg (88% in yield) of the title compound was obtained from 228 mg (0.59 mmol) of the 9-diethylcarbamoyl-2,3,4,9-tetrahydro-1H-pyrido[3,4-b]indole trifluoroacetate obtained in the above step (1) and 152 mg (0.49 mmol) of 2a-(4-bromobutyl)-2a,3,4,5-tetrahydro-1H-benz[cd]indol-2-one.

$^1$H-NMR ($CDCl_3$): δ 1.14 (1H, m), 1.18 (6H, t), 1.35 (2H, m), 1.52 (2H, m), 1.84 (3H, m), 2.10 (2H, m), 2.51 (2H, m), 2.65 (1H, ddd), 2.79 (5H, m), 3.39 (2H, m), 3.52 (2H, m), 3.67 (2H, s), 6.65 (1H, d), 6.78 (1H, d), 7.09 (1H, t), 7.11–7.24 (3H, m), 7.43 (1H, dd), 8.11 (1H, s). FAB-MS m/z 499 (M+H)$^+$.

Synthesis Example 26a (The Inventive Intermediate) 2-t-Butoxycarbonyl-9-carbamoyl-2,3,4,9-tetrahydro-1H-pyrido[3,4-b]indole A 10 ml portion of tetrahydrofuran (THF) solution containing 600 mg (2.20 mmol) of 2-t-butoxycarbonyl-2,3,4,9-tetrahydro-1H-pyrido[3,4-b]indole was cooled to −78° C., mixed with 4.13 ml (6.60 mmol) of 1.6 M n-butyl lithium hexane solution and stirred for 30 minutes, while temperature of the reaction solution increased to −45° C. This was mixed with 6 ml of THF solution containing 1.31 g (4.40 mmol) of triphosgene and stirred for 3.5 hours, while temperature of the reaction solution increased to 0° C. After additional 2 hours of stirring at room temperature, the reaction solution was again cooled to −30° C. This was mixed with 20 ml of 28% ammonia aqueous solution, stirred for 30 minutes and then extracted with chloroform. The extract was washed with water, hydrochloric acid in that order and dried ($Na_2SO_4$), and then the solvent was removed by evaporation under a reduced pressure and the resulting oily material was purified by a silica gel column chromatography (140 cc; elution by ethyl acetate-hexane=2:5) to obtain 469 mg of the title compound (68% in yield).

$^1$H-NMR ($CDCl_3$): δ 1.50 (9H, s), 2.75 (2H, br s), 3.75 (2H, br s), 4.87 (2H, br s), 5.75 (2H, br s), 7.26 (2H, m), 7.47 (1H, br d), 7.74 (1H, br d).

Synthesis Example 27a (The Inventive Compound) 2a-[4-(9-Carbamoyl-2,3,49-tetrahydro-1H-pyrido[3,4-b]indol-2-yl)-butyl]-2a,3,4,5-tetrahydro-1H-benz[cd]indol-2-one (1) By the method described in Synthesis Example 7a (1), 394 mg (96% in yield) of 9-carbamoyl-2,3,4,9-tetrahydro-1H-pyrido[3,4-b]indole trifluoroacetate was obtained from 395 mg (1.25 mmol) of 2-t-butoxycarbonyl-9-carbamoyl-2,3,4,9-tetrahydro-1H-pyrido[3,4-b]indole. EI-MS m/x 215 (M)⁺.

(2) A 1.8 ml portion of DMF solution containing 83 mg (0.25 mmol) of the 9-carbamoyl-2,3,4,9-tetrahydro-1H-pyrido[3,4-b]indole trifluoroacetate obtained in the above step (1) and 78 mg (0.25 mmol) of 2a-(4-bromobutyl)-2a,3,4,5-tetrahydro-1H-benz[cd]indol-2-one was mixed with 132 μl (0.75 mmol) of diisopropylethylamine and stirred at room temperature for 2 days. The reaction solution was extracted with ethyl acetate, and the extract was washed with water. After drying ($Na_2SO_4$), the solvent was removed by evaporation under a reduced pressure and the thus obtained oily material was purified by a silica gel column chromatography (80 cc; elution by chloroform-methanol=30:1) and further recrystallized from acetone-ethyl acetate to obtain 108 mg (96% in yield) of the title compound.

¹H-NMR ($CD_3OD$): δ 1.06 (1H, m), 1.27 (2H, m), 1.53 (2H, m), 1.85 (3H, m), 2.05 (1H, ddd), 2.16 (1H, m), 2.51 (2H, m), 2.63 (1H, ddd), 2.75–2.86 (5H, m), 3.83 (2H, br s), 6.69 (1H, d), 6.78 (1H, d), 7.10 (1H, t), 7.16 (1H, dt), 7.23 (1H, dt), 7.42 (1H, d), 7.78 (1H, d). Mass spectrum TSP m/z 443 (M+H)⁺.

Synthesis Example 28a (The Inventive Intermediate) 2-t-Butoxycarbonyl-9-methylcarbamoyl-2,3,4,9-tetrahydro-1H-pyrido[3,4-b]indole This was synthesized by the same method of Synthesis Example 26a, except that methylamine aqueous solution was used instead of the 20 ml of 28% ammonia aqueous solution (66% in yield).

¹H-NMR ($CDCl_3$): δ 1.49 (9H, s), 2.71 (2H, br t), 3.06 (3H, br s), 3.71 (2H, br t), 4.82 (2H, s), 5.81 (1H, br s), 7.21 (2H, m), 7.43 (1H, d), 7.61 (1H, br d).

Synthesis Example 29a (The Inventive Compound) 2a-[4-(9-Methylcarbamoyl-2,3,4,9-tetrahydro-1H-pyrido[3,4-b]indol-2-yl)-butyl]-2a,3,4,5-tetrahydro-1H-benz[cd]indol-2-one (1) By the method described in Synthesis Example 7a (1), 417 mg (83% in yield) of 9-methylcarbamoyl-2,3,4,9-tetrahydro-1H-pyrido[3,4-b]indole trifluoroacetate was obtained from 480 mg (1.46 mmol) of 2-t-butoxycarbonyl-9-methylcarbamoyl-2,3,4,9-tetrahydro-1H-pyrido[3,4-b]indole.

Mass spectrum TSP m/z 230 (M+H)⁺.

(2) By the method described in Synthesis Example 27a (2), 480 mg (66% in yield) of the title compound was obtained from 300 mg (0.87 mmol) of the 9-methylcarbamoyl-2,3,4,9-tetrahydro-1H-pyrido[3,4-b]indole trifluoroacetate obtained in the above step (1) and 269 mg (0.87 mmol) of 2a-(4-bromobutyl)-2a,3,4,5-tetrahydro-1H-benz[cd]indol-2-one.

¹H-NMR ($CD_3OD$): δ 1.05 (1H, m), 1.26 (2H, m), 1.52 (2H, m), 1.85 (3H, m), 2.04 (1H, ddd), 2.17 (1H, m), 2.51 (2H, m), 2.63 (1H, ddd), 2.75–2.86 (5H, m), 2.97 (3H, s), 3.79 (2H, br s), 6.69 (1H, d), 6.78 (1H, d), 7.10 (1H, t), 7.15 (1H, dt), 7.22 (1H, dt), 7.42 (1H, d), 7.68 (1H, d). Mass spectrum TSP m/z 457 (M+H)⁺.

Synthesis Example 30a (The Inventive Compound) 2a-[4-(3,4-Dihydro-1H-benzo[4,5]thieno[2,3-c]pyridin-2-yl)-butyl]-2a,3,4,5-tetrahydro-1H-benz[cd]indol-2-one By the method described in Synthesis Example 3a, the title compound was obtained quantitatively from 309 mg (1.00 mmol) of 2a-(4-bromobutyl)-2a,3,4,5-tetrahydro-1H-benz[cd]indol-2-one and 249 mg (1.10 mmol) of 3,4-dihydro-1H-benzo[4,5]thieno[2,3-c]pyridine hydrochloride.

¹H-NMR ($CDCl_3$): δ 1.11 (1H, m), 1.34 (2H, m), 1.50 (2H, m), 1.84 (3H, m), 2.10 (2H, m), 2.48 (2H, m), 2.62 (1H, ddd), 2.80 (4H, s), 2.82 (1H, m), 3.67 (2H, s), 6.67 (1H, d), 6.77 (1H, d), 7.09 (1H, t), 7.28 (2H, m), 7.53 (1H, d), 7.74 (1H, d), 8.41 (1H, s). Mass spectrum TSP m/z 417 (M+H)⁺.

Synthesis Example 31a 2-t-Butoxycarbonyl-3,4-dihydro-1H-benzo[4,5]thieno[2,3-c]pyridine A 2.00 g (8.86 mmol) portion of 3,4-dihydro-1H-benzo[4,5]thieno[2,3-c]pyridine hydrochloride was dissolved in a mixed solvent of 70 ml chloroform and 10 ml methanol, and the solution was mixed with 3.67 g (26.58 mmol) of potassium carbonate and cooled to 0° C. This was mixed with 2.24 ml (9.75 mmol) of di-t-butyl bicarbonate and stirred overnight at room temperature. The reaction solution was poured into ice-cooled water and extracted with chloroform. The extract was washed with water and dried ($Na_2SO_4$), and then the solvent was removed by evaporation under a reduced pressure and the thus obtained oily material was purified by a silica gel column chromatography (250 cc; elution by ethyl acetate-hexane=1:6) to obtain 2.04 g of the title compound (80% in yield).

¹H-NMR ($CDCl_3$): δ 1.50 (9H, s), 2.82 (2H, br s), 3.78 (2H, br s), 4.70 (2H, br s), 7.31 (2H, m), 7.57 (1H, d), 7.77 (1H, d).

Synthesis Example 32a (The Inventive Intermediate) 2-t-Butoxycarbonyl-3,4-dihydro-9-oxo-9-$\lambda^4$-1H-benzo[4,5]thieno[2,3-c]pyridine A 1.83 g (6.32 mmol) portion of 2-t-butoxycarbonyl-3,4-dihydro-1H-benzo[4,5]thieno[2,3-c]pyridine was dissolved in 90 ml of methanol and 18 ml of water, and the solution was cooled to 0° C. and mixed with 6.55 ml (12.64 mmol) of 24% titanium trichloride aqueous solution. At 0° C., to this was added dropwise a solution prepared by adding 5.02 ml of 30% hydrogen peroxide aqueous solution to 14 ml of methanol, and the mixture was stirred at room temperature for 2 hours. The reaction solution was mixed with excess water and extracted with chloroform. The extract was washed with water and dried ($Na_2SO_4$), and then the solvent was removed by evaporation under a reduced pressure and the thus obtained oily material was purified by a silica gel column chromatography (250 cc; elution by ethyl acetate-hexane=3:1) to obtain 1.74 g of the title compound (90% in yield).

¹H-NMR ($CDCl_3$): δ 1.50 (9H, s), 2.66 (2H, br s), 3.51 (1H, br s), 3.95 (1H, br s), 4.40 (1H, br s), 4.72 (1H, br d), 7.35 (1H, d), 7.44 (1H, t), 7.53 (1H, t), 7.87 (1H, d). FAB-MS m/z 306 (M+H)⁺. IR (cm⁻¹): 1040, 1060 (S=O).

Synthesis Example 33a (The Inventive Compound) 2a-[4-(3,4-Dihydro-9-oxo-9-$\lambda^4$-1H-benzo[4,5]thieno[2,3-c]pyridin-2-yl)-butyl]-2a,3,4,5-tetrahydro-1H-benz[cd]indol-2-one (1) By the method described in Synthesis Example 7a (1), 1.09 g (88% in yield) of 3,4-dihydro-9-oxo-9-$\lambda^4$-1H-benzo[4,5]thieno[2,3-c]pyridine trifluoroacetate was obtained from 1.19 g (3.89 mmol) of 2-t-butoxycarbonyl-3,4-dihydro-9-oxo-9-$\lambda^4$-1H-benzo[4,5]thieno[2,3-c]pyridine.

Mass spectrum TSP m/z 206 (M+H)⁺.

(2) By the method described in Synthesis Example 3a, 61 mg (54% in yield) of the title compound was obtained from 99 mg (0.31 mmol) of the 3,4-dihydro-9-oxo-9-$\lambda^4$-1H-benzo[4,5]thieno[2,3-c]pyridine trifluoroacetate obtained in the above step (1) and 80 mg (0.26 mmol) of 2a-(4-bromobutyl)-2a,3,4,5-tetrahydro-1H-benz[cd]indol-2-one.

$^1$H-NMR (CDCl$_3$): δ 1.13 (1H, m), 1.34 (2H, m), 1.46 (2H, m), 1.83 (3H, m), 2.11 (2H, m), 2.49 (2H, m), 2.59–2.84 (6H, m), 3.44 (1H, m), 3.66 (1H, m), 6.68 (1H, dd), 6.77 (1H, d), 7.09 (1H, m), 7.29 (1H, d), 7.39 (1H, t), 7.48 (1H, t), 7.86 (1H, d), 8.46 (1H, d). Mass spectrum TSP m/z 433 (M+H)$^+$.

Synthesis Example 34a (The Inventive Intermediate) 2-t-Butoxycarbonyl-3,4-dihydro-9,9-dioxo-9-$\lambda^6$-1H-benzo[4,5]thieno[2,3-c]pyridine A 42 mg (0.24 mmol) portion of m-chloroperbenzoic acid was added to 2 ml of dichloromethane solution containing 62 mg (0.20 mmol) of 2-t-butoxycarbonyl-3,4-dihydro-9-oxo-9-$\lambda^4$-1H-benzo[4,5]thieno[2,3-c]pyridine and stirred at 0° C. for 2 hours. The reaction solution was mixed with excess water and extracted with chloroform, and the extract was washed with sodium thiosulfate aqueous solution and sodium bicarbonate aqueous solution in that order. After drying (Na$_2$SO$_4$), the solvent was removed by evaporation under a reduced pressure to obtain the title compound quantitatively.

$^1$H-NMR (CDCl$_3$): δ 1.50 (9H, s), 2.64 (2H, br s), 3.72 (2H, br t), 4.43 (2H, br s), 7.33 (1H, d), 7.51 (1H, t), 7.59 (1H, t), 7.72 (1H, d). Mass spectrum TSP (positive) m/z 339 (M+NH$_4$)$^+$, (negative) m/z 321 (M)$^-$.

Synthesis Example 35a (The Inventive Compound) 2a-[4-(3,4-Dihydro-9,9-dioxo-9-$\lambda^6$-1H-benzo[4,5]thieno[2,3-c]pyridin-2-yl)-butyl]-2a,3,4,5-tetrahydro-1H-benz[cd]indol-2-one (1) By the method described in Synthesis Example 7a (1), 532 mg (86% in yield) of 3,4-dihydro-9,9-dioxo-9-$\lambda^6$-1H-benzo[4,5]thieno[2,3-c]pyridine trifluoroacetate was obtained from 595 mg (1.85 mmol) of 2-t-butoxycarbonyl-3,4-dihydro-9,9-dioxo-9-$\lambda^6$-1H-benzo[4,5]thieno[2,3-c]pyridine. Mass spectrum TSP m/z 222 (M+H)$^+$.

(2) By the method described in Synthesis Example 3a, 105 mg (36% in yield) of the title compound was obtained from 261 mg (0.78 mmol) of the 3,4-dihydro-9,9-dioxo-9-$\lambda^6$-1H-benzo[4,5]thieno[2,3-c]pyridine trifluoroacetate obtained in the above step (1) and 200 mg (0.56 mmol) of 2a-(4-bromobutyl)-2a,3,4,5-tetrahydro-1H-benz[cd]indol-2-one.

$^1$H-NMR (CDCl$_3$): δ 1.11 (1H, m), 1.30–1.47 (4H, m), 1.83 (3H, m), 2.11 (2H, m), 2.46 (2H, m), 2.56 (2H, m), 2.63 (1H, ddd), 2.71 (2H, m), 2.82 (1H, m), 3.39 (2H, br d), 6.71 (1H, d), 6.78 (1H, d), 7.09 (1H, t), 7.26 (1H, d), 7.45 (1H, t), 7.53 (1H, t), 7.68 (1H, d), 8.57 (1H, s). Mass spectrum TSP m/z 449 (M+H)$^+$.

Synthesis Example 36a (The Inventive Compound) 2a-[4-(3,4-Dihydro-1H-benzo[4,5]furo[2,3-c]pyridin-2-yl)-butyl]-2a,3,4,5-tetrahydro-1H-benz[cd]indol-2-one By the method described in Synthesis Example 3a, 160 mg (56% in yield) of the title compound was obtained from 147 mg (0.85 mmol) of 3,4-dihydro-1H-benzo[4,5]furo[2,3-c]pyridine and 218 mg (0.71 mmol) of 2a-(4-bromobutyl)-2a,3,4,5-tetrahydro-1H-benz[cd]indol-2-one.

$^1$H-NMR (CDCl$_3$): δ 1.11 (1H, m), 1.34 (2H, m), 1.49 (2H, m), 1.83 (3H, m), 2.09 (2H, m), 2.48 (2H, m), 2.62 (3H, m), 2.74 (2H, t), 2.81 (1H, m), 3.57 (2H, s), 6.67 (1H, d), 6.76 (1H, d), 7.07 (1H, t), 7.17 (2H, m), 7.37 (2H, m), 8.90 (1H, br s). EI-MS m/z 400 (M)$^+$.

Synthesis Example 37a 2-t-Butoxycarbonyl-9-methoxycarbonylmethyl-2,3,4,9-tetrahydro-1H-pyrido[3,4-b]indole A 218 mg (5.45 mmol) portion of sodium hydride was added to 12 ml of DMF solution containing 0.99 g (3.64 mmol) of 2-t-butoxycarbonyl-2,3,4,9-tetrahydro-1H-pyrido[3,4-b]indole, and the mixture was stirred at room temperature for 30 minutes, mixed with 0.52 ml (5.45 mmol) of methyl bromoacetate and again stirred overnight at room temperature. The reaction solution was extracted with ethyl acetate and washed with water. After drying (Na$_2$SO$_4$), the solvent was removed by evaporation under a reduced pressure and the thus obtained oily material was purified by a silica gel column chromatography (200 cc; elution by ethyl acetate-hexane=1:3) to obtain 0.96 g of the title compound (77% in yield).

$^1$H-NMR (CDCl$_3$): δ 1.50 (9H, s), 2.79 (2H, br s), 3.72 (3H, s), 3.74 (2H, br s), 4.56 (2H, s), 4.68 (2H, s), 7.08–7.18 (3H, m), 7.48 (1H, d).

Synthesis Example 38a (The Inventive Compound) 2a-[4-(9-Methoxycarbonylmethyl-2,3,4,9-tetrahydro-1H-pyrido[3,4-b]indol-2-yl)-butyl]-2a3,4,5-tetrahydro-1H-benz[cd]indol-2-one (1) A 10 ml portion of dichloromethane solution containing 344 mg (1.00 mmol) of 2-t-butoxycarbonyl-9-methoxycarbonylmethyl-2,3,4,9-tetrahydro-1H-pyrido[3,4-b]indole was mixed with 1 ml of anisole and 1 ml of trifluoroacetic acid and stirred at room temperature for 4 hours. The solvent was removed by evaporation under a reduced pressure, and the resulting residue was precipitated by adding acetone and diisopropyl ether, thereby obtaining 9-methoxycarbonylmethyl-2,3,4,9-tetrahydro-1H-pyrido[3,4-b]indole quantitatively as trifluoroacetate.

(2) A 0.30 ml (2.13 mmol) portion of triethylamine was added to 7 ml of DMF solution containing 236 mg (0.71 mmol) of the 9-methoxycarbonylmethyl-2,3,4,9-tetrahydro-1H-pyrido[3,4-b]indole trifluoroacetate obtained in the above step (1) and 200 mg (0.65 mmol) of 2a-(4-bromobutyl)-2a,3,4,5-tetrahydro-1H-benz[cd]indol-2-one, and the mixture was stirred at room temperature for 2 days. The reaction solution was extracted with ethyl acetate and washed with water. After drying (Na$_2$SO$_4$), the solvent was removed by evaporation under a reduced pressure and the thus obtained oily material was purified by a silica gel column chromatography (60 cc; elution by chloroform-methanol=40:1) and further recrystallized from acetone-diisopropyl ether to obtain 197 mg of the title compound (64% in yield).

$^1$H-NMR (CDCl$_3$): δ 1.11 (1H, m), 1.34 (2H, m), 1.48 (2H, m), 1.85 (3H, m), 2.12 (2H, m), 2.51 (2H, m), 2.62 (1H, ddd), 2.82 (5H, m), 3.56 (2H, s), 3.69 (3H, s), 4.66 (2H, s), 6.64 (1H, d), 6.77 (1H, d), 7.06–7.17 (4H, m), 7.44 (1H, d), 8.61 (1H, s). Mass spectrum TSP m/z 472 (M+H)$^+$.

Synthesis Example 39a (The Inventive Intermediate) 2-t-Butoxycarbonyl-9-methylcarbamoylmethyl-2,3,4,9-tetrahydro-1H-pyrido[3,4-b]indole A 10 ml portion of tetrahydrofuran solution containing 0.62 g (1.80 mmol) of 2-t-butoxycarbonyl-9- methoxycarbonylmethyl-2,3,4,9-tetrahydro-1H-pyrido[3,4-b]indole was mixed with 2 ml of aqueous solution containing 0.22 g (5.40 mmol) of sodium hydroxide and stirred overnight at room temperature. This was acidified by adding 1 N hydrochloric acid and extracted with chloroform. The extract was washed with water and dried ($Na_2SO_4$), and then the solvent was removed by evaporation under a reduced pressure. The thus obtained residue was dissolved in 12 ml of acetonitrile, and the solution was mixed with 557 mg (2.70 mmol) of N,N-dicyclohexylcarbodiimide and 365 mg (2.70 mmol) of 1-hydroxybenzotriazole and stirred at room temperature for 2 hours. The reaction solution was cooled to 0° C., mixed with 2 ml of 40% methylamine aqueous solution and again stirred at room temperature for 30 minutes. The insoluble matter was removed by filtration, the solvent was removed by evaporation under a reduced pressure and then the resulting residue was purified by a silica gel column chromatography (130 cc; elution by chloroform-methanol=30:1) to obtain 542 mg of the title compound (88% in yield).

$^1$H-NMR ($CDCl_3$): δ 1.50 (9H, s), 2.70 (2H, d), 2.80 (2H, br t), 3.76 (2H, br t), 4.54 (2H, s), 4.58 (2H, s), 5.66 (1H, br s), 7.17 (3H, m), 7.50 (1H, d).

Synthesis Example 40a (The Inventive Compound) 2a-[4-(9-Methylcarbamoylmethyl-2,3,4,9-tetrahydro-1H-pyrido[3,4-b]indol-2-yl)-butyl]-2a,3,4,5-tetrahydro-1H-benz[cd]indol-2-one (1) A 10 ml portion of dichloromethane solution containing 541 mg (1.58 mmol) of 2-t-butoxycarbonyl-9-methylcarbamoylmethyl-2,3,4,9-tetrahydro-1H-pyrido[3,4-b]indole was mixed with 1 ml of anisole and 1 ml of trifluoroacetic acid and stirred overnight at room temperature. The solvent was removed by evaporation under a reduced pressure, and the resulting residue was precipitated by adding acetone and diisopropyl ether, thereby obtaining 465 mg (89% in yield) of 9-methylcarbamoylmethyl-2,3,4,9-tetrahydro-1H-pyrido[3,4-b]indole as trifluoroacetate.

(2) A 415 mg (3.00 mmol) portion of potassium carbonate was added to 6 ml of DMF solution containing 330 mg (1.00 mmol) of the 9-methylcarbamoylmethyl-2,3,4,9-tetrahydro-1H-pyrido[3,4-b]indole trifluoroacetate obtained in the above step (1) and 308 mg (1.00 mmol) of 2a-(4-bromobutyl)-2a,3,4,5-tetrahydro-1H-benz[cd]indol-2-one, and the mixture was stirred at room temperature for 4 days. The reaction solution was extracted with ethyl acetate and washed with water. After drying ($Na_2SO_4$), the solvent was removed by evaporation under a reduced pressure and the thus obtained oily material was purified by a silica gel column chromatography (100 cc; elution by chloroform-methanol=30:1) to obtain 399 mg of the title compound (85% in yield).

$^1$H-NMR ($CDCl_3$): δ 1.14 (1H, m), 1.33 (2H, m), 1.51 (2H, m), 1.86 (3H, m), 2.11 (2H, m), 2.52 (2H, m), 2.64 (1H, m), 2.69 (3H, d), 2.82 (5H, m), 3.52 (2H, s), 4.60 (2H, s), 5.50 (1H, q), 6.67 (1H, d), 6.79 (1H, d), 7.09–7.20 (4H, m), 7.49 (1H, d), 8.13 (1H, s). Mass spectrum TSP m/z 471 $(M+H)^+$.

Synthesis Example 41a (The Inventive Intermediate) 2-t-Butoxycarbonyl-9-dimethylcarbamoylmethyl-2,3,4,9-tetrahydro-1H-pyrido[3,4-b]indole (1) Methanol (100 ml) and sodium hydroxide solution (1 N, 22 mmol) were added to 2-t-butoxycarbonyl-9-methoxycarbonylmethyl-2,3,4,9-tetrahydro-1H-pyrido[3,4-b]indole (7.42 g, 21.5 mmol) and stirred at room temperature for 2 hours, the solvent was removed by evaporation under a reduced pressure, the thus obtained oily material was dissolved in ethyl acetate (100 ml) and then the ethyl acetate layer was washed with water, dried with anhydrous sodium sulfate and concentrated under a reduced pressure. The resulting residue was precipitated by adding diisopropyl ether (30 ml), thereby obtaining 5.29 g (16.0 mmol, 74.4% in yield) of 2-t-butoxycarbonyl-9-carboxymethyl-2,3,4,9-tetrahydro-1H-pyrido[3,4-b]indole.

(2) The 2-t-butoxycarbonyl-9-carboxymethyl-2,3,4,9-tetrahydro-1H-pyrido[3,4-b]indole (1.65 g, 5.0 mmol) obtained in the above step (1) was dissolved in methylene chloride (30 ml), and the solution was mixed with carbonyldiimidazole (0.81 g, 5.0 mmol), stirred at room temperature for 30 minutes, mixed with 2 M dimethylamine-THF solution (3 ml, 6.0 mmol) and further subjected to 1 hour of the reaction. The reaction solution was concentrated, the resulting residue was dissolved in ethyl acetate (50 ml), washed with water and dried with anhydrous sodium sulfate, and then the solvent was removed by evaporation under a reduced pressure. By adding diisopropyl ether (30 ml) to the resulting residue, 1.71 g of the thus precipitated title compound (4.8 mmol, 96% in yield) was obtained as crystals.

Mass spectrum EIMS m/z 357 $(M)^+$; $^1$H-NMR ($CDCl_3$): δ 1.50 (9H, s), 2.81 (2H, br s), 3.00 (3H, s), 3.11 (3H, s), 3.76 (2H, s), 4.55 (2H, s), 4.77 (2H, s), 7.09 (1H, m), 7.16 (2H, d), 7.48 (1H, d).

Synthesis Example 42a (The Inventive Compound) 2a-(4-(9-Dimethylcarbamoylmethyl-2,3,4,9-tetrahydro-1H-pyrido[3,4-b]indol-2-yl)-butyl)-2a,3,4,5-tetrahydro-1H-benz[cd]indol-2-one (1) Dichloromethane solution (20 ml) of 2-t-butoxycarbonyl-9-dimethylcarbamoylmethyl-2,3,4,9-tetrahydro-1H-pyrido[3,4-b]indole (1.43 g, 4.0 mmol) was mixed with anisole (2 ml) and trifluoroacetic acid (3 ml) and stirred at room temperature for 18 hours. The solvent was removed by evaporation under a reduced pressure, and the resulting residue was precipitated by adding acetone (2 ml) and diisopropyl ether (20 ml), thereby obtaining trifluoroacetic acid salt of 9-dimethylcarbamoylmethyl-2,3,4,9-tetrahydro-1H-pyrido[3,4-b]indole. Yield 1.50 g (4.0 mmol), 100%.

(2) The 9-dimethylcarbamoylmethyl-2,3,4,9-tetrahydro-1H-pyrido[3,4-b]indole trifluoroacetate (742 mg, 2.0 mmol) obtained in the above step (1) and 616 mg (2.0 mmol) of 2a-(4-bromobutyl)-2a,3,4,5-tetrahydro-1H-benz[cd]indol-2-one were dissolved in DMF (20 ml), and the solution was mixed with 828 mg (6.0 mmol) of anhydrous potassium carbonate and stirred at room temperature for 2 days. Ethyl acetate (50 ml) and water (50 ml) were added to the reaction solution, and the thus precipitated crystals were collected by filtration to obtain 675 mg of the title compound (1.43 mmol, 72% in yield).

EIMS m/z 484 $(M)^+$; $^1$H-NMR ($CDCl_3$): δ 1.08 (1H, m), 1.26–1.35 (2H, m), 1.50 (2H, m), 1.82–1.86 (3H, m), 2.05–2.15 (2H, m), 2.51 (2H, t), 2.59 (1H, m), 2.77 (3H, s), 2.81 (1H, m), 2.88 (1H, s), 2.98 (3H, s), 3.09 (3H, s), 3.53 (2H, s), 4.75 (2H, s), 6.66 (1H, d), 6.76 (1H, d), 7.02–7.15 (4H, m), 7.43 (1H, d), 9.11 (1H, br s).

Synthesis Example 43a 2-t-Butoxycarbonyl-9-(2-acetoxy-ethyl)-2,3,4,9-tetrahydro-1H-pyrido[3,4-b]indole Anhydrous DMF solution (10 ml) of 2-t-butoxycarbonyl-2,3,4,9-tetrahydro-1H-pyrido[3,4-b]indole (2.72 g, 10 mol)

was mixed with 60% sodium hydride (0.4 g, 10 mmol) and stirred at room temperature for 1 hour. The reaction solution was cooled to −60° C., mixed with 2-acetoxy-1-bromoethane (1.67 g, 10 mmol) and then returned to room temperature while stirring for 1 hour. The reaction solution was mixed with ethyl acetate, washed with water and dried with anhydrous sodium sulfate, and then the solvent was removed by evaporation under a reduced pressure, the thus obtained residue was mixed with diisopropyl ether (20 ml) and the thus precipitated crystals were collected by filtration to obtain 1.90 g of the title compound (5.3 mmol, 53% in yield).

EI-MS m/z 358 (M)$^+$; $^1$H-NMR (CDCl$_3$): δ 1.51 (9H, s), 2.01 (3H, s), 2.81 (2H, br s), 3.75 (2H, br s), 4.27 (2H, t), 4.33 (2H, t), 4.69 (2H, br s), 7.11 (1H, t), 7.19 (1H, t), 7.30 (1H, d), 7.49 (1H, d).

Synthesis Example 44a (The Inventive Compound) 2a-(4-(9-(2-hydroxy-ethyl)-2,3,4,9-tetrahydro-pyrido [3,4-b]indol-2-yl)-butyl)-2a,3,4,5-tetrahydro-1H-benz[cd]indol-2-one (1) Dichloromethane solution (20 ml) of 2-t-butoxycarbonyl-9-(2-acetoxy-ethyl)-1,3,4,9-tetrahydro-pyrido[3,4-b]indole (1.79 g, 5.0 mmol) was mixed with anisole (3 ml) and trifluoroacetic acid (5 ml) and stirred at room temperature for 18 hours. The solvent was removed by evaporation under a reduced pressure, and the resulting residue was precipitated by adding acetone (2 ml) and diisopropyl ether (20 ml), thereby obtaining 9-(2-acetoxy-ethyl)-2,3,4,9-tetrahydro-1H-pyrido[3,4-b]indole trifluoroacetate (426 mg, 1.0 mmol).

(2) The trifluoroacetate obtained in the above step (1) (420 mg, 1.0 mmol) and 2a-(4-bromobutyl)-2a,3,4,5-tetrahydro-1H-benz[cd]indol-2-one (308 mg, 1.0 mmol) were dissolved in methanol (20 ml), and the solution was mixed with potassium carbonate (560 mg, 4.0 mmol) and stirred under heating for 15 hours. The reaction solution was concentrated under a reduced pressure, and the thus obtained residue was dissolved in ethyl acetate and washed with water. After drying with anhydrous sodium sulfate, the solvent was removed by evaporation under a reduced pressure and the thus obtained oily material was purified by a silica gel column chromatography (elution by chloroform-methanol= 20:1) to obtain 108 mg of the title compound (23% in yield).

EI-MS m/z 443 (M)$^+$; $^1$H-NMR (CDCl$_3$): δ 1.10 (1H, m), 1.25 (2H, s), 1.34 (2H, m), 1.39 (2H, m), 1.51 (2H, m), 1.66 (1H, m), 1.85 (4H, m), 2.10 (2H, m), 2.51 (2H, m), 2.64 (1H, m), 2.83 (1H, m), 3.66 (2H, q), 3.86 (1H, t), 4.11 (2H, t), 6.64 (1H, d), 6.80 (1H, d), 7.10 (3H, m), 7.27 (1H, d), 7.45 (1H, d), 7.61 (1H, s).

Synthesis Example 45a (The Inventive Intermediate) 2-t-Butoxycarbonyl-9-allyl-2,3,4,9-tetrahydro-1H-pyrido[3,4-b]indole Anhydrous DMF solution (10 ml) of 2-t-butoxycarbonyl-2,3,4,9-tetrahydro-1H-pyrido[3,4-b]indole (4.40 g, 16.2 mmol) was mixed with 60% sodium hydride (700 mg, 10 mmol) and stirred at roam temperature for 1 hour. The reaction solution was cooled to −60° C., mixed with allyl bromide (2.18 g, 18 mmol) and then returned to room temperature by further stirring for 1 hour. The reaction solution was mixed with ethyl acetate (150 ml), washed with water and dried with anhydrous sodium sulfate, and then the solvent was removed by evaporation under a reduced pressure. The thus obtained residue was purified by a silica gel chromatography to obtain 4.32 g of the title compound as an oil (13.8 mmol, 87% in yield).

EI-MS m/z 312 (M)$^+$; $^1$H-NMR (CDCl$_3$): δ 1.50 (9H, s), 2.81 (2H, br s), 3.75 (2H, br s), 4.60 (2H, br s), 4.62 (2H, m), 4.94 (1H, d), 5.14 (1H, d), 5.92 (1H, m), 7.10 (1H, t), 7.17 (1H, t), 7.27 (1H, d), 7.49 (1H, d).

Synthesis Example 46a (The Inventive Compound) 2a-(4-(9-Allyl-2,3,4,9-tetrahydro-1H-pyrido[3,4-b] indol-2-yl)-butyl)-2a,3,4,5-tetrahydro-1H-benz[cd] indol-2-one (1) Dichloromethane solution (20 ml) of 2-t-butoxycarbonyl-9-allyl-2,3,4,9-tetrahydro-1H-pyrido[3,4-b] indole (624 mg, 2.0 mmol) was mixed with anisole (2 ml) and trifluoroacetic acid (3 ml) and stirred at room temperature for 6 hours. By removing the solvent by evaporation under a reduced pressure, 9-allyl-2,3,4,9-tetrahydro-pyrido [3,4-b]indole was obtained as trifluoroacetate.

(2) The trifluoroacetate obtained in the above step (1) and 2a-(4-bromobutyl)-2a,3,4,5-tetrahydro-1H-benz[cd]indol-2-one (616 mg, 2.0 mmol) were dissolved in DMF (20 ml), and the solution was mixed with anhydrous potassium carbonate (828 mg, 6.0 mmol) and stirred at room temperature for 2 days. The reaction solution was mixed with ethyl acetate, washed with water and dried with anhydrous sodium sulfate, and then the solvent was removed by evaporation under a reduced pressure and the thus obtained oily material was purified by a silica gel column chromatography (elution by chloroform-methanol=20:1) to obtain 404 mg of the title compound (46% in yield).

EI-MS m/z 439 (M)$^+$; $^1$H-NMR (CDCl$_3$): δ 1.12 (1H, m), 1.36 (2H, m), 1.53 (2H, m), 1.86 (3H, m), 2.11 (2H, m), 2.52 (2H, m), 2.64 (1H, m), 2.80 (5H, m), 3.58 (2H, s), 4.57 (2H, m), 4.88 (1H, dd), 5.09 (1H, dd), 5.89 (1H, m), 6.67 (1H, d), 6.80 (1H, d), 7.10 (3H, m), 7.22 (1H, d), 7.36 (1H, br s), 7.46 (1H, d).

Synthesis Example 47a (The Inventive Intermediate) 2-t-Butoxycarbonyl-9-(2-oxo-propyl)-2,3,4,9-tetrahydro-1H-pyrido[3,4-b]indole Palladium chloride (100 mg) and cupric chloride dihydrate (50 mg) were added to DMF solution (30 ml) of 2-t-butoxycarbonyl-9-allyl-2,3,4,9-tetrahydro-1H-pyrido[3, 4-b]indole (1.90 g, 6.1 mmol) and stirred at room temperature for 18 hours. The reaction solution was mixed with ethyl acetate, washed with water and dried with anhydrous sodium sulfate, and then the solvent was removed by evaporation under a reduced pressure, the thus obtained residue was mixed with diisopropyl ether (20 ml) and the thus precipitated crystals were collected by filtration to obtain 1.17 g of the title compound (59% in yield).

EI-MS m/z 328 (M)$^+$; $^1$H-NMR (CDCl$_3$): δ 1.50 (9H, s), 2.08 (3H, s), 2.83 (2H, br s), 3.77 (2H, br s), 4.52 (2H, br s), 4.71 (2H, br s), 7.13 (2H, t), 7.20 (1H, t), 7.51 (1H, d).

Synthesis Example 48a (The Inventive Compound) 2a-(4-(9-(2-oxo-Propyl)-2,3,4,9-tetrahydro-1H-pyrido[3,4-b]indol-2-yl)-butyl)-2a,3,4,5-tetrahydro-1H-benz[cd]indol-2-one (1) Dichloromethane solution (7 ml) of 2-t-butoxycarbonyl-9-(2-oxo-propyl)-2,3,4,9-tetrahydro-1H-pyrido[3,4-b]indole was mixed with anisole (0.5 ml) and trifluoroacetic acid (1.0 ml) and stirred at room temperature for 18 hours. The solvent was removed by evaporation under a reduced pressure, and the resulting residue was precipitated by adding acetone and diisopropyl ether, thereby obtaining 9-(2-oxo-propyl)-1,3,4,9-tetrahydro-pyrido[3,4-b] indole trifluoroacetate. Yield 217 mg (0.63 mmol), 93%.

(2) The 9-(2-oxo-propyl)-2,3,4,9-tetrahydro-1H-pyrido[3,4-b]indole trifluoroacetate obtained in the above step (1) (200 mg, 0.58 mmol) and 2a-(4-bromobutyl)-2a,3,4,5-tetrahydro-1H-benz[cd]indol-2-one were dissolved in DMF (20 ml), and the solution was mixed with anhydrous potassium carbonate (240 mg, 1.74 mmol) and stirred at room temperature for 2 days. The reaction solution was mixed with ethyl acetate, washed with water and dried with anhydrous sodium sulfate and then the solvent was removed by evaporation under a reduced pressure. The thus obtained residue was purified by a silica gel column chromatography (elution by chloroform-methanol=20:1) to obtain 174 mg of the title compound (0.38 mmol, 66% in yield).

EI-MS m/z 455 (M)$^+$; $^1$H-NMR (CDCl$_3$): δ 1.13 (1H, m), 1.36 (2H, m), 1.51 (2H, m), 1.85 (3H, m), 1.99 (3H, s), 2.10 (2H, m), 2.52 (2H, m), 2.66 (1H, m), 2.79 (5H, m), 3.51 (2H, s), 4.62 (2H, s), 6.66 (1H, d), 6.80 (1H, d), 7.12 (4H, m), 7.27 (1H, m), 7.49 (1H, d).

2. Synthesis examples of the compound (1) of the invention having group (b) and its production intermediate.

Synthesis Example 1b (The Inventive Compound) 2a-[4-(1,2,3,4,4a,5-Hexahydropyrazino[2,1-c]-1,4-benzoxazin-3-yl)-butyl]-2a,3,4,5-tetrahydro-1H-benz[cd]indol-2-one A 415 mg (3.00 mmol) portion of potassium carbonate was added to 6 ml of DMF solution containing 227 mg (1.00 mmol) of 1,2,3,4,4a,5-hexahydropyrazino[2,1-c]-1,4-benzoxazine hydrochloride and 308 mg (1.00 mmol) of 2a-(4-bromobutyl)-3,4,5-tetrahydro-1H-benz[cd]indol-2-one and stirred at room temperature for 2 days. The reaction solution was mixed with ethyl acetate and washed with water, and the water layer was extracted with ethyl acetate. The organic layers were combined and dried (Na$_2$SO$_4$), and then the solvent was removed by evaporation under a reduced pressure and the thus obtained oily material was purified by a silica gel column chromatography (100 cc; elution by chloroform-methanol=30:1). By further recrystallizing from ethyl acetate-diisopropyl ether, 302 mg of the title compound was obtained (72% in yield).

$^1$H-NMR (CDCl$_3$): δ 1.09 (1H, m), 1.37 (4H, m), 1.69–1.90 (4H, m), 2.11 (3H, m), 2.25 (2H, m), 2.63 (1H, ddd), 2.70–2.91 (4H, m), 3.12 (1H, m), 3.59 (1H, m), 3.94 (1H, t), 4.13 (1H, m), 6.67–7.08 (6H, m), 7.11 (1H, t), 8.85 (1H, s). Mass spectrum TSP m/z 418 (M+H)$^+$.

Synthesis Example 2b 3-(t-Butoxycarbonyl) aminomethyl-3,4-dihydro-2H-1,4-benzthiazine A 9 ml portion of 5 N hydrochloric acid was added to 1.14 g (4.28 mmol) of 3,4-dihydro-3-(4-hydroxybutanoyl) aminomethyl-2H-1,4-benzthiazine and stirred at room temperature for 1.5 hours and then at 50° C. for 1 hour. The reaction solution was returned to room temperature, alkalified by adding 50 ml of 1 N sodium hydroxide and extracted with ethyl acetate. After drying (Na$_2$SO$_4$), the solvent was removed by evaporation under a reduced pressure and the thus obtained oily material was dried under a reduced pressure and dissolved in 15 ml of THF. This was mixed with 5 ml of 1 N sodium hydroxide, cooled to 0° C., mixed with 1.13 ml (4.94 mmol) of d-t-butyl bicarbonate and stirred at room temperature for 2 hours. The reaction solution was extracted with ethyl acetate and dried (Na$_2$SO$_4$), and then the solvent was removed by evaporation under a reduced pressure and the resulting residue was purified by a silica gel column chromatography (140 cc; elution by ethyl acetate-hexane=1:2) to obtain 0.81 g of the title compound (68% in yield).

$^1$H-NMR (CDCl$_3$): δ 1.49 (9H, s), 2.77 (1H, dd), 2.85 (1H, dd), 3.08 (3H, m), 3.39 (1H, m), 3.70 (1H, br d), 4.04 (2H, br s), 6.76 (1H, dt), 6.84 (1H, d), 7.11 (1H, m), 7.18 (1H, dd). EI-MS m/z 306 (M)$^+$.

Synthesis Example 3b 3-(t-Butoxycarbonyl) aminomethyl-4-chloroacetyl-3,4-dihydro-2H-1,4-benzthiazine A 0.48 ml (3.47 mmol) portion of triethylamine was added to dichloromethane solution (10 ml) containing 0.81 g (2.89 mmol) of 3-(t-butoxycarbonyl)aminomethyl-3,4-dihydro-2H-1,4-benzthiazine and cooled to 0° C. This was mixed with 0.28 ml (3.47 mmol) of chloroacetyl chloride and stirred at room temperature for 3 hours. The reaction solution was poured into ice water and extracted with chloroform. The extract was washed with dilute hydrochloric acid and dried (Na$_2$SO$_4$), and then the solvent was removed by evaporation under a reduced pressure. The thus obtained residue was purified by a silica gel column chromatography (180 cc; elution by ethyl acetate-hexane=1:1) and further recrystallized from ethyl acetate-hexane to obtain 0.64 g of the title compound (62% in yield).

$^1$H-NMR (CDCl$_3$): δ 1.42 (9H, s), 2.84 (1H, m), 3.08 (1H, m), 3.28 (1H, m), 3.36 (1H, m), 3.96 (1H, br d), 4.18 (1H, br d), 4.94 (1H, br s), 5.26 (1H, br s), 7.28 (4H, m). EI-MS m/z 356 (M)$^+$.

Synthesis Example 4b 3-t-Butoxycarbonyl-1,2,3,4,4a,5-hexahydropyrazino[2,1-c]-1,4-benzthiazine A 13.47 g (97.43 mmol) portion of potassium carbonate was added to DMF solution (360 ml) containing 11.59 g (32.48 mmol) of 3-(t-butoxycarbonyl)aminomethyl-4-chloroacetyl-3,4-dihydro-2H-1,4-benzthiazine and stirred at room temperature overnight and then at 60° C. for 3 hours. This was returned to room temperature, mixed with cool water and extracted with ethyl acetate. The extract was dried (Na$_2$SO$_4$) and then concentrated under a reduced pressure. The thus dried residue under a reduced pressure was dissolved in 180 ml of tetrahydrofuran and cooled to 0° C. This was mixed with 4.48 ml (48.72 mmol) of borane-dimethyl sulfide complex and stirred at 0° C. for 2 hours and then at room temperature for 2 hours. Cool water was added dropwise to the reaction solution which was subsequently stirred for 30 minutes and then extracted with ethyl acetate. The extract was washed with dilute hydrochloric acid and dried (Na$_2$SO$_4$), and then the solvent was removed by evaporation under a reduced pressure. The thus obtained residue was purified by a silica gel column chromatography (650 cc; elution by ethyl acetate-hexane=1:4) and further recrystallized from ethyl acetate-hexane to obtain 5.04 g of the title compound (51% in yield).

$^1$H-NMR (CDCl$_3$): δ 1.49 (9H, s), 2.77 (1H, dd), 2.85 (1H, dd), 3.08 (3H, m), 3.39 (1H, m), 3.70 (1H, br d), 4.04 (2H, br s), 6.76 (1 H, dt), 6.84 (1H, d), 7.11 (1H, m), 7.18 (1H, dd). EI-MS m/z 306 (M)$^+$.

Synthesis Example 5b 1,2,3,4,4a,5-Hexahydropyrazino[2,1-c]-1,4-benzthiazine Hydrochloride A 1 ml portion of 5 N hydrochloric acid was added to acetic acid solution (10 ml) containing 0.52 g (1.70 mmol) of 3-t-butoxycarbonyl-1,2,3,4,4a,5-hexahydropyrazino[2,1-c]-1,4-benzthiazine, and the mixture was stirred overnight at room temperature and then at 60° C. for 2 hours. The solvent was removed by evaporation under a reduced pressure and the resulting residue was recrystallized from ethanol to obtain 0.36 g (88% in yield) of the title compound.

¹H-NMR (DMSO-d₆): δ 2.98 (4H, m), 3.30 (3H, m), 3.80 (1H, m), 4.01 (1H, br dd), 6.72 (1H, t), 6.99 (1H, d), 7.09 (2H, m), 7.28 (1H, dd). Mass spectrum TSP m/z 207 (M+H)⁺.

Synthesis Example 6b (The Inventive Compound) 2a-[4-(1,2,3,4,4a,5-Hexahydropyrazino[2,1-c]-1,4-benzthiazin-3-yl)-butyl]-2a,3,4,5-tetrahydro-1H-benz[cd]indol-2-one By the method described in Synthesis Example 1b, 256 mg (72% in yield) of the title compound was obtained from 200 mg (0.82 mmol) of 1,2,3,4,4a,5-hexahydropyrazino[2,1-c]-1,4-benzthiazine hydrochloride and 254 mg (0.82 mmol) of 2a-(4-bromobutyl)-2a,3,4,5-tetrahydro-1H-benz[cd]indol-2-one.

¹H-NMR (CDCl₃): δ 1.08 (1H, m), 1.37 (4H, m), 1.83 (3H, m), 2.12 (4H, m), 2.27 (2H, m), 2.71 –2.85 (6H, m), 3.05 (1H, m), 3.38 (1H, m), 3.63 (1H, m), 6.71 (2H, m), 6.80 (2H, m), 7.09 (3H, m), 8.77 (1H, m). Mass spectrum TSP m/z 434 (M+H)⁺.

Synthesis Example 7b (The Inventive Intermediate) 3-t-Butoxycarbonyl-1,2,3,4,4a,5-hexahydro-6,6-dioxo-6-λ⁶-pyrazino[2,1-c]-1,4-benzthiazine and 3-t-Butoxycarbonyl-1,2,3,4,4a,5-hexahydro-6-oxo-6-λ⁴-pyrazino[2,1-c]-1,4-benzthiazine Dichloromethane solution (70 ml) containing 3.06 g (10.00mmol) of 3-t-butoxycarbonyl-1,2,3,4,4a,5-hexahydropyrazino[2,1-c]-1,4-benzthiazine was stirred at room temperature for 2 hours by adding 1.81 g (10.50 mmol) of meta-chloroperbenzoic acid, for 3 hours by adding 0.64 g (3.72 ml) of the same and then for 1 hour by adding 0.33 g (1.91 mmol) of the same, to find that the material disappeared. The reaction solution was poured into ice water and extracted with chloroform. The extract was washed with sodium thiosulfate aqueous solution and sodium bicarbonate aqueous solution in that order and dried (Na₂SO₄) and then the solvent was removed by evaporation under a reduced pressure. The thus obtained residue was purified by a silica gel column chromatography (600 cc) to obtain 0.23 g (7% in yield) of 3-t-butoxycarbonyl-1,2,3,4,4a,5-hexahydro-6,6-dioxo-6-λ⁶-pyrazino[2,1-c]-1,4-benzthiazine (elution by ethyl acetate-hexane=2:1), and 0.72 g (Rf=0.39, ethyl acetate:hexane=2:1, yield 22%) and 1.92 g (Rf=0.32, ethyl acetate:hexane=2:1, yield 59%), respectively, of diastereomers of 3-t-butoxycarbonyl-1,2,3,4,4a,5-hexahydro-6-oxo-6-λ⁴-pyrazino[2,1-c]-1,4-benzthiazine (elution by ethyl acetate-hexane=3:1).

3-t-Butoxycarbonyl-1,2,3,4,4a,5-hexahydro-6,6-dioxo-6-λ⁶-pyrazino[2,1-c]-1,4-benzthiazine.

¹H-NMR (CDCl₃): δ 1.49 (9H, s), 2.96–3.29 (5H, m), 3.90 (2H, m), 3.08 (3H, m), 4.15 (2H, br s), 6.94 (1H, t), 6.98 (1H, d), 7.44 (1H, m), 7.81 (1H, dd). IR (cm⁻¹): 1130, 1300 (SO₂) Mass spectrum TSP m/z 339 (M+H)⁺.

3-t-Butoxycarbonyl-1,2,3,4,4a,5-hexahydro-6-oxo-6-λ⁴-pyrazino[2,1-c]-1,4-benzthiazine (Rf=0.39, ethyl acetate:hexane=2:1);

¹H-NMR (CDCl₃): δ 1.49 (9H, s), 3.04 (4H, m), 3.37 (1H, dd), 3.48 (1H, m), 3.89 (1H, br d), 4.10 (1H, br s), 6.90 (1H, d), 6.96 (1H, t), 7.36 (1H, m), 7.63 (1H, dd). IR (cm⁻¹): 1050 (S=O) Mass spectrum TSP m/z 323 (M+H)⁺.

3-t-Butoxycarbonyl-1,2,3,4,4a,5-hexahydro-6-oxo-6-λ⁴-pyrazino[2,1-c]-1,4-benzthiazine (Rf=0.32, ethyl acetate:hexane=2:1);

¹H-NMR (CDCl₃): δ 1.49 (9H, s), 2.64 (1H, t), 2.97 (1H, br s), 3.04 (2H, m), 3.12 (1H, br s), 3.82 (2H, m), 3.90 (1H, br s), 4.15 (2H, br s), 6.89 (1H, t), 7.04 (1H, br d), 7.43 (1H, br t), 7.56 (1H, dd). IR (cm⁻¹): 1050 (SO) Mass spectrum TSP m/z 323 (M+H)⁺.

Synthesis Example 8b (The Inventive Intermediate) 1,2,3,4,4a,5-Hexahydro-6-oxo-6-λ⁴-pyrazino[2,1-c]-1,4-benzthiazine Trifluoroacetate Dichloromethane solution (15 ml) containing 645 mg (2.00 mmol) of one of the diastereomers of 3-t-butoxycarbonyl-1,2,3,4,4a,5-hexahydro-6-oxo-6-λ⁴-pyrazino[2,1-c]-1,4-benzthiazine obtained in Synthesis Example 7b, having a value of Rf=0.39, was mixed with 1.5 ml of anisole and 1.5 ml of trifluoroacetic acid and allowed stand overnight at room temperature. By removing the solvent by evaporation under a reduced pressure and recrystallizing the resulting residue from ethyl acetate, 644 mg (96% in yield) of the title compound was obtained.

¹H-NMR (DMSO-d₆): δ 3.04 (1H, dt), 3.17 (1H, dd), 3.25 (1H, br t), 3.51 (1H, dd), 3.90 (1H, m), 4.25 (1H, d), 6.94 (1H, t), 7.16 (1H, d), 7.43 (1H, ddd), 7.51 (1H, dd). Mass spectrum TSP m/z 223 (M+H)⁺.

Synthesis Example 9b (The Inventive Compound) 2a-[4-(1,2,3,4,4a,5-Hexahydro-6-oxo-6-λ⁴-pyrazino[2,1-c]-1,4-benzthiazin-3-yl)-butyl]-2a,3,4,5-tetrahydro-1H-benz[cd]indol-2-one By the method described in Synthesis Example 1b, 381 mg (85% in yield) of the title compound was obtained from 336 mg (1.00 mmol) of 1,2,3,4,4a, 5-hexahydro-6-oxo-6-λ⁴-pyrazino[2,1-c]-1,4-benzthiazine trifluoroacetate obtained in Synthesis Example 8b and 339 mg (1.10 mmol) of 2a-(4-bromobutyl)-3,4,5-tetrahydro-1H-benz[cd]indol-2-one.

¹H-NMR (CDCl₃): δ 1.08 (1H, m), 1.37 (4H, m), 1.83 (3H, m), 2.12 (4H, m), 2.28 (2H, m), 2.64 (1H, ddd), 2.80 (3H, m), 2.98 (2H, m), 3.31 (1H, dd), 3.46 (1H, m), 3.80 (1H, m), 6.69 (1H, d), 6.80 (1H, d), 6.85 (1H, dd), 6.92 (1H, t), 7.11 (1H, t), 7.31 (1H, t), 7.61 (1H, dd), 8.32 (1H, d). Mass spectrum TSP m/z 450 (M+H)⁺.

Synthesis Example 10b (The Inventive Compound) 2a-[4-(1,2,3,4,4a,5-Hexahydro-6-oxo-6-λ⁴-pyrazino[2,1-c]-1,4-benzthiazin-3-yl)-butyl]-2a,3,4,5-tetrahydro-1H-benz[cd]indol-2-one By the methods described in Synthesis Examples 8b and 9b, the title compound was obtained from another one of the diastereomers of 3-t-butoxycarbonyl-1,2,3,4,4a,5-hexahydro-6-oxo-6-λ⁴-pyrazino[2,1-c]-1,4-benzthiazine obtained in Synthesis Example 7b, having a value of Rf=0.32.

¹H-NMR (CDCl₃): δ 1.10 (1H, m), 1.38 (4H, m), 1.84 (3H, m), 2.01–2.31 (6H, m), 2.61 (2H, m), 2.82–3.01 (5H, m), 3.80 (2H, m), 6.69 (1H, dd), 6.78 (1H, d), 6.84 (1H, t), 6.99 (1H, dd), 7.09 (1H, dt), 7.38 (1H, m), 7.55 (1H, dd), 8.75 (1H, d). Mass spectrum TSP m/z 450 (M+H)⁺.

Synthesis Example 11b (The Inventive Intermediate) 1,2,3,4,4a,5-Hexahydro-6,6-dioxo-6-λ⁶-pyrazino[2,1-c]-1,4-benzthiazine Trifluoroacetate By the method described in Synthesis Example 8b, 333 mg (99% in yield) of the title compound was obtained from 323 mg (0.95 mmol) of 3-t-butoxycarbonyl-1,2,3,4,4a,5-hexahydro-6,6-dioxo-6-λ⁶-pyrazino[2,1-c]-1,4-benzthiazine.

¹H-NMR (DMSO-d₆): δ 3.13 (3H, m), 3.47 (1H, s), 3.50 (1H, s), 3.56 (1H, dd), 3.81 (1H, dd), 4.01 (1H, m), 4.29 (1H, br d), 6.98 (1H, t), 7.26 (1H, d), 7.52 (1H, ddd), 7.67 (1H, dd). Mass spectrum TSP m/z 239 (M+H)$^+$.

Synthesis Example 12b (The Inventive Compound) 2a-[4-(1,2,3,4,4a,5-Hexahydro-6,6-dioxo-6-$\lambda^6$-pyrazino[2,1-c]-1,4-benzthiazin-3-yl)-butyl]-2a,3,4,5-tetrahydro-1H-benz[cd]indol-2-one By the method described in Synthesis Example 1b, 174 mg (68% in yield) of the title compound was obtained from 180 mg (0.51 mmol) of 1,2,3,4,4a,5-hexahydro-6,6-dioxo-6-$\lambda^6$-pyrazino[2,1-c]-1,4-benzthiazine trifluoroacetate and 173 mg (0.56 mmol) of 2a-(4-bromobutyl)-2a,3,4,5-tetrahydro-1H-benz[cd]indol-2-one.

$^1$H-NMR (CDCl$_3$): δ 1.10 (1H, m), 1.38 (4H, m), 1.84 (3H, m), 1.98–2.18 (4H, m), 2.28 (2H, m), 2.65 (1H, ddd), 2.89 (4H, m), 3.18 (2H, m), 3.78 (1H, m), 3.89 (1H, m), 6.71 (1H, dd), 6.80 (1H, d), 6.89 (1H, t), 6.93 (1H, dd), 7.11 (1H, dt), 7.38 (1H, m), 7.79 (1H, dd), 8.39 (1H, s). Mass spectrum TSP m/z 466 (M+H)$^+$.

Synthesis Example 13b (The Inventive Compound) 2a-[4-(2,3,4,4a-Tetrahydro-1H-pyrazino[1,2-a]quinoxalin-5(6H)-one-3-yl)-butyl]-2a,3,4,5-tetrahydro-1H-benz[cd]indol-2-one Hydrochloride By the method described in Synthesis Example 1b, 74 mg (27% in yield) of the title compound was obtained from 140 mg (0.58 mmol) of 2,3,4,4a-tetrahydro-1H-pyrazino[1,2-a]quinoxalin-5(6H)-one hydrochloride and 180 mg (0.58 mmol) of 2a-(4-bromobutyl)-2a,3,4,5-tetrahydro-1H-benz[cd]indol-2-one.

$^1$H-NMR (DMSO-d$_6$): δ 1.16 (1H, m), 1.71 (5H, m), 1.93 (1H, m), 2.08 (4H, m), 2.28 (1H, m), 2.59 (1H, m), 2.82 (1H, m), 3.07 (5H, m), 3.60 (2H, m), 3.79 (1H, br d), 3.89 (1H, br d), 3.95 (1H, br d), 6.63 (1H, d), 6.74 (1H, d), 6.89 (3H, m), 6.98 (1H, m), 7.07 (1H, t). Mass spectrum TSP m/z 431 (M+H)$^+$.

Synthesis Example 14b (The Inventive Compound) 2a-[4-(6-Methyl-2,3,4,4a-tetrahydro-1H-pyrazino[1,2-a]quinoxalin-5(6H)-one-3-yl)-butyl]-2a,3,4,5-tetrahydro-1H-benz[cd]indol-2-one By the method described in Synthesis Example 1b, 53 mg (58% in yield) of the title compound was obtained from 52 mg (0.20 mmol) of 6-methyl-2,3,4,4a-tetrahydro-1H-pyrazino[1,2-a]quinoxalin-5(6H)-one hydrochloride and 63 mg (0.20 mmol) of 2a-(4-bromobutyl)-2a,3,4,5-tetrahydro-1H-benz[cd]indol-2-one.

$^1$H-NMR (CDCl$_3$): δ 1.12 (1H, m), 1.34 (2H, m), 1.51 (2H, m), 1.83 (3H, m), 2.11 (4H, m), 2.35 (2H, m), 2.63 (1H, ddd), 2.82 (2H, m), 2.92 (1H, d), 3.35 (3H, s), 3.44 (3H, m), 6.70 (1H, d), 6.78 (2H, m), 6.94 (2H, m), 7.03 (1H, m), 7.10 (1H, dt), 8.47 (1H, s). Mass spectrum TSP m/z 445 (M+H)$^+$.

Synthesis Example 15b 3-Benzyloxycarbonyl-2,3,4,4a,5,6-hexahydro-6-trifluoroacetyl-1H-pyrazino[1,2-a]quinoxaline A 2 ml portion of THF solution containing 100 mg (0.30 mmol) of 3-benzyloxycarbonyl-2,3,4,4a-tetrahydro-1H-pyrazino[1,2-a]quinoxalin-5(6H)-one was cooled to 0° C., mixed with 59 μl (0.59 mmol) of borane-dimethyl sulfide complex and stirred overnight at room temperature. The reaction solution was mixed with ice water, stirred for 30 minutes and extracted with ethyl acetate. After drying (Na$_2$SO$_4$), the solvent was removed by evaporation under a reduced pressure, and the thus obtained residue was recrystallized from ethyl acetate-hexane to obtain crude crystals. A 97 mg portion of the crude crystals were dissolved in 2 ml of dichloromethane, and the solution was mixed with 125 μl (0.90 mmol) of triethylamine and 64 μl (0.45 mmol) of anhydrous trifluoroacetic acid and stirred overnight at room temperature. The reaction solution was poured into ice water, acidified by adding 1 N hydrochloric acid and then extracted with ethyl acetate. After drying (Na$_2$SO$_4$), the solvent was removed by evaporation under a reduced pressure, and the thus obtained residue was purified by a silica gel chromatography (30 cc; elution by ethyl acetate-hexane=1:5) to obtain 94 mg (74% in yield) of the title compound.

$^1$H-NMR (CDCl$_3$): δ 2.80 (1H, br s), 2.97 (1H, br d), 3.09 (1H, br s), 3.33 (1H, br s), 3.56 (1H, m), 3.81 (1H, br s), 4.08 (1H, m), 4.20 (2H, br s), 5.17 (2H, s), 6.80 (1H, t), 6.86 (1H, br m), 7.15 (1H, br s), 7.36 (5H, m), 7.65 (1H, br s). EI-MS m/z 419 (M)$^+$.

Synthesis Example 16b 2,3,4,4a,5,6-Hexahydro-6-trifluoroacetyl-1H-pyrazino[1,2-a]quinoxaline Hydrochloride A 80 μl portion of hydrochloric acid-methanol and 0.1 g of 10% Pd-C were added to 3 ml of ethanol solution containing 93 mg (0.22 mmol) of 3-benzyloxycarbonyl-2,3,4,4a,5,6-hexahydro-6-trifluoroacetyl-1H-pyrazino[1,2-a]quinoxaline, and 3 hours of catalytic hydrogenation was carried out at room temperature. The catalyst was filtered, the solvent was removed by evaporation under a reduced pressure and then the resulting residue was recrystallized from methanol-isopropyl ether to obtain 43 mg (61% in yield) of the title compound.

$^1$H-NMR (DMSO-d$_6$): δ 2.83 (1H, br t), 3.03 (1H, br t), 3.21 (1H, br t), 3.36 (1H, d), 3.45 (1H, d), 3.71 (2H, br d), 4.13 (2H, br d), 6.79 (1H, t), 7.08 (1H, d), 7.17 (1H, br s), 7.54 (1H, br s). EI-MS m/z 285 (M)$^+$.

Synthesis Example 17b (The Inventive Compounds) 2a-[4-(2,3,4,4a,5,6-Hexahydro-6-trifluoroacetyl-1H-pyrazino[1,2-a]quinoxalin-3-yl)-butyl]-2a,3,4,5-tetrahydro-1H-benz[cd]indol-2-one and 2a-[4-(2,3,4,4a,5,6-Hexahydro-1H-pyrazino[2-a]quinoxalin-3-yl)-butyl]2a,3,4,5-tetrahydro-1H-benz[cd]indol-2-one By the method described in Synthesis Example 1b, 24 mg (36% in yield) and 26 mg (47% in yield) of the respective title compounds were obtained from 42 mg (0.13 mmol) of 2,3,4,4a,5,6-hexahydro-6-trifluoroacetyl-1H-pyrazino[1,2-a]quinoxaline hydrochloride and 44 mg (0.14 mmol) of 2a-(4-bromobutyl)-2a,3,4,5-tetrahydro-1H-benz[cd]indol-2-one.

2a-[4-(2,3,4,4a,5,6-Hexahydro-6-trifluoroacetyl-1H-pyrazino[1,2-a]quinoxalin-3-yl)-butyl]-2a,3,4,5-tetrahydro-1H-benz[cd]indol-2-one $^1$H-NMR (CDCl$_3$): δ 1.09 (1H, m), 1.33 (4H, m), 1.83 (4H, m), 2.10 (4H, m), 2.28 (2H, m), 2.64 (1H, ddd), 2.82 (2H, m), 2.96 (1H, br m), 3.31 (1H, br m), 3.52 (1H, br m), 3.73 (1H, br m), 3.96 (1H, br m), 6.75 (5H, m), 7.11 (2H, t), 8.13 (1H, d). Mass spectrum TSP m/z 513 (M+H)$^+$.

2a-[4-(2,3,4,4a,5,6-Hexahydro-1H-pyrazino[1,2-a]quinoxalin-3-yl)-butyl]-2a,3,4,5-tetrahydro-1H-benz[cd]indol-2-one $^1$H-NMR (CDCl$_3$): δ 1.09 (1H, m), 1.38 (4H, m), 1.80 (4H, m), 2.13 (4H, m), 2.26 (2H, m), 2.65 (1H, m), 2.78 (2H, m), 2.92 (1H, d), 3.08 (1H, m), 3.24 (2H, m), 3.62 (1H, d), 6.47 (1H, m), 6.67 (4H, m), 6.79 (1H, d), 7.10 (1H, t), 8.15 (1H, s). Mass spectrum TSP m/z 417 (M+H)$^+$.

3. Synthesis examples of the compound (1) of the invention having group (c) and its production intermediate

Synthesis Example 1c N-t-Butoxycarbonyl-3-dimethylaminomethylene-4-piperidone N-t-Butoxycarbonyl-4-piperidone (3.0 g, 15 mmol) was dissolved in N,N-dimethylformamide dimethylacetal (15 ml) and heated under reflux for 1 hour. The solvent was removed by evaporation from the reaction solution under a reduced pressure, and the thus obtained material was separated and purified by a silica gel column chromatography to obtain 1.3 g (5.2 mmol, 34% in yield) of the title compound.

$^1$H-NMR (CDCl$_3$): δ 1.48 (9H, s), 2.43–2.50 (2H, m), 3.11 (6H, s), 3.59–3.62 (2H, m), 4.55 (2H, s), 7.49 (1H, s); MW 254.33 (C$_{13}$H$_{22}$N$_2$O$_3$); Mass spectrum TSP m/z 255 (M+H)$^+$.

Synthesis Example 2c N-t-Butoxycarbonyl-1,4,6,7-tetrahydro-pyrazolo[4,3-c]pyridine N-t-Butoxycarbonyl-3-dimethylaminomethylene-4-piperidone (690 mg, 2.7 mmol) was dissolved in methanol (12 ml), and the solution was mixed with hydrazine monohydrate (160 mg, 3.3 mmol) and heated under reflux for 1 hour. The solvent was removed by evaporation from the reaction solution under a reduced pressure, and the thus obtained material was separated and purified by a silica gel column chromatography to obtain 400 mg (1.8 mmol, 66% in yield) of the title compound.

$^1$H-NMR (CDCl$_3$): δ 1.48 (9H, s), 2.76–2.81 (2H, m), 3.68–3.76 (2H, m), 4.49 (2H, s), 7.36 (1H, s); MW 223.28 (C$_{11}$H$_{17}$N$_3$O$_2$); Mass spectrum TSP m/z 224 (M+H)$^+$.

Synthesis Example 3c N-Benzyl-3-furylmethylamine

Benzylamine (16 g, 150 mmol) was dissolved in dichloroethane (320 ml), and the solution was mixed with acetic acid (77 ml, 1.3 mol), sodium triacetoxyborohydride (57 g, 590 mmol) and 3-furaldehyde (13 g, 130 mmol) and stirred at room temperature for 16 hours. 5 N Sodium hydroxide aqueous solution was added to the reaction solution until it became basic, and the reaction product was extracted with ethyl acetate. The organic layer was washed with saturated brine and then dried with anhydrous magnesium sulfate. The solvent was removed by evaporation from the organic layer under a reduced pressure, and the thus obtained material was separated and purified by a silica gel column chromatography to obtain 19 g (100 mmol, 77% in yield) of the title compound.

$^1$H-NMR (CDCl$_3$): δ 1.61 (1H, br s), 3.66 (2H, s), 3.80 (2H, s), 6.40 (1H, s), 7.23–7.39 (7H, m); MW 187.24 (C$_{12}$H$_{13}$NO); Mass spectrum FAB m/z 188 (M+H)$^+$.

Synthesis Example 4c 2-(Benzyl-(3-furylmethyl)amino)ethanol

N-Benzyl-3-furylmethylamine (12 g, 64 mmol), triethylamine (18 ml, 130 mmol) and 2-bromoethanol (8.0 g, 64 mmol) were stirred at 60° C. to 70° C. for 16 hours in anhydrous N,N-dimethylformamide (120 ml). The reaction solution was mixed with ethyl acetate, washed with water and saturated brine and then dried with anhydrous magnesium sulfate. The solvent was removed by evaporation from the organic layer under a reduced pressure, and the thus obtained material was separated and purified by a silica gel column chromatography to obtain 7.1 g (31 mmol, 48% in yield) of the title compound.

$^1$H-NMR (CDCl$_3$): δ 1.64 (1H, br s), 2.67 (2H, t, J=5.4 Hz), 3.52 (2H, s), 3.58–3.62 (4H, m), 6.36 (1H, d, J=0.97 Hz), 7.24–7.41 (7H, m); MW 231.30 (C$_{14}$H$_{17}$NO$_2$); Mass spectrum ESI m/z 232 (M+H)$^+$.

Synthesis Example 5c 5-Benzyl-4,5,6,7-tetrahydro-furo[3,2-c]pyridine 2-(Benzyl-(3-furylmethyl)amino)ethanol (6.5 g, 28 mmol), triethylamine (5.9 ml, 42 mmol), 4-dimethylaminopyridine (250 mg, 2.1 mmol) and tosyl chloride (6.4 g, 34 mmol) were stirred at room temperature for 17 hours in dichloromethane (260 ml). The reaction solution was mixed with dichloromethane, washed with water and saturated brine and then dried with anhydrous magnesium sulfate. The solvent was removed by evaporation from the organic layer under a reduced pressure, and the thus obtained material was separated and purified by a silica gel column chromatography to obtain 5.4 g of crude 1-chloro-2-(benzyl-(3-furylmethyl)amino)ethane. The crude 1-chloro-2-(benzyl-(3-furylmethyl)amino)ethane (1.8 g) was dissolved in anhydrous tetrahydrofuran (35 ml) and cooled to 0° C. In an atmosphere of argon, n-butyl lithium hexane solution (14 mmol) was added thereto to carry out 2 hours of the reaction at room temperature. The reaction solution was mixed with 1 N sodium hydroxide aqueous solution, the reaction product was extracted with dichloromethane, and then the organic layer was washed with saturated brine and dried with anhydrous magnesium sulfate. The solvent was removed by evaporation from the organic layer under a reduced pressure, and the thus obtained material was separated and purified by a silica gel column chromatography to obtain 1.1 g (5.1 mmol, 73% in yield) of the title compound.

$^1$H-NMR (CDCl$_3$): δ 2.68–2.73 (2H, m), 2.79–2.84 (2H, m), 3.41 (2H, t, J=1.8 Hz), 3.71 (2H, s), 6.16 (1H, d, J=1.7 Hz), 7.25–7.39 (6H, m); MW 213.28 (C$_{14}$H$_{15}$NO); Mass spectrum EI-MS m/z 213 (M)$^+$.

Synthesis Example 6c 1-Methyl-1H-benz[cd]indol-2-one $^1$H-Benz[cd]indol-2-one (5.1 g, 30 mmol) was dissolved in anhydrous N,N-dimethylformamide (100 ml), and the solution was mixed with sodium hydride (60%, 1.2 g, 30 mmol) and stirred in an ice bath for 20 minutes. The reaction solution was mixed with methyl iodide (2.6 ml, 42 μmmol) and again stirred at room temperature for 1 hour. Ethyl acetate and water were added to the reaction solution. The reaction product was extracted with ethyl acetate, washed with saturated brine and dried with anhydrous sodium sulfate, the solvent was removed by evaporation under a reduced pressure, and then the thus obtained material was separated and purified by a silica gel column chromatography to obtain 4.7 g (26 mmol, 74% in yield) of the title compound.

MW 183.21 (C$_{12}$H$_9$NO); Mass spectrum EI-MS m/z 183 (M)$^+$.

Synthesis Example 7c 1-Methyl-2a,3,4,5-tetrahydro-1H-benz[cd]indol-2-one

Ethanol and Raney nickel slurry (Aldrich) were added to 1-methyl-1H-benz[cd]indol-2-one (4.5 g, 25 mmol), and catalytic reduction was carried out under ordinary pressure. The reaction was completed when 1.15 L of hydrogen absorption was observed, and then Raney nickel was removed by filtration, the filtrate was concentrated and the resulting material was separated and purified by a silica gel column chromatography to obtain 3.8 g (20 mmol, 80% in yield) of the title compound.

$^1$H-NMR (CDCl$_3$): δ 1.31 (1H, m), 1.91 (1H, m), 2.14 (1H, m), 2.42 (1H, m), 2.64 (1H, m), 2.92 (1H, dd), 3.17 (3H, s), 3.28 (1H, dd), 6.61 (1H, d), 6.82 (1H, d), 7.17 (1H, dd); MW 187.24 (C$_{12}$H$_{13}$NO); Mass spectrum EI-MS m/z 187 (M)$^+$.

Synthesis Example 8c 2a-(4-Bromobutyl)-1-methyl-2a,3,4,5-tetrahydro-1H-benz[cd]indol-2-one 1-Methyl-2a,3,4,5-tetrahydro-1H-benz[cd]indol-2-one (3.7 g, 20 mmol) was dissolved in anhydrous N,N-dimethylformamide (50 ml), and the solution was mixed with sodium hydride (60%, 800 mg, 20 mmol) and stirred at room temperature for 30 minutes. The reaction solution was cooled to −10° C. and mixed with 1,4-dibromobutane (7.0 ml) to carry out 1 hour of the reaction while increasing temperature of the reaction solution to room temperature. The reaction solution was mixed with diisopropyl ether and water to extract the reaction product, the resulting organic layer was washed three times with water and dried with anhydrous sodium sulfate, the solvent was removed by evaporation under a reduced pressure, and then the thus obtained material was separated and purified by a silica gel column chromatography to obtain 4.8 g (15 mmol, 75% in yield) of the title compound.

$^1$H-NMR (CDCl$_3$): δ 1.15 (1H, m), 1.30 (2H, m), 1.66–1.92 (5H, m), 2.00–2.20 (2H, m), 2.66 (1H, m), 2.86 (1H, m), 3.17 (3H, s), 3.29 (2H, t), 6.64 (1H, d), 6.83 (1H, d), 7.17 (1H, dd); 322.25 (C$_{16}$H$_{20}$BrNO); Mass spectrum EI-MS m/z 321:323 (intensity ratio=1:1) (M)$^+$.

Synthesis Example 9c 1-Ethyl-1H-benz[cd]indol-2-one

This was synthesized by the same method of Synthesis Example 6c, except that ethyl iodide was used instead of methyl iodide (yield, 83%).

MW 197.24 (C$_{13}$H$_{11}$NO); Mass spectrum EI-MS m/z 197 (M)$^+$.

Synthesis Example 10c 1-Ethyl-2a,3,4,5-tetrahydro-1H-benz[cd]indol-2-one

This was synthesized by the same method of Synthesis Example 7c, except that 1-ethyl-1H-benz[cd]indol-2-one was used instead of 1-methyl-1H-benz[cd]indol-2-one (yield, 81%).

$^1$H-NMR (CDCl$_3$): δ 1.28 (3H, t), 1.82–1.96 (1H, m), 2.09–2.17 (1H, m), 2.40–2.46 (1H, m), 2.58–2.69 (1H, m), 2.87–2.97 (1H, m), 3.25–3.30 (1H, m), 3.54–3.66 (1H, m), 3.77–3.89 (1H, m), 6.63 (1H, d, J=7.7 Hz), 6.80 (1H, d, J=7.8 Hz), 7.16 (1H, dd); MW 201.27 (C$_{13}$H$_{15}$NO); Mass spectrum EI-MS m/z 201 (M)$^+$.

Synthesis Example 11c 2a-(4-Bromobutyl)-1-ethyl-2a,3,4,5-tetrahydro-1H-benz[cd]indol-2-one This was synthesized by the same method of Synthesis Example 8c, except that 1-ethyl-2a,3,4,5-tetrahydro-1H-benz[cd]indol-2-one was used instead of 1-methyl-2a,3,4,5-tetrahydro-1H-benz[cd]indol-2-one (yield, 61%).

$^1$H-NMR (CDCl$_3$): δ 1.04–1.15 (1H, m), 1.26–1.45 (5H, m), 1.67–1.91 (5H, m), 2.06–2.19 (2H, m), 2.61–2.69 (1H, m), 2.82–2.90 (1H, m), 3.28 (2H, dt, J=0.97 Hz, 6.8 Hz), 3.50–3.58 (1H, m), 3.86–3.95 (1H, m), 6.64 (1H, d), 6.83 (1H, d), 7.17 (1H, dd); MW 336.27 (C$_{17}$H$_{22}$BrNO); Mass spectrum EI-MS m/z 335:337 (intensity ratio=1:1) (M)$^+$.

Synthesis Example 12c 2a-(4-Bromobutyl)-2a,3,4,5-tetrahydro-1H-benz[cd]indol-2-one 2a,3,4,5-Tetrahydro-1H-benz[cd]indol-2-one (3.0 g, 17 mmol) was dissolved in anhydrous N,N-dimethylformamide (120 ml), and the solution was mixed with sodium hydride (60%, 760 mg, 190 mmol) and stirred at room temperature for 1 hour. The reaction solution was mixed with 1,4-dibromobutane (6.3 ml, 52 mmol) and again stirred for 17 hours. The solvent was removed by evaporation under a reduced pressure, and ethyl acetate, water and hydrochloric acid (1 N) were added to the resulting residue. The reaction product was extracted with ethyl acetate, washed with saturated brine and dried with anhydrous sodium sulfate, the solvent was removed by evaporation under a reduced pressure, and then the thus obtained material was separated and purified by a silica gel column chromatography to obtain 1.8 g (5.8 mmol, 33% in yield) of the title compound.

$^1$H-NMR (CDCl$_3$): δ 1.17–1.28 (1H, m), 1.32–1.51 (2H, m), 1.72–1.90 (5H, m), 2.06–2.19 (2H, m), 2.60–2.70 (1H, m), 2.80–2.89 (1H, m), 3.30 (2H, t, J=7.0 Hz), 6.67 (1H, d, J=7.4 Hz), 6.81 (1H, d, J=7.8 Hz), 7.12 (1H, dd), 7.34 (1H, br s); MW 308.22 (C$_{15}$H$_{18}$BrNO); Mass spectrum EI-MS m/z 307:309 (intensity ratio=1:1) (M)$^+$.

Synthesis Example 13c (The Inventive Compound) 2a-(4-(1,3,4,5-Tetrahydro-1H-benzo[c]azepin-2-yl) butyl)-2a,3,4,5-tetrahydro-1H-benz[cd]indol-2-one 2,3,4,5-Tetrahydro-1H-benzo[c]azepin-1-one (160mg, 1.0 mmol) was dissolved in anhydrous tetrahydrofuran (5 ml), and the solution was mixed with lithium aluminum hydride (150 mg, 4.0 mmol) and stirred at 60° C. for 16 hours. The reaction solution was mixed with sodium sulfate decahydrate, stirred at room temperature for a while and then filtered through celite, and the insoluble matter was washed with methanol. The wash liquid and filtrate were combined, the solvent was removed by evaporation under a reduced pressure, the thus obtained residue was dissolved in anhydrous N,N-dimethylformamide (2 ml), and then the solution was mixed with 2a-(4-bromobutyl)-2a,3,4,5-tetrahydro-1H-benz[cd]indol-2-one (310 mg, 1.0 mmol) and potassium carbonate (210 mg, 1.5 mmol) and stirred at room temperature for 24 hours. The reaction solution was mixed with ethyl acetate, washed with water and saturated brine and dried with anhydrous sodium sulfate, the solvent was removed by evaporation under a reduced pressure, and then the thus obtained material was separated and purified by a silica gel column chromatography to obtain 220 mg (0.59 mmol, 59% in yield) of the title compound.

$^1$H-NMR (CDCl$_3$): δ 0.94–1.05 (1H, m), 1.18–1.48 (4H, m), 1.62–1.87 (5H, m), 2.02–2.17 (2H, m), 2.20–2.30 (2H, m), 2.58–2.67 (1H, m), 2.76–2.89 (3H, m), 3.02–3.09 (2H, m), 3.83 (2H, s), 6.64 (1H, d, J=7.6 Hz), 6.69 (1H, d, J=7.8 Hz), 7.04–7.15 (5H, m), 7.30 (1H, br s); MW 374.53 (C$_{25}$H$_{30}$N$_2$O); Mass spectrum EI-MS m/z 374 (M)$^+$.

By dissolving the thus obtained free compound in hydrochloric acid-saturated methanol, its hydrochloride was obtained. MW 410.99 (C$_{25}$H$_{31}$ClN$_2$O); Mass spectrum EI-MS m/z 374 (M–HCl)$^+$.

Synthesis Example 14c (The Inventive Compound) 2a-(4-(1,2,3,4-Tetrahydroisoquinolin-2-yl)butyl)-1-methyl-2a,3,4,5-tetrahydro-1H-benz[cd]indol-2-one 2a-(4-Bromobutyl)-1-methyl-2a,3,4,5-tetrahydro-1H-benz[cd]indol-2-one (120 mg, 0.37 mmol), 1,2,3,4- tetrahydroisoquinoline (55 mg, 0.41 mmol) and potassium carbonate (77 mg, 0.56 mmol) were stirred at room temperature for 18 hours in anhydrous N,N-dimethylformamide (1 ml). The reaction solution was mixed with ethyl acetate, washed with water and saturated brine and dried with anhydrous magnesium sulfate, the solvent was removed by evaporation under a reduced pressure, and then the thus obtained material was separated and purified by a silica gel column chromatography to obtain 130 mg (0.34 mmol, 90% in yield) of the title compound.

$^1$H-NMR (CDCl$_3$): δ 0.96–1.08 (1H, m), 1.15–1.33 (2H, m), 1.40–1.55 (2H, m), 1.74–1.94 (3H, m), 2.08–2.19 (2H, m), 2.32–2.44 (2H, m), 2.59–2.69 (3H, m), 2.81–2.91 (3H, m), 3.17 (3H, s), 3.54 (2H, s), 6.62 (1H, d, J=7.8 Hz), 6.82 (1H, d, J=7.8 Hz), 6.97–7.00 (1H, m), 7.05–7.11 (3H, m), 7.17 (1H, dd); MW 374.53 (C$_{22}$H$_{30}$N$_2$O); Mass spectrum TSP m/z 375 (M+H)$^+$.

By dissolving the thus obtained free compound in hydrochloric acid-saturated methanol, its hydrochloride was obtained.

MW 410.99 (C$_{25}$H$_{31}$ClN$_2$O); Mass spectrum TSP m/z 375 (M–Cl)$^+$.

Synthesis Example 15c (The Inventive Compound)
2a-(4-(1,2,3,4-Tetrahydroisoquinolin-2-yl)butyl)-1-ethyl-2a,3,4,5-tetrahydro-1H-benz[cd]indol-2-one This was synthesized by the same method of Synthesis Example 14c, except that 2a-(4-bromobutyl)-1-ethyl-2a,3,4,5-tetrahydro-1H-benz[cd]indol-2-one was used instead of 2a-(4-bromobutyl)-1-methyl-2a,3,4,5-tetrahydro-1H-benz[cd]indol-2-one (yield, 100%).

$^1$H-NMR (CDCl$_3$): δ 0.93–1.06 (1H, m), 1.17–1.34 (5H, m), 1.40–1.55 (2H, m), 1.75–1.95 (3H, m), 2.04–2.20 (2H, m), 2.31–2.43 (2H, m), 2.59–2.69 (3H, m), 2.80–2.91 (3H, m), 3.48–3.59 (3H, m), 3.83–3.93 (1H, m), 6.65 (1H, d, J=7.8 Hz), 6.81 (1H, d, J=7.8 Hz), 6.96–7.00 (1H, m), 7.05–7.12 (3H, m), 7.16 (1H, dd); MW 388.56 (C$_{26}$H$_{32}$N$_2$O); Mass spectrum EI-MS m/z 388 (M)$^+$.

By dissolving the thus obtained free compound in hydrochloric acid-saturated methanol, its hydrochloride was obtained.

MW 425.02 (C$_{26}$H$_{33}$ClN$_2$O); Mass spectrum TSP m/z 389 (M–Cl)$^+$.

Synthesis Example 16c 4,5,6,7-Tetrahydro-thieno[3,2-c]pyridine 4,5,6,7-Tetrahydro-thieno[3,2-c]pyridine-2-carboxylic acid hydrochloride (260 mg, 1.2 mmol) was mixed with 47% hydrogen bromide aqueous solution (3 ml) and heated under reflux for 4 hours. The reaction solution was returned to room temperature and alkalified by adding sodium hydroxide aqueous solution (5 N), and the reaction product was extracted with diethyl ether, washed with saturated brine and then dried with anhydrous magnesium sulfate. By evaporating the solvent from the organic layer under a reduced pressure, 160 mg (1.1 mmol, 95% in yield) of the title compound was obtained.

$^1$H-NMR (CDCl$_3$): δ 2.80 (2H, t, J=5.6 Hz), 3.15 (2H, t), 3.93 (2H, t, J=1.7 Hz), 6.74 (1H, d, J=5.1 Hz), 7.07 (1H, d); MW 139.22 (C$_7$H$_9$NS); Mass spectrum EI-MS m/z 139 (M)$^+$.

Synthesis Example 17c (The Inventive Compound)
2a-(4-(4,5,6,7-Tetrahydro-thieno[3,2-c]pyridin-5-yl)butyl)-2a,3,4,5-tetrahydro-1H-benz[cd]indol-2-one This was synthesized by the same method of Synthesis Example 14c, except that 4,5,6,7-tetrahydro-thieno[3,2-c] pyridine was used instead of 1,2,3,4-tetrahydroisoquinoline and 2a-(4-bromobutyl)-2a,3,4,5-tetrahydro-1H-benz[cd]indol-2-one was used instead of 2a-(4-bromobutyl)-1-methyl-2a,3,4,5-tetrahydro-1H-benz[cd]indol-2-one (yield, 84%).

$^1$H-NMR (CDCl$_3$): δ 1.03–1.16 (1H, m), 1.29–1.41 (2H, m), 1.41–1.56 (2H, m), 1.77–1.93 (3H, m), 2.06–2.20 (2H, m), 2.38–2.50 (2H, m), 2.59–2.73 (3H, m), 2.79–2.89 (3H, m), 3.48 (2H, s), 6.66–6.69 (2H, m), 6.79 (1H, d, J=7.8 Hz), 7.04 (1H, d, J=5.1 Hz), 7.11 (1H, dd, J=7.6 Hz), 8.00 (1H, br s); MW 366.52 (C$_{22}$H$_{26}$N$_2$OS); Mass spectrum EI-MS m/z 366 (M)$^+$.

By dissolving the thus obtained free compound in hydrochloric acid-saturated methanol, its hydrochloride was obtained.

MW 402.98 (C$_{22}$H$_{27}$ClN$_2$OS); Mass spectrum TSP m/z 367 (M–Cl)$^+$.

Synthesis Example 18c (The Inventive Compound)
2a-(4-(4,5,6,7-Tetrahydro-thieno[3,2-c]pyridin-5-yl)butyl)-1-methyl-2a,3,4,5-tetrahydro-1H-benz[cd]indol-2-one This was synthesized by the same method of Synthesis Example 14c, except that 4,5,6,7-tetrahydro-thieno[3,2-c] pyridine was used instead of 1,2,3,4-tetrahydroisoquinoline (yield, 34%).

$^1$H-NMR (CDCl$_3$): δ 0.95–1.07 (1H, m), 1.14–1.33 (2H, m), 1.39–1.53 (2H, m), 1.74–1.94 (3H, m), 2.07–2.19 (2H, m), 2.36–2.47 (2H, m), 2.59–2.72 (3H, m), 2.81–2.91 (3H, m), 3.17 (3H, s), 3.47 (2H, s), 6.63 (1H, d, J=7.6 Hz), 6.69 (1H, d, J=5.1 Hz), 6.82 (1H, d, J=7.8 Hz), 7.05 (1H, d), 7.17 (1H, dd); MW 380.55 (C$_{23}$H$_{28}$N$_2$OS); Mass spectrum TSP m/z 381 (M+H)$^+$.

By dissolving the thus obtained free compound in hydrochloric acid-saturated methanol, its hydrochloride was obtained.

MW 417.01 (C$_{23}$H$_{29}$ClN$_2$OS); Mass spectrum TSP m/z 381 (M–Cl)$^+$.

Synthesis Example 19c (The Inventive Compound)
2a-(4-(4,5,6,7-Tetrahydro-thieno[3,2-c]pyridin-5-yl)butyl)-1-ethyl-2a,3,4,5-tetrahydro-1H-benz[cd]indol-2-one This was synthesized by the same method of Synthesis Example 17c, except that 2a-(4-bromobutyl)-1-ethyl-2a,3,4,5-tetrahydro-1H-benz[cd]indol-2-one was used instead of 2a-(4-bromobutyl)-2a,3,4,5-tetrahydro-1H-benz[cd]indol-2-one (yield, 84%).

$^1$H-NMR (CDCl$_3$): δ 0.93–1.05 (1H, m), 1.16–1.34 (5H, m), 1.38–1.54 (2H, m), 1.74–1.93 (3H, m), 2.04–2.19 (2H, m), 2.34–2.46 (2H, m), 2.59–2.64 (3H, m), 2.70–2.80 (3H, m), 3.44–3.59 (3H, m), 3.82–3.93 (1H, m), 6.65 (1H, d, J=7.6 Hz), 6.69 (1H, d, J=5.1 Hz), 6.81 (1H, d, J=7.8 Hz), 7.05 (1H, d), 7.06 (1H, dd); MW 394.58 (C$_{24}$H$_{30}$N$_2$OS); Mass spectrum EI-MS m/z 394 (M)$^+$.

By dissolving the thus obtained free compound in hydrochloric acid-saturated methanol, its hydrochloride was obtained.

MW 431.04 (C$_{24}$H$_{31}$ClN$_2$OS); Mass spectrum TSP m/z 395 (M–Cl)$^+$.

Synthesis Example 20c 4,5,6,7-Tetrahydro-3H-imidazo[4,5-c]pyridine Dihydrochloride Monohydrate Histamine dichloride (5.0 g, 27 1 mol) was dissolved in concentrated hydrochloric acid (20 ml), dimethoxymethane (7.0 ml, 79 mmol) was added dropwise to the solution, and the mixture was stirred overnight at 100° C. By evaporating the solvent from the reaction solution and purifying the thus obtained crystals by their recrystallization from methanol, 4.6 g (22 mmol, 79% in yield) of the title compound was obtained.

MW 214.10 ($C_6H_{13}N_3OCl_2$); Mass spectrum EI-MS m/z 123 (M−(2HCl+$H_2O$))$^+$.

Synthesis Example 21c (The Inventive Compound)
2a-(4-(3,4,6,7-Tetrahydro-imidazo[4,5-c]pyridin-5-yl)butyl)-2a,3,4,5-tetrahydro-1H-benz[cd]indol-2-one This was synthesized by the same method of Synthesis Example 17c, except that 4,5,6,7-tetrahydro-3H-imidazo[4,5-c]pyridine dihydrochloride monohydrate was used instead of 4,5,6,7-tetrahydro-thieno-[3,2-c]pyridine (yield, 48%).

$^1$H-NMR (CDCl$_3$): δ 1.01–1.13 (1H, m), 1.28–1.40 (2H, m), 1.40–1.55 (2H, m), 1.76–1.91 (3H, m), 2.04–2.18 (2H, m), 2.42–2.51 (2H, m), 2.58–2.68 (3H, m), 2.68–2.76 (2H, m), 2.79–2.88 (1H, m), 3.45 (2H, s), 6.64 (1H, d, J=7.6 Hz), 6.79 (1H, d, J=7.6 Hz), 7.09 (1H, dd), 7.37 (1H, s), 8.15 (1H, br s); MW 350.47 ($C_{21}H_{26}N_4O$); Mass spectrum EI-MS m/z 350 (M)$^+$.

By dissolving the thus obtained free compound in hydrochloric acid-saturated methanol, its hydrochloride was obtained.

MW 386.93 ($C_{21}H_{27}ClN_4O$); Mass spectrum TSP m/z 351 (M−Cl)$^+$.

Synthesis Example 22c 4,5,6,7-Tetrahydro-1H-pyrazolo(4,3-pyridine Dihydrochloride 5-t-Butoxycarbonyl-1,4,6,7-tetrahydro-pyrazolo[4,3-c]pyridine (390 mg, 1.8 mmol) was dissolved in hydrochloric acid-saturated methanol (5 ml) and stirred at room temperature for 5.5 hours. The thus precipitated crystals were collected by filtration and washed with a small amount of cold methanol to obtain 220 mg (1.1 mmol, 65% in yield) of the title compound.

MW 196.08 ($C_6H_{11}Cl_2N_3$); Mass spectrum EI-MS m/z 123 (M−2HCl)$^+$.

Synthesis Example 23c (The Inventive Compound)
2a-(4-(1,4,6,7-Tetrahydro-pyrazolo[4,3-c]pyridin-5-yl)butyl)-2a,3,4,5-tetrahydro-1H-benz[cd]indol-2-one This was synthesized by the same method of Synthesis Example 17c, except that 4,5,6,7-tetrahydro-1H-pyrazolo[4,3-c]pyridine dihydrochloride was used instead of 4,5,6,7-tetrahydro-thieno-[3,2-c]pyridine (yield, 87%).

$^1$H-NMR (CDCl$_3$): δ 1.03–1.15 (1H, m), 1.30–1.50 (4H, m), 1.76–1.92 (3H, m), 2.06–2.17 (2H, m), 2.40–2.49 (2H, m), 2.60–2.89 (6H, m), 3.45 (2H, s), 6.66 (1H, d, J=7.8 Hz), 6.80 (1H, d, J=7.8 Hz), 7.11 (1H, dd), 7.26 (1H, s), 7.52 (1H, br s); MW 350.47 ($C_{21}H_{26}N_4O$); Mass spectrum TSP m/z 351 (M+H)$^+$.

By dissolving the thus obtained free compound in hydrochloric acid-saturated methanol, its hydrochloride was obtained.

MW 386.93 ($C_{21}H_{27}ClN_4O$); Mass spectrum TSP m/z 351 (M−Cl)$^+$.

Synthesis Example 24c (The Inventive Compound)
2a-(4-(4,5,6,7-Tetrahydro-furo[3,2-c]pyridin-5-yl)butyl)-2a,3,4,5-tetrahydro-1H-benz[cd]indol-2-one 5-Benzyl-4,5,6,7-tetrahydro-furo[3,2-c]pyridine (410 mg, 1.9 mmol) was dissolved in ethanol (4 ml), and the solution was mixed with 10% palladium on activated carbon (80 mg) and stirred at room temperature for 15 hours in an atmosphere of hydrogen. The reaction solution was filtered to remove 10% palladium on activated carbon, and the solvent was removed by evaporation under a reduced pressure to obtain crude 4,5,6,7-tetrahydro-furo[3,2-c]pyridine. This compound and 2a-(4-bromobutyl)-2a,3,4,5-tetrahydro-1H-benz[cd]indol-2-one (590 mg, 1.9 mmol) and potassium carbonate (400 mg, 2.9 mmol) were stirred at room temperature for 18 hours in anhydrous N,N-dimethylformamide (4 ml). The reaction solution was mixed with ethyl acetate, washed with water and saturated brine and then dried with anhydrous magnesium sulfate. The solvent was removed by evaporation from the organic layer under a reduced pressure, and the thus obtained material was separated and purified by a silica gel column chromatography to obtain 94 mg (0.27 mmol, 14% in yield) of the title compound.

$^1$H-NMR (CDCl$_3$): δ 1.03–1.15 (1H, m), 1.28–1.54 (4H, m), 1.76–1.92 (3H, m), 2.04–2.18 (2H, m), 2.38–2.50 (2H, m), 2.60–2.76 (5H, m), 2.79–2.89 (1H, m), 3.33 (2H, s), 6.15 (1H, d, J=1.9 Hz), 6.66 (1H, d, J=7.6 Hz), 6.80 (1H, d, J=7.8 Hz), 7.11 (1H, dd), 7.23 (1H, d), 7.28 (1H, br s); MW 350.46 ($C_{22}H_{26}N_2O_2$); Mass spectrum EI-MS m/z 350 (M)$^+$.

By dissolving the thus obtained free compound in hydrochloric acid-saturated methanol, its hydrochloride was obtained.

MW 386.91 ($C_{22}H_{27}ClN_2O_2$); Mass spectrum TSP m/z 351 (M−Cl)$^+$.

Synthesis Example 25c (The Inventive Compound)
5-(4-(2-oxo-2a,3,4,5-Tetrahydro-1H-benz[cd]indol-2a-yl)-butyl)-4,5,6,7-tetrahydro-thieno[3,2-c]pyridine-2-carboxylic Acid Methyl Ester 5-t-Butoxycarbonyl-4,5,6,7-tetrahydro-thieno[3,2-c]pyridine-2-carboxylic acid (300 mg, 1.1 mmol), potassium carbonate (150 mg, 1.1 mol) and methyl iodide (150 mg, 1.1 mmol) were stirred at room temperature for 4.5 hours in anhydrous N,N-dimethylformamide (3 ml). The reaction solution was mixed with ethyl acetate, washed with water and saturated brine and then dried with anhydrous sodium sulfate to obtain crude 5-t-butoxycarbonyl-4,5,6,7-tetrahydro-thieno[3,2-c]pyridine-2-carboxylic acid methyl ester. This was mixed with hydrochloric acid-saturated methanol (4 ml) and stirred at room temperature for 14 hours. By evaporating the solvent from the reaction solution under a reduced pressure, crude 4,5,6,7-tetrahydro-thieno[3,2-c]pyridine-2-carboxylic acid methyl ester hydrochloride was obtained. This compound and triethylamine (0.59 ml, 4.2 mmol) and 2a-(4-bromobutyl)-2a,3,4,5-tetrahydro-1H-benz[cd]indol-2-one (310 mg, 1.0 mmol) were stirred at room temperature for 24 hours in anhydrous N,N-dimethylformamide (10 ml). The reaction solution was mixed with ethyl acetate, washed with water and saturated brine and then dried with anhydrous sodium sulfate. The solvent was removed by evaporation under a reduced pressure, and the thus obtained material was separated and purified by a silica gel column chromatography to obtain 240 mg (0.56 mmol, 56% in yield) of the title compound.

$^1$H-NMR (CDCl$_3$): δ 1.04–1.16 (1H, m), 1.30–1.53 (4H, m), 1.76–1.92 (3H, m), 2.04–2.19 (2H, m), 2.38–2.49 (2H, m), 2.60–2.76 (3H, m), 2.79–2.92 (3H, m), 3.45 (2H, s), 3.85 (3H, s), 6.66 (1H, d, J=7.6 Hz), 6.80 (1H, d, J=7.8 Hz), 7.12 (1H, dd), 7.24 (1H, br s), 7.41 (1H, s); MW 424.56 ($C_{24}H_{28}N_2O_3S$); Mass spectrum EI-MS m/z 424 (M)$^+$.

By dissolving the thus obtained free compound in hydrochloric acid-saturated methanol, its hydrochloride was obtained.

MW 461.02 ($C_{24}H_{29}ClN_2O_3S$); Mass spectrum TSP m/z 425 (M−Cl)$^+$.

Synthesis Example 26c 5-t-Butoxycarbonyl-2-carbamoyl-4,5,6,7-tetrahydro-thieno[3,2-c]pyridine 5-t-Butoxycarbonyl-4,5,6,7-tetrahydro-thieno[3,2-c]pyridine-2-carboxylic acid (570 mg, 2.0 mmol) was dissolved in anhydrous tetrahydrofuran (10 ml), and the solution was mixed with 1,1-carbonyldiimidazole (320 mg, 2.0 mmol) and stirred at room temperature for 1 hour. The reaction solution was mixed with ammonia dioxane solution (0.5 M, 8.0 ml, 4.0 mmol) and the stirring was continued for 16 hours. The solvent was removed by evaporation from the reaction solution under a reduced pressure, and the residue was mixed with ethyl acetate and washed with water, hydrochloric acid (1 N), sodium hydroxide aqueous solution (1 N) and saturated brine. The organic layer was dried with anhydrous sodium sulfate, and the solvent was removed by evaporation under a reduced pressure to obtain 450 mg (1.6 mmol, 80% in yield) of the title compound.

$^1$H-NMR (CDCl$_3$): δ 1.49 (9H, s), 2.84–2.90 (2H, m), 3.70–3.76 (2H, m), 4.48 (2H, s), 5.76 (2H, br s), 7.25 (1H, s); MW 282.36 ($C_{13}H_{18}N_2O_3S$); Mass spectrum FAB m/z 283 (M+H)$^+$.

Synthesis Example 27c (The Inventive Compound) 5-(4-(2oxo-2a,3,4,5-Tetrahydro-1H-benz[cd]indol-2a-yl)-butyl)-4,5,6,7-tetrahydro-thieno[3,2-c]pyridine-2-carboxamide 5-t-Butoxycarbonyl-2-carbamoyl-4,5,6,7-tetrahydro-thieno[3,2-c]pyridine (280 mg, 1.0 mmol) was dissolved in hydrochloric acid methanol solution and stirred at room temperature for 18 hours. By evaporating the solvent from the reaction solution under a reduced pressure, crude 2-carbamoyl-4,5,6,7-tetrahydro-thieno[3,2-c]pyridine was obtained. This compound and triethylamine (0.56 ml, 4.0 mmol) and 2a-(4-bromobutyl)-2a,3,4,5-tetrahydro-1H-benz[cd]indol-2-one (290 mg, 0.95 mmol) were stirred at room temperature for 22 hours in anhydrous N,N-dimethylformamide (15 ml). The reaction solution was mixed with ethyl acetate, washed with water and saturated brine and then dried with anhydrous sodium sulfate. The solvent was removed by evaporation from the organic layer under a reduced pressure, and the thus obtained material was separated and purified by a silica gel column chromatography to obtain 170 mg (0.42 mmol, 44% in yield) of the title compound.

$^1$H-NMR (CDCl$_3$): δ 1.04–1.16 (1H, m), 1.30–1.55 (4H, m), 1.77–1.92 (3H, m), 2.06–2.18 (2H, m), 2.38–2.48 (2H, m), 2.60–2.73 (3H, m), 2.79–2.89 (3H, m), 3.45 (2H, s), 5.68 (2H, br s), 6.67 (1H, d, J=7.6 Hz), 6.80 (1H, d, J=7.6 Hz), 7.11 (1H, dd), 7.16 (1H, s), 7.54 (1H, br s); MW 409.55 ($C_{23}H_{27}N_3O_2S$); Mass spectrum EI-MS m/z 409 (M)$^+$.

By dissolving the thus obtained free compound in hydrochloric acid-saturated methanol, its hydrochloride was obtained.

MW 446.01 ($C_{23}H_{28}ClN_3O_2S$); Mass spectrum TSP m/z 410 (M−Cl)$^+$.

Synthesis Example 28c 5-t-Butoxycarbonyl-2-(morpholine-4-carbonyl)-4,5,6,7-tetrahydro-thieno[3,2-c]pyridine 5-t-Butoxycarbonyl-4,5,6,7-tetrahydro-thieno[3,2-c]pyridine-2-carboxylic acid (570 mg, 2.0 mmol) was dissolved in anhydrous tetrahydrofuran (10 ml), and the solution was mixed with 1,1-carbonyldiimidazole (320 mg, 2.0 mmol) and stirred at room temperature for 1 hour. The reaction solution was mixed with morpholine (170 mg, 2.0 mmol) and the stirring was continued for 14 hours. The solvent was removed by evaporation from the reaction solution under a reduced pressure, and the residue was mixed with ethyl acetate and washed with water, hydrochloric acid (1 N), sodium hydroxide aqueous solution (1 N) and saturated brine. The organic layer was dried with anhydrous sodium sulfate, and the solvent was removed by evaporation under a reduced pressure to obtain 610 mg (1.9 mmol, 94% in yield) of the title compound.

$^1$H-NMR (CDCl$_3$): δ 1.49 (9H, s), 2.82–2.87 (2H, m), 3.70–3.78 (10H, m), 4.47 (2H, s), 6.69 (1H, s); MW 352.45 ($C_{17}H_{24}N_2O_4S$); Mass spectrum TSP m/z 353 (M+H)$^+$.

Synthesis Example 29c 2-(Morpholine-4-carbonyl)-4,5,6,7-tetrahydro-thieno[3,2-c]pyridine 5-t-Butoxycarbonyl-2-(morpholine-4-carbonyl)-4,5,6,7-tetrahydro-thieno[3,2-c]pyridine (610 mg, 1.7 mmol) was mixed with hydrochloric acid-saturated methanol and stirred at room temperature for two nights. The solvent was removed by evaporation from the reaction solution under a reduced pressure, and the residue was mixed with sodium hydroxide aqueous solution (1 N). The reaction product was extracted with ethyl acetate, and the organic layer was washed with saturated brine and dried with anhydrous magnesium sulfate. By evaporating the solvent from the organic layer under a reduced pressure, 270 mg (1.1 mmol, 63% in yield) of the title compound was obtained.

$^1$H-NMR (CDCl$_3$): δ 2.79–2.84 (2H, m), 3.14–3.18 (2H, m), 3.70–3.78 (8H, m), 3.88–3.92 (2H, m), 6.96 (1H, s); MW 252.33 ($C_{12}H_{16}N_2O_2S$); Mass spectrum EI-MS m/z 252 (M)$^+$.

Synthesis Example 30c (The Inventive Compound) 2a-(4-(2-Morpholine-4-carbonyl)-4,5,6,7-tetrahydro-thieno[3,2-c]pyridin-5-yl)butyl)-2a,3,4,5-tetrahydro-1H-benz[cd]indol-2-one This was synthesized by the same method of Synthesis Example 17c, except that 2-(morpholine-4-carbonyl)-4,5,6,7-tetrahydro-thieno[3,2-c]pyridine was used instead of 4,5,6,7-tetrahydro-thieno[3,2-c]pyridine (yield, 59%).

$^1$H-NMR (CDCl$_3$): δ 1.04–1.16 (1H, m), 1.28–1.53 (4H, m), 1.76–1.92 (3H, m), 2.06–2.18 (2H, m), 2.39–2.49 (2H, m), 2.60–2.75 (3H, m), 2.79–2.89 (3H, m), 3.44 (2H, s), 3.68–3.78 (8H, m), 6.66 (1H, d, J=7.6 Hz), 6.80 (1H, d, J=7.8 Hz), 6.91 (1H, s), 7.11 (1H, dd), 7.23 (1H, br s); MW 479.64 ($C_{27}H_{33}N_3O_3S$); Mass spectrum EI-MS m/z 479 (M)$^+$.

By dissolving the thus obtained free compound in hydrochloric acid-saturated methanol, its hydrochloride was obtained.

MW 516.10 ($C_{27}H_{34}ClN_3O_3S$); Mass spectrum TSP m/z 480 (M−Cl)$^+$.

Synthesis Example 31c (The Inventive Compound) 5-(4-(2-oxo-2a,3,4,5-Tetrahydro-1H-benz[cd]indol-2a-yl)-butyl)-4,5,6,7-tetrahydro-thieno[3,2-c]pyridine-2-carboxylic Acid Benzyl Ester This was synthesized by the same method of Synthesis Example 25c, except that benzyl bromide was used instead of methyl iodide (yield, 71%).

$^1$H-NMR (CDCl$_3$): δ 1.04–1.16 (1H, m), 1.24–1.55 (4H, m), 1.75–1.93 (3H, m), 2.04–2.18 (2H, m), 2.36–2.49 (2H, m), 2.59–2.74 (3H, m), 2.78–2.89 (3H, m), 3.44 (2H, s), 5.30 (2H, s), 6.66 (1H, d, J=7.6 Hz), 6.80 (1H, d, J=7.8 Hz), 7.11 (1H, dd), 7.30–7.45 (7H, m); MW 500.66 ($C_{30}H_{32}N_2O_3S$); Mass spectrum EI-MS m/z 500 (M)$^+$.

By dissolving the thus obtained free compound in hydrochloric acid-saturated methanol, its hydrochloride was obtained.

MW 537.12 ($C_{30}H_{33}ClN_2O_3S$); Mass spectrum TSP m/z 501 (M–Cl)$^+$.

Synthesis Example 32c 5-t-Butoxycarbonyl-2-dimethylcarbamoyl-4,5,6,7-tetrahydro-thieno[3,2-c]pyridine 5-t-Butoxycarbonyl-4,5,6,7-tetrahydro-thieno[3,2-c]pyridine-2-carboxylic acid (570 mg, 2.0 mmol) was dissolved in anhydrous tetrahydrofuran (10 ml), and the solution was mixed with 1,1-carbonyldiimidazole (320 mg, 2.0 mmol) and stirred at room temperature for 1 hour. The reaction solution was mixed with dimethylamine tetrahydrofuran solution (2.0 M, 4.0 ml, 2.0 mmol) and the stirring was continued for 15 hours. The solvent was removed by evaporation from the reaction solution under a reduced pressure, and the residue was mixed with ethyl acetate and washed with water, hydrochloric acid (1 N), sodium hydroxide aqueous solution (1 N) and saturated brine. The organic layer was dried with anhydrous sodium sulfate, and the solvent was removed by evaporation under a reduced pressure to obtain 470 mg (1.5 mmol, 77% in yield) of the title compound.

$^1$H-NMR (CDCl$_3$): δ 1.49 (9H, s), 2.84 (2H, br s), 3.18 (6H, br s), 3.72 (2H, br s), 4.47 (2H, s), 7.05 (1H, s); MW 310.41 ($C_{15}H_{22}N_2O_3S$); Mass spectrum FAB m/z 311 (M+H)$^+$.

Synthesis Example 33c (The Inventive Compound) 2a-(4-(2-Dimethylcarbamoyl-4,5,6,7-tetrahydro-thieno[3,2-c]pyridin-5-yl)butyl)-2a,3,4,5-tetrahydro-1H-benz[cd]indol-2-one This was obtained by the same method of Synthesis Example 27c, except that 5-t-butoxycarbonyl-2-dimethylcarbamoyl-4,5,6,7-tetrahydro-thieno[3,2-c]pyridine was used instead of 5-t-butoxycarbonyl-2-carbamoyl-4,5,6,7-tetrahydro-thieno[3,2-c]pyridine (yield, 34%).

$^1$H-NMR (CDCl$_3$): δ 1.04–1.16 (1H, m), 1.30–1.55 (4H, m), 1.76–1.92 (3H, m), 2.06–2.18 (2H, m), 2.38–2.48 (2H, m), 2.60–2.75 (3H, m), 2.80–2.89 (3H, m), 3.15 (6H, br s), 3.45 (2H, s), 6.66 (1H, d, J=7.8 Hz), 6.80 (1H, d, J=7.8 Hz), 6.98 (1H, s), 7.11 (1H, dd), 7.31 (1H, br s); MW 437.60 ($C_{25}H_{31}N_3O_2S$); Mass spectrum EISM m/z 437 (M)$^+$.

By dissolving the thus obtained free compound in hydrochloric acid-saturated methanol, its hydrochloride was obtained.

MW 474.66 ($C_{25}H_{32}ClN_3O_2S$); Mass spectrum TSP m/z 438 (M–Cl)$^+$.

Synthesis Example 34c 5-t-Butoxycarbonyl-4,5,6,7-tetrahydro-thieno[3,2-c]pyridine 4,5,6,7-Tetrahydro-thieno[3,2-c]pyridine (1.3 g, 9.0 mmol) was dissolved in dichloromethane (25 ml), and the solution was mixed with t-butyl bicarbonate (3.1 ml, 13 mmol) and triethylamine (1.3 ml, 9. 0 mmol) and stirred at room temperature for 13 hours. The reaction solution was mixed with dichloromethane, washed with water and saturated brined and dried with anhydrous sodium sulfate. When the solvent was removed by evaporation from the organic layer under a reduced pressure and the thus obtained material was separated and purified by a silica gel column chromatography, it was able to isolate a part of the title compound, but the most part was obtained as its mixture with t-butyl bicarbonate (total yield, 2.3 g).

$^1$H-NMR (CDCl$_3$): δ 1.49 (9H, s), 2.84 (2H, br s), 3.73 (2H, br s), 4.50 (2H, br s), 6.78 (1H, d, J=4.8 Hz), 7.12 (1H, d); MW 239.33 ($C_{12}H_{17}NO_2S$); Mass spectrum EISM m/z 239 (M)$^+$.

Synthesis Example 35c 5-t-Butoxycarbonyl-2-methyl-4,5,6,7-tetrahydro-thieno[3,2-c]pyridine 5-t-Butoxycarbonyl-4,5,6,7-tetrahydro-thieno[3,2-c]pyridine (330 mg, 1.4 mmol) was dissolved in anhydrous tetrahydrofuran (18 ml), n-butyl lithium hexane solution (3.0 mmol) was added dropwise to the solution which was cooled in an ice bath, and then the mixture was stirred for 1 hour. This was further mixed with methyl iodide (430 mg, 3.0 mmol), and the stirring was continued while increasing the reaction temperature to room temperature spending 2 hours. The reaction solution was mixed with water and the reaction product was extracted therefrom with ethyl acetate. The organic layer was washed with saturated brine and dried with anhydrous magnesium sulfate, and then the solvent was removed by evaporation under a reduced pressure and the thus obtained material was separated and purified by a silica gel column chromatography to obtain 110 mg (0.42 mmol, 31% in yield) of the title compound.

$^1$H-NMR (CDCl$_3$): δ 1.49 (9H, s), 2.42 (3H, s), 2.75 (2H, br s), 3.69 (2H, br s), 4.40 (2H, s), 6.43 (1H, s); MW 253.36 ($C_{13}H_{19}NO_2S$); Mass spectrum TSP m/z 254 (M+H)$^+$.

Synthesis Example 36c 2-Methyl-4,5,6,7-tetrahydro-thieno[3,2-c]pyridine 5-t-Butoxycarbonyl-2-methyl-4,5,6,7-tetrahydro-thieno[3,2-c]pyridine (100 mg, 0.40 mmol) was dissolved in hydrochloric acid methanol solution and stirred at room temperature for 14 hours. By evaporating the solvent from the reaction solution under a reduced pressure, 60 mg (0.39 mmol, 99% in yield) of the title compound was obtained.

$^1$H-NMR (CDCl$_3$): δ 2.42 (3H, s), 2.69–2.74 (2H, m), 3.10–3.15 (2H, m), 3.83 (2H, s), 6.39 (1H, s); MW 153.24 ($C_8H_{11}NS$); Mass spectrum TSP m/z 154 (M+H)$^+$.

Synthesis Example 37c (The Inventive Compound) 2a-(4-(2-Methyl-4,5,6,7-tetrahydro-thieno[3,2-c]pyridin-5-yl)butyl)-2a,3,4,5-tetrahydro-1H-benz[cd]indol-2-one This was synthesized by the same method of Synthesis Example 17c, except that 2-methyl-4,5,6,7-tetrahydro-thieno[3,2-c]pyridine was used instead of 4,5,6,7-tetrahydro-thieno[3,2-c]pyridine (yield, 78%).

$^1$H-NMR (CDCl$_3$): δ 1.02–1.15 (1H, m), 1.30–1.53 (4H, m), 1.76–1.92 (3H, m), 2.06–2.18 (2H, m), 2.35–2.48 (5H, m), 2.59–2.89 (6H, m), 3.38 (2H, s), 6.34 (1H, s), 6.66 (1H, d, J=7.8 Hz), 6.80 (1H, d, J=7.8 Hz), 7.11 (1H, dd), 7.19 (1H, br s); MW 380.55 ($C_{23}H_{28}N_2OS$); Mass spectrum EI-MS m/z 380 (M)$^+$.

By dissolving the thus obtained free compound in hydrochloric acid-saturated methanol, its hydrochloride was obtained.

MW 417.01 ($C_{23}H_{29}ClN_2OS$); Mass spectrum TSP m/z 381 (M–Cl)$^+$.

Synthesis Example 38c 5-t-Butoxycarbonyl-3-methyl-4,5,6,7-tetrahydro-thieno[3,2-c]pyridine-2-carboxylic Acid 5-t-Butoxycarbonyl-4,5,6,7-tetrahydro-thieno[3,2-c]pyridine-2-carboxylic acid (300 mg, 1.1 mmol) was dissolved in anhydrous tetrahydrofuran (5 ml), n-butyl lithium hexane solution (15%, 1.5 ml, 2.3 mmol) was added dropwise thereto at −78° C. in an atmosphere of argon, and then the mixture was stirred for 1 hour. The reaction solution was mixed with methyl iodide (1.6 ml, 2.7 mmol) and stirred for 1 hour and then at room temperature for 1 hour. The reaction solution was mixed with ethyl acetate and hydrochloric acid (1 N) to acidify the water layer, and then the reaction product was extracted with ethyl acetate. The organic layer was washed with saturated brine and dried with anhydrous magnesium sulfate, and then the solvent was removed by evaporation under a reduced pressure and the thus obtained material was separated and purified by a silica gel column chromatography to obtain 180 mg (0.61 mmol, 57% in yield) of the title compound.

$^1$H-NMR (CDCl$_3$): δ 1.50 (9H, s), 2.43 (3H, m), 3.72 (2H, s), 4.39 (2H, br s), 7.49 (1H, s); MW 297.37 (C$_{14}$H$_{19}$NO$_4$S); Mass spectrum TSP m/z 298 (M+H)$^+$.

Synthesis Example 39c 6,7-Dimethoxy-1-methyl-1, 2,3,4-tetrahydro-isoquinoline-2-carboxylic Acid t-Butyl Ester 6,7-Dihydroxy-1-methyl-1,2,3,4-tetrahydro-isoquinoline monohydrobromide (510 mg, 2.9 mol) was dissolved in water (5 ml) and dioxane (5 ml), and the solution was mixed with sodium bicarbonate (410 mg, 4.9 mmol) and t-butyl bicarbonate (470 mg, 2.2 mmol) and stirred at room temperature for 2.5 hours. Ethyl acetate was added to the reaction solution, and the organic layer was washed with dilute hydrochloric acid and saturated brine and then dried with anhydrous magnesium sulfate. The solvent was removed by evaporation from the organic layer under a reduced pressure and the thus obtained material was dried under a reduced pressure to obtain crude 2-t-butoxycarbonyl-6,7-dihydroxy-1-methyl-1,2,3,4-tetrahydro-isoquinoline (610 mg). Crude 2-t-butoxycarbonyl-6,7-dihydroxy-1-methyl-1,2,3,4-tetrahydro-isoquinoline (610 mg) was dissolved in anhydrous N,N-dimethylformamide (6 ml), and the solution was mixed with sodium hydride (60%, 170 mg, 4.1 mmol) and stirred at room temperature for 45 minutes. The reaction solution was mixed with methyl iodide (580 mg, 4.1 mmol) and again stirred for 1 hour. The reaction solution was mixed with ethyl acetate, washed with water and saturated brined and dried with anhydrous magnesium sulfate. The solvent was removed by evaporation from the organic layer under a reduced pressure, and the thus obtained material was separated and purified by a silica gel column chromatography to obtain 190 mg (0. 62 mmol, 32% in yield) of the title compound.

$^1$H-NMR (CDCl$_3$): δ 1.42 (3H, d, J=6.8 Hz), 1.49 (9H, s), 2.50–3.30 (5H, br s), 3.85 (3H, s), 3.86 (3H, s), 6.59 (2H, s); MW 307.39 (C$_{17}$H$_{25}$NO$_4$); as; spectrum TSP m/z 308 (M+H)$^+$.

Synthesis Example 40c (The Inventive Compound) 2a-(4-(6,7-Dimethoxy-1-methyl-1,2,3,4-tetrahydro-isoquinolin-2-yl)-butyl)-2a,3,4,5-tetrahydro-1H-benz[cd]indol-2-one 2-t-Butoxycarbonyl-6,7-dimethoxy-1-methyl-1,2,3,4-tetrahydro-isoquinoline (190 mg, 0.61 mmol) was dissolved in hydrochloric acid methanol solution (4 ml) and stirred at room temperature for 2.5 hours. The residue obtained by evaporating the solvent from the reaction solution under a reduced pressure was dissolved in anhydrous N,N-dimethylformamide (2 ml), and the solution was mixed with 2a-(4-bromobutyl)-2a,3,4,5-tetrahydro-1H-benz[cd]indole-2-one (190 mg, 0.61 mmol) and potassium carbonate (250 mg, 1.8 mmol) and stirred at room temperature for 14 hours. The reaction solution was mixed with ethyl acetate, washed with water and saturated brine and dried with anhydrous magnesium sulfate. The solvent was removed by evaporation under a reduced pressure, and the thus obtained material was separated and purified by a silica gel column chromatography to obtain 200 mg (0.46 mmol, 76% in yield) of the title compound.

$^1$H-NMR (CDCl$_3$): δ 1.01–1.15 (1H, m), 1.22–1.53 (7H, m), 1.76–1.89 (3H, m), 2.06–2.19 (2H, m), 2.42–2.90 (7H, m), 2.94–3.04 (1H, m), 3.70–3.77 (1H, m), 3.83 (3H, s), 3.83 (3H, s), 6.51 (1H, s), 6.53 (1H, s), 6.65 (1H, d, J=7.6 Hz), 6.80 (1H, d, J=7.4 Hz), 7.11 (1H, dd), 7.16 (1H, br s); MW 434.58 (C$_{27}$H$_{34}$N$_2$O$_3$); Mass spectrum EI-MS m/z 434 (M)$^+$.

By dissolving the thus obtained free compound in hydrochloric acid-saturated methanol, its hydrochloride was obtained.

MW 471.04 (C$_{27}$H$_{35}$ClN$_2$O$_3$); Mass spectrum TSP m/z 435 (M−Cl)$^+$.

Synthesis Example 41c 3-Fluoro-2-methyl-benzoic Acid Methyl Ester

3-Fluoro-2-methyl-benzoic acid (4.8 g, 31 mmol), potassium carbonate (4.3 g, 31 mmol) and methyl iodide (4.5 g, 31 mmol) were stirred at room temperature for 17.5 hours in anhydrous N,N-dimethylformamide (50 ml). The reaction solution was mixed with ethyl acetate, washed with water and saturated brine and then dried with anhydrous magnesium sulfate. The solvent was removed by evaporation from the organic, layer under a reduced pressure, and the thus obtained material was separated and purified by a silica gel column chromatography to obtain 4.8 g (27 mmol, 87% in yield) of the title compound.

$^1$H-NMR (CDCl$_3$): δ 2.49 (3H, d, J=2.4 Hz), 3.90 (3H, s), 7.15–7.23 (2H, m), 7.67 (1H, dd, J=2.2 Hz, 6.8 Hz); MW 168.17 (C$_9$H$_9$O$_2$F); Mass spectrum EI-MS m/z 168 (M)$^+$.

Synthesis Example 42c 2-Bromomethyl-3-fluoro-benzoic Acid Methyl Ester

3-Fluoro-2-methyl-benzoic acid methyl ester (4.3 g, 26 mmol), N-bromosuccinimide (5.0 g, 28 mmol) and AIBN (2,2'-azobisisobutyronitril) (420 mg, 2.6 mmol) were stirred at 80° C. for 10 hours in carbon tetrachloride (45 ml). The reaction solution was mixed with water and chloroform, washed with saturated sodium bicarbonate aqueous solution and saturated brine and then dried with anhydrous magnesium sulfate. The solvent was removed by evaporation from the extract under a reduced pressure, and the thus obtained material was separated and purified by a silica gel column chromatography to obtain 5.1 g (21 mmol, 81% in yield) of the title compound.

$^1$H-NMR (CDCl$_3$): δ 3.96 (3H, s), 5.00 (2H, d, J=1.7 Hz), 7.26 (1H, ddd, J=1.2 Hz, 8.2 Hz, 9.0 Hz), 7.37 (1H, ddd, J=5.4 Hz, 8.2 Hz), 7.78 (1H, dd); MW 247.06 (C$_9$H$_8$O$_2$BrF); Mass spectrum EI-MS m/z 245:247 (intensity ratio 1:1) (M)$^+$.

Synthesis Example 43c 2-Cyanomethyl-3-fluoro-benzoic Acid Methyl Ester

2-Bromomethyl-3-fluoro-benzoic acid methyl ester (5.1 g, 21 mmol) was dissolved in methanol (50 ml), and sodium cyanide aqueous solution (4.2 ml, 5 ml, 21 mmol) was added dropwise thereto. After completion of the dropwise addition, the mixture was stirred at 50° C. for 2 hours. The residue obtained by evaporating the solvent from the reaction solution under a reduced pressure was mixed with ethyl acetate, washed with water and saturated brine and then dried with anhydrous it magnesium sulfate. The solvent was removed by evaporation from the organic layer under a reduced pressure, and the thus obtained material was separated and purified by a silica gel column chromatography to obtain 3.3 g (17 mmol, 82% in yield) of the title compound.

$^1$H-NMR (CDCl$_3$): δ 3.97 (3H, s), 4.19 (2H, d, J=1.5 Hz), 7.34 (1H, ddd, J=1.2 Hz, 8.0 Hz, 8.8 Hz), 7.43 (1H, ddd, J=5.6 Hz, 8.0 Hz), 7.88 (1H, dd); MW 193.18 (C$_{10}$H$_8$O$_2$NF); Mass spectrum EI-MS m/z 193 (M)$^+$.

Synthesis Example 44c 5-Fluoro-3.4-dihydro-2H-isoquinolin-1-one

Ethanol and Raney nickel (Aldrich) were added to 2-cyanomethyl-3-fluoro-benzoic acid methyl ester (3.3 g, 17 mmol) to carry out catalytic reduction under ordinary pressure at 50° C. for 7 hours and then at room temperature for 15 hours. Raney nickel was removed from the reaction solution by filtration, the solvent was removed by evaporation under a reduced pressure, and the thus obtained material was separated and purified by a silica gel column chromatography to obtain 2.1 g (13 mmol, 74% in yield) of the title compound.

$^1$H-NMR (CDCl$_3$): δ 3.03 (2H, t, J=6.8 Hz), 3.57–3.61 (2H, m), 6.18 (1H, br s), 7.19–7.36 (2H, m), 7.89 (1H, d, J=7.8 Hz); MW 165.17 (C$_9$H$_8$NOF); Mass spectrum EI-MS m/z 165 (M)$^+$.

Synthesis Example 45c (the Inventive Compound) 2a-(4-(5-Fluoro-1,2,3,4-tetrahydro-isoquinolin-2-yl)-butyl)-2a,3,4,5-tetrahydro-1H-benz[cd]indol-2-one 5-Fluoro-3,4-dihydro-2H-isoquinolin-1-one (200 mg, 1.2 mmol) was dissolved in anhydrous tetrahydrofuran (6 ml), and the solution was mixed with Red-Al (Aldrich, 65% toluene solution, 6.1 mmol) and stirred at roar temperature for 18 hours. Water was slowly added to the reaction solution, and celite filtration was carried out when foaming started. The reaction product was extracted from the filtrate with ethyl acetate, and the reaction product was extracted from the extract with dilute hydrochloric acid. The water layer was alkalified with sodium hydroxide aqueous solution, and the reaction product was extracted therefrom with ethyl acetate. The extract was washed with saturated brine and dried with anhydrous magnesium sulfate, and then the solvent was removed by evaporation under a reduced pressure to obtain crude 5-fluoro-3,4-dihydro-2H-isoquinoline. The crude 5-fluoro-3,4-dihyrdro-2H-isoquinoline was dissolved in anhydrous N,N-dimethylformamide (3 ml), and the solution was mixed with 2a-(4-bromobutyl)-2a,3,4,5-tetrahydro-1H-benz[cd]indol-2-one (370 mg, 1.2 mmol) and potassium carbonate (250 mg, 1.8 mmol) and stirred at room temperature for 18 hours. The reaction solution was mixed with water, the reaction product was extracted with ethyl acetate, and the extract was washed with water and saturated brine and dried with anhydrous magnesium sulfate. The solvent was removed by evaporation from the extract under a reduced pressure, and the thus obtained material was separated and purified by a silica gel column chromatography to obtain 55 mg (0.14 mmol, 12% in yield) of the title compound.

$^1$H-NMR (CDCl$_3$): δ 1.04–1.17 (1H, m), 1.24–1.42 (2H, m), 1.45–1.62 (2H, m), 1.77–1.93 (3H, m), 2.06–2.19 (2H, m), 2.34–2.47 (2H, m), 2.59–2.69 (3H, m), 2.76–2.89 (3H, m), 3.53 (2H, s), 6.66 (1H, d, J=7.6 Hz), 6.77–6.84 (3H, m), 7.03–7.13 (2H, m), 7.19 (1H, br s); MW 378.49 (C$_{24}$H$_{27}$N$_2$OF); Mass spectrum EI-MS m/z 378 (M)$^+$.

By dissolving the thus obtained free compound in hydrochloric acid-saturated methanol, its hydrochloride was obtained. MW 414.95 (C$_{24}$H$_{28}$ClN$_2$OF); Mass spectrum TSP m/z 379 (M−Cl)$^+$.

Synthesis Example 46c 3-Methyl-4,5,6,7-tetrahydro-thieno[3,2-c]pyridine 5-t-Butoxycarbonyl-3-methyl-4,5,6,7-tetrahydro-thieno[3,2-c]pyridine (150 mg, 0.49 mmol) was dissolved in chloroform (1 ml), and the solution was mixed with hydrochloric acid methanol solution (2 ml), stirred at room temperature for 8 hours, further mixed with concentrated hydrochloric acid (1 ml) and stirred for 16 hours. The solvent was removed by evaporation from the reaction solution under a reduced pressure, and the thus obtained residue was mixed with 47% hydrobromic acid (6 ml) and stirred at 140° C. for 4 hours. The reaction solution was returned to room temperature and alkalified by adding sodium hydroxide aqueous solution and then the reaction product was extracted there from with ethyl acetate. The ethyl acetate layer was washed with saturated brine and dried with anhydrous magnesium sulfate, and then the solvent was removed by evaporation under a reduced pressure to obtain 68 mg (0. 44 mmol, 90% in yield) of the title compound. MW 153.24 (C$_8$H$_{11}$NS); Mass spectrum EI-MS m/z 153 (M)$^+$.

Synthesis Example 47c (the Inventive Compound) 2a-(4-(3-Methyl-4,5,6,7-tetrahydro-thieno[3,2-c]pyridin-5-yl)butyl)-2a,3,4,5-tetrahydro-1H-benz[cd]indol-2-one This was synthesized by the same method of Synthesis Example 17c, except that 3-methyl-4,5,6,7-tetrahydro-thieno[3,2-c]pyridine (0.65 mmol) was used instead of 4,5,6,7-tetrahydro-thieno[3,2-c]pyridine (yield, 77%).

$^1$H-NMR (CDCl$_3$): δ 1.06–1.17 (1H, m), 1.25–1.41 (2H, m), 1.45–1.63 (2H, m), 1.77–1.94 (3H, m), 2.03–2.19 (5H, m), 2.40–2.52 (2H, m), 2.60–2.71 (3H, m), 2.79–2.89 (3H, m), 3.34 (2H, s), 6.65–6.67 (2H, m), 6.80 (1H, d, J=7.6 Hz), 7.11 (1H, dd, J=7.8 Hz), 7.23 (1H, br s); MW 380.55 (C$_{23}$H$_{28}$N$_2$OS); Mass spectrum TSP m/z 381 (M+H)$^+$.

By dissolving the thus obtained free compound in hydrochloric acid-saturated methanol, its hydrochloride was obtained. MW 417.01 (C$_{23}$H$_{29}$ClN$_2$OS); Mass spectrum TSP m/z 381 (M−Cl)$^+$.

Synthesis Example 48c 4,5,6,7-Tetrahydro-thieno[3,2-c]pyridine

Under ice-cooling, 10% sodium hydroxide aqueous solution (10 ml) was added dropwise to ethanol solution (200 ml) of 3-thiophene aldehyde (11 g, 98 mmol) and nitromethane (6.0 g, 98 mmol). After the dropwise addition, the reaction solution was added dropwise to 5 N hydrochloric acid, and the thus formed precipitate was collected by filtration, washed with water and then dried to obtain crude 2-(3-thieno)-1-nitroethylene as yellow powder (yield, 10 g). At room temperature, diethyl ether solution (60 ml) of the crude 2-(3-thieno)-1-nitroethylene (1.55 g, 10 mmol) was added dropwise to diethyl ether suspension (20 ml) of lithium aluminum hydride (760 mg, 20 mmol), spending 40 minutes, and then the mixture was stirred for 20 minutes. Cold water was added to the reaction solution in small portions, and celite filtration was carried out when precipitate was formed. The precipitate was washed with ethyl acetate, combined with the filtrate, washed with saturated brine and dried with anhydrous magnesium sulfate, and then the solvent was removed by evaporation under a reduced pressure. The residue was mixed with water (1.1 ml) and 37% formaldehyde aqueous solution (620 mg, 10 mmol) and vigorously stirred at 100° C. for 3 hours. The solvent was removed by evaporation from the reaction solution under a reduced pressure, and the thus obtained residue was mixed with 5 N hydrochloric acid (2.2 ml) and concentrated hydrochloric acid (0.22 ml) and vigorously stirred at room temperature for 3 hours. The reaction solution was alkalified by adding sodium hydroxide aqueous solution, and the reaction product was extracted therefrom with ethyl acetate, washed with saturated brine and dried using anhydrous magnesium sulfate. The solvent was removed by evaporation from the organic layer under a reduced pressure, and the thus obtained material was separated and purified by a silica gel column chromatography to obtain 310 mg (2.2 mmol, 22% in yield) of the title compound.

$^1$H-NMR (CDCl$_3$): δ 1.85 (1H, br s), 2.65–2.68 (1H, m), 3.12 (1H, t, J=5.8 Hz), 4.04 (2H, s), 6.79 (1H, d, J=4.9 Hz), 7.11 (1H, d); MW 139.22 (C$_7$H$_9$NS); Mass spectrum EI-MS m/z 139 (M)$^+$.

Synthesis Example 49c (the Inventive Compound) 2a-(4-(4,5,6,7-Tetrahydro-thieno[2,3-c]pyridin-6-yl)-butyl)-2a,3,4,5-tetrahydro-1H-benz[cd]indol-2-one This was synthesized by the same method of Synthesis Example 17c, except that 4,5,6,7-tetrahydro-thieno[2,3-c]pyridine was used instead of 4,5 6,7-tetrahydro-thieno[3,2-c]pyridine (yield, 54%).

$^1$H-NMR (CDCl$_3$): δ 1.03–1.16 (1H, m), 1.22–1.56 (4H, m), 1.76–1.93 (3H, m), 2.04–2.20 (2H, m), 2.38–2.50 (2H, m), 2.60–2.72 (5H, m), 2.79–2.89 (1H, m), 3.66 (2H, s), 6.66 (1H, d, J=7.6 Hz), 6.74 (1H, d, J=5.1 Hz), 6.80 (1H, d, J=7.8 Hz), 7.06 (1H, d), 7.11 (1H, dd), 7.32 (1H, br s); MW 366.52 (C$_{22}$H$_{26}$N$_2$OS); Mass spectrum EI-MS m/z 366 (M)$^+$.

Synthesis Example 50c (the Inventive Compound) 2a-(4-(2,3-Dimethyl-4,5,6,7-tetrahydro-thieno[2,3-c]pyridin-5-yl)-butyl)-2a,3,4,5-tetrahydro-1H-benz[cd]indol-2-one A mixture of 5-t-butoxycarbonyl-2,3-dimethyl-4,5,6,7-tetrahydro-thieno[3,2-c]pyridine with 5-t-butoxycarbonyl-3-methyl-4,5,6,7-tetrahydro-thieno[3,2-c]pyridine was obtained by carrying out the same synthesis method of Synthesis Example 35c, except that 5-t-butoxcarbonyl-3-methyl-4,5,6,7-tetrahydro-thieno[3,2-c]pyridine was used instead of 5-t-butoxycarbonyl-4,5,6,7-tetrahydro-thieno[3,2-c]pyridine.

This mixture was dissolved in hydrochloric acid methanol solution and stirred for two nights to effect deprotection, thereby obtaining a mixture of 2,3-dimethyl-4,5,6,7-tetrahydro-thieno[3,2-c]pyridine with 3-methyl-4,5,6,7-tetrahydro-thieno[3,2-c]pyridine.

The title compound was obtained (yield, 6.8%) by carrying out its synthesis by the same method of Synthesis Example 37c, except that the mixture of 2,3-dimethyl-4,5,6,7-tetrahydro-thieno[3,2-c]pyridine with 3-methyl-4,5,6,7-tetrahydro-thieno[3,2-c]pyridine was used instead of 2-methyl-4,5,6,7-tetrahydro-thieno[3,2-c]pyridine.

$^1$H-NMR (CDCl$_3$): δ 1.03–1.18 (1H, m), 1.23–1.57 (4H, m), 1.77–1.94 (6H, m), 2.03–2.19 (2H, m), 2.27 (3H, s), 2.38–2.50 (2H, m), 2.60–2. 90 (6H, m), 3.30 (2H, s), 6.66 (2H, d, J=7.3 Hz), 6.80 (1H, d, J=7.8 Hz), 7.11 (1H, dd), 7.19 (1H, br s); MW 394.58 (C$_{24}$H$_{30}$N$_2$OS); Mass spectrum EI-MS m/z 394 (M)$^+$.

4. Synthesis examples of the compound (1) of the invention having group (d) or (e) and its production intermediate Synthesis Example 1d 2a-(3-Bromopropyl)-2a,3,4,5-tetrahydro-1H-benz[cd]indol-2-one 2a,3,4,5-Tetrahydro-1H-benz[cd]indol-2-one (1.0 g, 5.8 mmol) was dissolved in anhydrous N,N-dimethylformamide (40 ml), and the solution was mixed with sodium hydride (230 mg, 5.8 mmol) and stirred at 60° C. for 1 hour. The reaction solution was mixed with 1,3-dibramopropane (1.8 ml, 17 mmol) and again stirred for 2 hours. The solvent was removed by evaporation under a reduced pressure, and ethyl acetate, water and hydrochloric acid (1 N) were added to the resulting residue. The reaction product was extracted with ethyl acetate, washed with saturated brine and then dried with anhydrous sodium sulfate, and the material obtained by evaporating the solvent under a reduced pressure was separated and purified by a silica gel column chromatography to obtain 150 mg (0.51 mmol, 8.8% in yield) of the title compound.

$^1$H-NMR (CDCl$_3$): δ 1.32–1.44 (1H, m), 1.62–1.73 (1H, m), 1.81–2.03 (1H, m), 2.08–2.22 (2H, m), 2.62–2.71 (1H, m), 2.83–2.92 (1H, m), 3.24–3.34 (2H, m), 6.69 (1H, d, J=7.6 Hz), 6.82 (1H, d, J=8.0 Hz), 7.13 (1H, dd), 7.70 (1H, brs); MW 294.19 (C$_{14}$H$_{16}$BrNO); Mass spectrum EI-MS m/z 293:295=1:1 (M)$^+$.

Synthesis Example 2d 2a-(4-Pentenyl)-2a,3,4,5-tetrahydro-1H-benz[cd]indol-2-one 2a,3,4,5-Tetrahydro-1H-benz[cd]indol-2-one (4.0 g, 23 mmol) was dissolved in anhydrous N,N-dimethylformamide (100 ml), and the solution was mixed with sodium hydride (760 mg, 190 mmol) and stirred at 0° C. for 1 hour. The reaction solution was mixed with 1-bromopentene (3.8 ml, 25 mmol) and stirred at −40° C. for 2 hours. Ethyl acetate, water and hydrochloric acid (1 N) were added to the reaction solution. The reaction product was extracted with ethyl acetate, washed with saturated brine and then dried with anhydrous sodium sulfate, and the material obtained by evaporating the solvent under a reduced pressure was separated and purified by a silica gel column chromatography to obtain 2.7 g (11 mmol, 49% in yield) of the title compound.

$^1$H-NMR (CDCl$_3$): δ 1.05–1.22 (1H, m), 1.31–1.47 (2H, m), 1.73–1.89 (3H, m), 1.89–2.01 (2H, m), 2.06–2.19 (2H, m), 2.59–2.69 (1H, m), 2.79–2.89 (1H, m), 4.87–4.95 (2H, m), 5.68 (1H, m), 6.67 (1H, d, J=7.8 Hz), 6.80 (1H, d, J=7.8 Hz), 7.11 (1H, dd), 7.49 (1H, br s); MW 241.33 (C$_{16}$H$_{19}$NO); Mass spectrum EI-MS m/z 241 (M)$^+$.

Synthesis Example 3d 2a-(3-Formylpropyl)-2a,3,4,5-tetrahydro-1H-benz[cd]indol-2-one In a shaded container, 2a-(4-pentenyl)-2a,3,4,5-tetrahydro-1H-benz[cd]indol-2-one (1.3 g, 5.3 mmol) and N-methylmorpholine oxide (1.9 g, 16 mmol) were dissolved in a mixed solvent of 1,4-dioxane (20 ml) with water (10 ml), and the solution was mixed with osmium tetroxide (4% aqueous solution 3.4 ml, 0.53 mmol) and stirred at room temperature for 2 hours. The reaction solution was mixed with rater (80 ml), the reaction product was extracted with ethyl acetate, washed with saturated brine and dried with anhydrous sodium sulfate, and then the solvent was removed by evaporation under a reduced pressure. The residue was dissolved in a mixed solvent of 1,4-dioxane (20 ml) with water (10 ml), and the solution was mixed with sodium periodate (2.6 g, 12 mmol) and stirred as such for 2.5 hours. The reaction solution was mixed with water (100 ml), and the reaction product was extracted with ethyl acetate, washed with saturated brine and dried with anhydrous sodium sulfate. By evaporating the solvent from the extract under a reduced pressure, 1.3 g (5.3 mmol 100% in yield) of the title compound was obtained.

$^1$H-NMR (CDCl$_3$): δ 1.21–1.50 (2H, m), 1.55–1.70 (1H, m), 1.75–1.91 (1H, m), 2.06–2.19 (2H, m), 2.27–2.42 (2H, m), 2.60–2.70 (1H, m), 2.79–2.90 (1H, m), 6.68 (1H, d, J=7.8 Hz), 6.81 (1H, d, J=7.8 Hz), 7.12 (1H, dd), 7.56 (1H, br s), 9.66 (1H, s); MW 243.31 (C$_{15}$H$_{17}$NO$_2$); Mass spectrum EI-MS m/z 243 (M)$^+$.

Synthesis Example 4d 1-Indanol

1-Indanone (2.5 g, 19 mmol) was dissolved in ethanol (25 ml), and the solution was mixed with sodium borohydride (790 mg, 21 mmol) and stirred at room temperature for 3 hours. The reaction solution was mixed with ethyl acetate, washed with hydrochloric acid (1 N) and saturated brine and dried with anhydrous sodium sulfate, the solvent was removed by evaporation under a reduced pressure, and the thus obtained material was separated and purified by a silica gel column chromatography to obtain 2.4 g (18 mmol, 93%) of the title compound.

$^1$H-NMR (CDCl$_3$): δ 1.74 (1H, br s), 1.91–1.99 (1H, m), 2.45–2.54 (1H, m), 2.78–2.86 (1H, m), 3.03–3.10 (1H, m), 5.20 (1H, br s), 7.22–7.27 (3H, m), 7.42 (1H, d, J=5.6 Hz); MW 134.18 (C$_9$H$_{10}$O); Mass spectrum EI-MS m/z 134 (M)$^+$.

Synthesis Example 5d 1-t-Butoxycarbonyl-4-(1-indanyl)-piperazine

1-Indanol (2.3 g, 17 mmol) was dissolved in chloroform (25 ml), and the solution was mixed with thionyl chloride (1.4 ml, 19 mmol) and stirred at 0° C. for 30 minutes and then at room temperature for 30 minutes. The solvent was removed by evaporation from the reaction solution under a reduced pressure, and the thus obtained residue was mixed with t-butoxycarbonylpiperazine (3.1 g, 17 mmol), potassium carbonate (6.0 g, 48 mmol) and potassium iodide (2.8 g, 17 mmol) and stirred overnight at 100° C. in methyl ethyl ketone (100 ml). The reaction solution was mixed with water, the reaction product was extracted with ethyl acetate, washed with water and saturated brine and dried with anhydrous sodium sulfate, the solvent was removed by evaporation under a reduced pressure, and the thus obtained material was separated and purified by a silica gel column chromatography to obtain 3.6 g (12 mmol, 72%) of the title compound.

$^1$H-NMR (CDCl$_3$): δ 1.45 (9H, s), 2.03–2.10 (2H, m), 2.39–2.51 (4H, m), 2.78–2.98 (2H, m), 3.36–3.49 (4H, m), 4.35 (1H, dd, J=6.8 Hz, 7.1 Hz), 7.17–7.23 (3H, m), 7.32–7.36 (1H, m); MW 302.42 (C$_{18}$H$_{26}$N$_2$O$_2$); Mass spectrum EI-MS m/z 302 (M)$^+$.

Synthesis Example 6d 1-(1-Indanyl)-piperazine Hydrochloride 1-t-Butoxycarbonyl-4-(1-indanyl)piperazine (2.4 g, 7.9 mmol) was dissolved in ethyl acetate (6 ml), and the solution was mixed with hydrochloric aid-saturated methanol (20 ml) and stirred at room temperature for 5.5 hours. The solvent was removed by evaporation from the reaction solution under a reduced pressure, and the resulting residue was washed with diisopropyl ether and dried to obtain 2.2 g (7.9 mmol, 100%).

$^1$H-NMR (CDCl$_3$): δ 2.38–2.50 (1H, m), 2.88–3.00 (1H, m), 3.10–3.76 (10H, m), 5.03 (1H, br s), 7.31–7.44 (3H, m), 7.83 (1H, d, J=7.3 Hz), 12.48 (1H, br s); MW 274.22 (C$_{13}$H$_{19}$Cl$_2$N$_2$); Mass spectrum EI-MS m/z 202 (M)$^+$.

Synthesis Example 7d (the Inventive Compound) 2a-(4-(4-(1-Indanyl)-piperazin-1-yl)butyl)-2a,3,4,5-tetrahydro-1H-benz[cd]indol-2-one 2a-(3-Formylpropyl)-2a,3,4,5-tetrahydro-1H-benz[cd]indol-2-one (210 mg, 0.90 mmol), 1-(1-indanyl)piperazine hydrochloride (270 mg, 1.0 mmol), acetic acid (540 mg, 9.0 mmol) and sodium triacetoxyborohydride (380 mg, 1.8 mmol) were stirred at room temperature for 20 hours in 1,2-dichloroethane (3 ml). The reaction solution was mixed with ethyl acetate (80 ml), washed with sodium hydroxide aqueous solution (1 N) and saturated brine and dried with anhydrous sodium sulfate, the solvent was removed by evaporation under a reduced pressure, and the thus obtained material was separated and purified by a silica gel column chromatography to obtain 430 mg (1.0 mmol, 100% in yield) of the title compound.

$^1$H-NMR (CDCl$_3$): δ 1.00–1.11 (1H, m), 1.24–1.52 (4H, m), 1.72–1.88 (3H, m), 2.04–2.16 (4H, m), 2.22–2.68 (11H, m), 2.75–2.96 (3H, m), 4.32–4.35 (1H, m), 6.65 (1H, d, J=7.8 Hz), 6.80 (1H, d, J=7.8 Hz), 7.11 (1H, dd), 7.15–7.22 (3H, m), 7.28–7.36 (2H, m); MW 429.61 (C$_{28}$H$_{35}$N$_{30}$); Mass spectrum EI-MS m/z 429 (M)$^+$.

By dissolving the thus obtained free compound in hydrochloric acid-saturate. methanol, its hydrochloride was obtained. MW 441.02 (C$_{28}$H$_{37}$Cl$_2$N$_3$O); Mass spectrum EI-MS m/z 429 (M–2HCl)$^+$.

Synthesis Example 8d 1-t-Butoxycarbonyl-4-(1,2,3,4-tetrahydronapthalen-1-yl)piperazine This was synthesized by the same method of Synthesis Example 5d, except that 1,2,3,4-tetrahydro-1-naphthol was used instead of 1-indanol (yield, 85%).

$^1$H-NMR (CDCl$_3$): δ 1.45 (9H, s), 1.61–1.71 (2H, m), 1.89–2.02 (2H, m), 2.40–2.48 (2H, m), 2.52–2.60 (2H, m), 2.67–2.82 (2H, m), 3.38–3.50) (4H, m), 3.80–3.86 (1H, m), 7.04–7.07 (1H, m), 7.10–7.18 (3H, m), 7.68–7.70 (1H, m); MW 316.44 (C$_{19}$H$_{28}$N$_2$O$_2$); Mass spectrum EI-MS m/z 316 (M)$^+$.

Synthesis Example 9d 1-(1,2,3,4-Tetrahydronaphthalen-1-yl)piperazine

This was synthesized by the same method of Synthesis Example 6d, except that 1-t-butoxycarbonyl-4-(1,2,3,4-tetrahydronaphthalen-1-yl)piperazine was used instead of 1-t-butoxycarbonyl-4-(1-indanyl)piperazine (yield, 61%).

$^1$H-NMR (CDCl$_3$): δ 1.62–1.76 (2H, m), 1.90–2.03 (2H, m), 2.44–2.52 (2H, m), 2.58–2.65 (2H, m), 2.70–2.85 (2H, m), 2.85–2.94 (4H, m), 3.75–3.80 (1H, m), 7.04 (1H, d, J=7.3 Hz), 7.09–7.17 (3H, m), 7.70 (1H, d, J=7.3 Hz); MW 216.33 (C$_{14}$H$_{20}$N$_2$); Mass spectrum EI-Ms m/z 216 (M)$^+$.

Synthesis Example 10d (the Inventive Compound) 2a-(4-(4-(1,2,3,4-Tetrahydronaphthalen-1-yl)-piperazin-1-yl)butyl)-2a,3,4,5-tetrahydro-1H-benz[cd]indol-2-one This was synthesized by the same method of Synthesis Example 7d, except that 1-(1,2,3,4-tetrahydronaphthalen-1- yl)piperazine was used instead of 1-(1-indanyl)piperazine hydrochloride (yield, 91%).

$^1$H-NMR (CDCl$_3$): δ 1.00–1.12 (1H, m), 1.23–1.50 (4H, m), 1.63–1.71 (2H, m) 1.71–1.88 (3H, m), 1.88–2.02 (2H, m), 2.03–2.15 (2H, m), 2.18–2.30 (2H, ), 2.30–2.53 (6H, m), 2.53–2.88 (6H, m), 3.74–3.82 (1H, m), 6.66 (1H, d, J=7.6 Hz), 6.80 (1H, d, J=7.8 Hz), 7.01–7.15 (4H, m), 7.37 (1H, br s), 7.65 (1H, d, J 7.1 Hz); MW 443.63 (C$_{29}$H$_{37}$N$_3$O); Mass spectrum EI-MS m/z 443 (M)$^+$.

Synthesis Example 11d 4-Thiochromanol

This was synthesized by the same method of Synthesis Example 4d, except that 4-thiochromanone was used instead of 1-indanone (yield, 94%).

$^1$H-NMR (CDCl$_3$): δ 1.98 (1H, br s), 2.00–2.08 (1H, m), 2.28–2.35 (1H, m), 2.81–2.87 (1H, m), 3.30 (1H, dt, J=2.9 Hz, 12 Hz), 4.76–4.78 (1H, m), 7.03–7.07 (1H, m), 7.10–7.17 (2H, m), 7.29–7.33 (1H, m); MW 166.24 (C$_9$H$_{10}$OS); Mass spectrum EI-MS m/z 166 (M)$^+$.

Synthesis Example 12d 1-t-Butoxycarbonyl-4-(thiochromanyl)piperazine

This was synthesized by the same method of Synthesis Example 5d, except that 4-chromanol was used instead of 1-indanol (yield, 79%).

$^1$H-NMR (CDCl$_3$): δ 1.45 (9H, s), 2.05–2.12 (1H, m), 2.15–2.24 (1H, m), 2.32–2.40 (2H, m), 2.51–2.64 (2H, br s), 2.97–3.05 (1H, m), 3.13–3.21 (1H, m), 3.36–3.48 (4H, m), 3.62 (1H, dd, J=3.6 Hz, 8.0 Hz), 6.99–7.04 (1H, m), 7.09–7.11 (2H, m), 7.43–7.45 (1H, m)); MW 334.48 (C$_{18}$H$_{26}$N$_2$O$_2$S); Mass spectrum EI-MS m/z 334 (M)$^+$.

Synthesis Example 13d 1-(4-Thiochromanyl) piperazine Hydrochloride

This was synthesized by the same method of Synthesis Example 6d, except that 1-t-butoxycarbonyl-4-(4-thiochromanyl)piperazine was used instead of 1-t-butoxycarbonyl-4-(1-indanyl)piperazine (yield, 79%).

MW 307.28 (C$_{13}$H$_{20}$Cl$_2$N$_2$S); Mass spectrum EI-MS m/z 235 (M−2HCl+H)$^+$.

Synthesis Example 14d (the Inventive Compound) 2a-(4-(4-(4-Thiochromanyl)-piperazin-1-yl)butyl)-2a,3,4,5-tetrahydro-1H-benz[cd]indol-2-one This was synthesized by the same method of Synthesis Example 7d, except that 1-(4-thiochromanyl)piperazine hydrochloride was used instead of 1-(1-indanyl)piperazine hydrochloride (yield, 79%).

$^1$H-NMR (CDCl$_3$): δ 1.09–1.12 (1H, m), 1.24–1.46 (4H, m), 1.72–1.90 (3H, m), 2.00–2.14 (3H, m), 2.14–2.30 (3H, m), 2.39 (6H, br s), 2.56–2.68 (3H, m), 2.78–2.87 (1H, m), 2.95–3.02 (1H, m), 3.13–3.20 (1H, m), 3.56 (1H, dd, J=3.4 Hz, 8.0 Hz), 6.66 (1H, d, J=7.5 Hz), 6.80 (1H, d, J=7.8 Hz), 6.97–7.02 (1H, m), 7.06–7.13 (3H, br s), 7.41 (2H, m); MW 461.67 (C$_{28}$H$_{35}$N$_3$OS); Mass spectrum EI-MS m/z 461 (M)$^+$.

Synthesis Example 15d 4-Chromanol

This was synthesized by the same method of Synthesis Example 4d, except that chromanone was used instead of 1-indanone (yield, 100%).

$^1$H-NMR (CDCl$_3$): δ 1.95–2.02 (1H, m), 2.05–2.13 (1H, m), 2.15 (1H, d, J=4.4 Hz), 4.20–4.28 (2H, m), 4.74 (1H, dd, J=4.4 Hz, 8.5 Hz), 6.83 (1H, dd, J=1.2 Hz, 8.3 Hz), 6.90 (1H, dt, J=1.2 Hz, 7.6 Hz), 7.16–7.23 (1H, m), 7.28 (1H, dd, J=1.7 Hz, 7.6 Hz); MW 150.18 (C$_9$H$_{10}$O$_2$); Mass spectrum EI-MS m/z 150 (M)$^+$.

Synthesis Example 16d 1-t-Butoxycarbonyl-4-(4-chromanyl)piperazine

This was synthesized by the same method of Synthesis Example 5d, except that 4-chromanol was used instead of 1-indanol (yield, 58%).

$^1$H-NMR (CDCl$_3$): δ 1.46 (9H, s), 1.89–1.97 (1H, m), 2.01–2.11 (1H, m), 2.38–2.48 (2H, br s), 2.53–2.65 (2H, br s), 3.37–3.48 (4H, m), 3.85–3.90 (1H, m), 4.09–4.17 (1H, m), 4.32–4.38 (1H, m), 6.79 (1H, dd, J=1.2 Hz, 8.2 Hz), 6.88 (1H, dt, J=1.2 Hz, 7.3 Hz), 7.10–7.15 (1H, m), 7.46–7.50 (1H, m); MW 318.42 (C$_{18}$H$_{26}$N$_2$O$_3$); Mass spectrum EI-MS m/z 318 (M)$^+$.

Synthesis Example 17d 1-(4-Chromanyl)piperazine Hydrochloride

This was synthesized by the same method of Synthesis Example 6d, except that 1-t-butoxycarbonyl-4-(chromanyl) piperazine was used instead of 1-t-butoxycarbonyl-4-(1-indanyl)piperazine (yield, 50%). MW 291.22 (C$_{13}$H$_{20}$Cl$_2$N$_2$O); Mass spectrum EI-MS m/z 218 (M−2HCl)$^+$.

Synthesis Example 18d (the Inventive Compound) 2a-(4-(4-(4-Chromanyl)-piperazin-1-yl)butyl)-2a,3,4,5-tetrahydro-1H-benz[cd]indol-2-one This was synthesized by the same method of Synthesis Example 7d, except that 1-(4-chromanyl)piperazine hydrochloride was used instead of 1-(1-indanyl)piperazine hydrochloride (yield, 75%).

$^1$H-NMR (CDCl$_3$): δ 1.00–1.11 (1H, m), 1.23–1.48 (4H, m), 1.73–1.95 (4H m), 2.03–2.15 (3H, m), 2.17–2.30 (2H, m), 2.30–2.55 (6H, m), 2.57–2.68 (3H, m), 2.79–2.90 (1H, m), 3.81 (1H, dd, J=5.5 Hz, 8.5 Hz), 4.07–4.16 (1H, m), 4.29–4.38 (1H, m), 6.67 (1H, d, J=7.6 Hz), 6.76 (1H, d, J=8.3 Hz), 6.79 (1H, d, J=7.8 Hz), 6.85 (1H, dd, J=7.3 Hz, 7.6 Hz), 7.10 (2H, m), 7.44 (1H, d), 7.93 (1H, s); MW 445.60 (C$_{28}$H$_{35}$N$_3$O$_2$); Mass spectrum EI-MS m/z 445 (M)$^+$.

Synthesis Example 19d 6,7,8,9-Tetrahydro-5H-benzocyclohepten-5-ol

This was synthesized by the same method of Synthesis Example 4d, except that 1-benzosuberone was used instead of 1-indanone (yield, 92%).

$^1$H-NMR (CDCl$_3$): δ 1.49–1.64 (2H, m), 1.78–1.84 (2H, m), 1.94–2.14 (2H, m), 2.69–2.80 (1H, m), 2.89–2.95 (1H, m), 4.93–4.95 (1H, m), 7.09–7.23 (3H, m), 7.44 (1H, d, J=7.3 Hz); MW 162.23 (C$_{11}$H$_{14}$O); Mass spectrum EI-MS m/z 162 (M)$^+$.

Synthesis Example 20d 1-t-Butoxycarbonyl-4-(6,7,8,9-tetrahydro-5H-benzocyclohepten-5-yl)piperazine This was synthesized by the same method of Synthesis Example 5d, except that 6,7,8,9-tetrahydro-5H-benzocyclohepten-5-ol was used instead of 1-indanol (yield, 31%).

$^1$H-NMR (CDCl$_3$): δ 1.33–1.50 (10H, m), 1.60–1.70 (2H, m), 1.89–1.98 (1H, 2.02–2.20 (4H, m), 2.34–2.52 (3H, m), 3.15 (1H, d, J=6.1 Hz), 3.31–3.35 (5H, m), 7.04–7.22 (4H, m); MW 330.47 (C$_{20}$H$_{30}$N$_2$O$_2$); Mass, spectrum EI-MS m/z 330 (M)$^+$.

Synthesis Example 21d (the Inventive Compound) 2a-(4-(4-(6,7,8,9-Tetrahydro-5H-benzocyclohepten-5-yl)-piperazin-1-yl)butyl)-2a,3,4,5-tetrahydro-1H-benz[cd]indol-2-one 1-t-Butoxycarbonyl-4-(6,7,8,9-tetrahydro-5H-benzocyclohepten-5-yl)piperazine (340 mg, 1.0 mmol) was dissolved in 10% hydrochloric acid methanol (4 ml) and stirred at 40° C. for 3.5 hours. The solvent was removed by evaporation under a reduced pressure, and the thus obtained residue was mixed with 2a-(4-bromobutyl)-2a,3,4,5-tetrahydro-1H-benz[cd]indol-2-one (310 mg, 1.0 mmol) and potassium carbonate (490 mg, 3.5 mmol) and stirred overnight at room temperature in N,N-dimethylformamide (3 ml). This was mixed with water, the precipitate was collected by filtration and then the reaction product was extracted from the mother liquid with ethyl acetate. The extract was washed with water and saturated brine and dried with anhydrous sodium hydrogensulfate, the solvent was removed by evaporation under a reduced pressure, and the thus obtained material was separated and purified by a silica gel column chromatography. The thus purified compound was combined with the aforementioned precipitate and thoroughly washed with ethyl acetate to obtain 370 mg (0.81 mmol, 80%) of the title compound.

$^1$H-NMR (CDCl$_3$): δ 0.97–1.10 (1H, m), 1.21–1.50 (5H, m), 1.71–1.93 (4H, m), 1.93–2.69 (16H, m), 2.78–2.88 (1H, m), 3.14 (1H, d, J=5.8 Hz), 3.46 (1H, t, J=7.8 Hz), 6.67 (1H, d, J=7.8 Hz), 6.79 (1H, d, J=7.6 Hz), 7.02–7.12 (5H, m), 7.84–7.88 (1H, m)); MW 457.66 (C$_{30}$H$_{39}$N$_3$O); Mass spectrum EI-MS m/z 457 (M)$^+$.

Synthesis Example 22d 9-Bromo-6,7,8,9-tetrahydrobenzocyclohepten-5-one

1-Benzosuberone (960 mg, 6.0 mmol), N-bromosuccinic acid imide (1.1 g, 6.3 mmol) and azobisisobutyronitrile (99 mg, 0.60 mmol) were stirred overnight at 80° C. in carbon tetrachloride (8 ml). The reaction solution was mixed with chloroform (60 ml), washed with saturated sodium bicarbonate aqueous solution and saturated brine and dried with anhydrous sodium sulfate, the solvent was removed by evaporation under a reduced pressure, and the thus obtained material was separated and purified by a silica gel column chromatography to obtain 770 mg (3.2 mmol, 54%) of the title compound.

$^1$H-NMR (CDCl$_3$): δ 1.98–2.11 (2H, m), 2.22–2.35 (2H, m), 2.45–2.54 (1H, m), 2.70–2.76 (1H, m), 3.18–3.26 (1H, m), 5.57 (1H, dd, J=2.4 Hz, 6.0 Hz), 7.36–7.47 (3H, m), 7.60 (1H, d, J=7.6 Hz); MW 239.11 (C$_{11}$H$_{11}$OBr); Mass spectrum FAB m/z 239:241=1:1 (M+H)$^+$.

Synthesis Example 23d 1-t-Butoxycarbonyl-4-(9-oxo-6,7,8,9-tetrahydro-5H-benzocyclohepten-5-yl)piperazine 9-Bromo-6,7,8,9-tetrahydrobenzocyclohepten-5-one (590 mg, 2.5 mmol), 1-t-butoxycarbonylpiperazine (500 mg, 2.7 mmol) and potassium carbonate (510 mg, 3.7 mmol) were stirred overnight in DMF. The reaction solution was mixed with water, the reaction product was extracted with ethyl acetate, washed with water and saturated brine and dried with anhydrous sodium sulfate, the solvent was removed by evaporation under a reduced pressure, and the thus obtained material was separated and purified by a silica gel column chromatography to obtain 450 mg (1.3 mmol, 53%) of the title compound.

$^1$H-NMR (CDCl$_3$): δ 1.40–1.50 (10H, m), 1.64–1.98 (3H, m), 2.08–2.15 (2H, m), 2.20–2.64 (3H, m), 2.84–2.93 (2H, m), 3.20–3.42 (5H, m), 7.24–7.48 (4H, m)); MW 344.46 (C$_{20}$H$_{28}$N$_{2O3}$); Mass spectrum EI-MS m/z 344 (M)$^+$.

Synthesis Example 24d (the Inventive Compound) 2a-(4-(4-(9-oxo-6,7,8,9-Tetrahydro-5H-benzocyclohepten-5-yl)-piperazin-1-yl)butyl)-2a,3,4,5-tetrahydro-1H-benz[cd]indol-2-one This was synthesized by the same method of Synthesis Example 21d, except that 1-t-butoxycarbonyl-4-(9-oxo-6,7,8,9-tetrahydro-5H-benzocyclohepten-5-yl)piperazine was used instead of 1-t-butoxycarbonyl-4-(6,7,8,9-tetrahydro-5H-benzocyclohepten-5-yl)piperazine (yield, 81%).

$^1$H-NMR (CDCl$_3$): δ 0.93–1.08 (1H, m), 1.20–1.40 (5H, m), 1.55–1.90 (6H, m), 2.00–2.70 (14H, m), 2.75–2.92 (2H, m), 3.27–3.35 (1H, m), 6.65 (1H, d, J=7.8 Hz), 6.79 (1H, d, J=7.6 Hz), 7.10 (1H, dd), 7.23–7.45 (8H, m); MW 471.65 (C$_{30}$H$_{37}$N$_{3O2}$); Mass spectrum EI-MS m/z 471 (M)$^+$.

Synthesis Example 25d 7-Methoxy-1,2,3,4-tetrahydro-1-naphthol

This was synthesized by the same method of Synthesis Example 4d, except 7-methoxytetralone was used instead of 1-indanone (yield, 97%).

$^1$H-NMR (CDCl$_3$): δ 1.70–2.03 (4H, m), 2.61–2.80 (2H, m), 3.80 (3H, s), 4.74 (1H, dd, J=6.1 Hz, 10.7 Hz), 6.78 (1H, dd, J=2.7 Hz, 8.4 Hz), 6.98–7.04 (2H, m); MW 178.23 (C$_{11}$H$_{14}$O$_2$); Mass spectrum EI-MS m/z 178 (M)$^+$.

Synthesis Example 26d 1-t-Butoxycarbonyl-4-(7-methoxy-1,2,3,4-tetrahydronaphthalen-1-yl)-piperazine This was synthesized by the same method of Synthesis Example 5d, except that 7-methoxy-1,2,3,4-tetrahydro-1-naphthol was used instead of 1-indanol (yield, 85%).

$^1$H-NMR (CDCl$_3$): δ 1.46 (9H, s), 1.56–1.68 (2H, m), 1.91–1.99 (2H, m), 2.40–2.48 (2H, m), 2.54–2.61 (2H, m), 2.64–2.70 (2H, m), 3.37–3.49 (4H, m), 3.78–3.83 (4H, m), 6.71 (1H, dd, J=2.9 Hz, 8.3 Hz) 6.97 (1H, d), 7.32 (1H, d); MW 346.47 (C$_{20}$H$_{30}$N$_2$O$_3$); Mass spectrum EI-MS m/z 346 (M)$^+$.

Synthesis Example 27d (the Inventive Compound) 2a-(4-(4-(7-Methoxy-1,2,3,4-tetrahydronaphthalen-1-yl)-piperazin-1-yl)butyl)-2a,3,4,5-tetrahydro-1H-benz[cd]indol-2-one This was synthesized by the same method of Synthesis Example 21d, except that 1-t-butoxycarbonyl-4-(7-methoxy-1,2,3,4-tetrahydronaphthalen-1-yl)piperazine was used instead of 1-t-butoxycarbonyl-4-(6,7,8,9-tetrahydro-5H-benzocyclohepten-5-yl)piperazine (yield, 95%).

$^1$H-NMR (CDCl$_3$): δ 0.99–1.11 (1H, m), 1.25–1.48 (4H, m), 1.55–1.68 (2H, m), 1.75–2.00 (5H, m), 2.04–2.18 (2H, m), 2.18–2.31 (2H, m), 2.31–2.71 (11H, m), 2.79–2.89 (1H, m), 3.73–3.77 (4H, m), 6.68–6.70 (2H, m), 6.79 (1H, d, J=7.8 Hz), 6.95 (1H, d, J=8.5 Hz), 7.10 (1H, dd), 7.28 (1H, d, J=2.7 Hz), 8.44 (1H, br s); MW 473.66 (C$_{30}$H$_{29}$N$_3$O$_2$); Mass spectrum EI-MS m/z 473 (M)$^+$.

Synthesis Example 28d 5,6,7,8-Tetrahydroquinoline N-Oxide 5,6,7,8-Tretrahydroquinoline (2.5 g, 19 mmol) was dissolved in 30% hydrogen peroxide aqueous solution (4 ml) and acetic acid (7.5 ml) and stirred at 90° C. for 6.5 hours. This was further mixed with hydrogen peroxide aqueous solution (4 ml) and stirred overnight. The solvent was removed by evaporation from the reaction solution under a reduced pressure, the resulting residue was neutralized by adding sodium carbonate aqueous solution and then the reaction product was extracted with chloroform, washed with saturated brine and dried with anhydrous sodium sulfate, subsequently evaporating the solvent under a reduced pressure. Diethyl ether was added to the thus obtained residue, and this thus precipitated crystals were collected by filtration, washed thoroughly with diethyl ether and then dried to obtain 1.9 g (13 mmol, 67%) of the title compound.

$^1$H-NMR (CDCl$_3$): δ 1.74–1.80 (2H, m), 1.88–1.94 (2H, m), 2.77 (2H, t, J=6.3 Hz), 2.94 (2H, t, J=6.6 Hz), 6.99–7.05 (2H, m), 8.13 (1H, d, J=5.8 Hz); MW 149.19 (C$_9$H$_{11}$NO); Mass spectrum TSP m/z 150 (M+H)$^+$.

Synthesis Example 29d 8-Acetoxy-5,6,7,8-tetrahydroquinoline 5,6,7,8-Tetrahydroquinoline N-oxide (1.6 g, 11 mmol) was mixed with acetic anhydride (9.2 ml) and stirred at 90° C. for 7 hours. After removing the solvent by evaporation under a reduced pressure, the residue was neutralized with sodium hydroxide aqueous solution (1 N) and the reaction product was extracted with chloroform. The extract was washed with saturated brine and dried with anhydrous sodium sulfate, and then the solvent was removed by evaporation under a reduced pressure and the thus obtained material was separated and purified by a silica gel column chromatography to obtain 690 mg (3.6 mmol, 33%) of the title compound.

$^1$H-NMR (CDCl$_3$): δ 1.80–2.00 (2H, m), 2.01–2.20 (5H, m), 2.71–2.81 (1H, m), 2.83–2.91 (1H, m), 5.98 (1H, t, J=4.6 Hz), 7.16 (1H, dd, J=4.7 Hz, 7.8 Hz), 7.45 (1H, d), 8.49 (1H, d); MW 191.23 (C$_{11}$H$_{13}$NO$_2$); Mass spectrum TSP m/z 192 (M+H)$^+$.

Synthesis Example 30d 8-Hydroxy-5,6,7,8-tetrahydroquinoline

8-Acetoxy-5,6,7,8-tetrahydroquinoline (630 mg, 3.3 mmol) was mixed with 10% hydrochloric acid aqueous solution and stirred overnight while heating under reflux. After returning to room temperature, this was neutralized with sodium hydroxide aqueous solution and the reaction product was extracted with chloroform. The extract was washes with saturated brine and dried with anhydrous sodium sulfate and then the solvent was removed by evaporation under a reduced pressure to obtain 490 mg (3.3 mmol, 100%) of the title compound.

$^1$H-NMR (CDCl$_3$): δ 1.78–1.88 (2H, m), 1.90–2.10 (1H, m), 2.20–2.35 (1H, m), 2.74–2.89 (2H, m), 4.11 (1H, br s), 4.49–4.74 (1H, m), 7.12 (1H, dd, J=4.6 Hz, 7.8 Hz), 7.41 (1H, d), 8.41 (1H, d); MW 149.19 (C$_9$H$_{11}$NO); Mass spectrum EI-MS m/z 149 (M)$^+$.

Synthesis Example 31d 1-t-Butoxycarbonyl-4-(5,6,7,8-tetrahydroquinolin-8-yl)-piperazine This was synthesized by the same method of Synthesis Example 5d, except that 8-hydroxy-5,6,7,8-tetrahydroquinoline was used instead of 1-indanol (yield, 59%).

$^1$H-NMR (CDCl$_3$): δ 1.45 (9H, s), 1.92–2.04 (4H, m), 2.46–2.58 (4H, m) 2.65–2.74 (1H, m), 2.78–2.86 (1H, m), 3.36–3.50 (4 H, m), 3.88 (1H, t, J=6.3 Hz), 7.07 (1H, dd, J=4.9 Hz, 7.7 Hz), 7.37 (1H, d), 8.48 (1H, d); MW 317.43 (C$_{18}$H$_{27}$N$_3$O$_2$); Mass spectrum TSP m/z 318 (M+H)$^+$.

Synthesis Example 32d (the Inventive Compound) 2a-(4-(4-(5,6,7,8-Tetrahydroquinolin-8-yl)-piperazin-1-yl)butyl)-2a,3,4,5-tetrahydro-1H-benz[cd]indol-2-one This was synthesized by the same method of Synthesis Example 21d, except that 1-t-butoxycarbonyl-4-(5,6,7,8-tetrahydroquinolin-8-yl)piperazine was used instead of 1-t-butoxycarbonyl-4-(6,7,8,9-tetrahydro-5H-benzocyclohepten-5-yl)piperazine (yield, 81%).

$^1$H-NMR (CDCl$_3$): δ 0.96–1.09 (1H, m), 1.22–1.47 (4H, m), 1.61–2.17 (10H, m), 2.17–2.30 (2H, m), 2.30–2.73 (9H, m), 2.73–2.89 (2H, m), 3.85 (1H, dd, J=5.8 Hz, 6.8 Hz), 6.65 (1H, d, J=7.8 Hz), 6.78 (1H, d, J=7.8 Hz), 7.05 (1H, dd, J=4.6 Hz, 7.6 Hz), 7.09 (1H, dd), 7.35 (1H, d), 7.88 (1H, d), 8.44–8.46 (1H, m); MW 444.62 (C$_{28}$H$_{36}$N$_4$O); Mass spectrum EI-MS m/z 444 (M)$^+$.

By dissolving the thus obtained free compound in hydrochloric acid-saturated methanol, its hydrochloride was obtained. MW (C$_{28}$H$_{39}$Cl$_3$N$_4$O) 554.00; Mass spectrum EI-MS m/z 444 (M–3HCl).

Synthesis Example 33d 5,6,7,8-Tetrahydroisoquinoline N-Oxide

This was synthesized by the same method of Synthesis Example 28d, except that 5,6,7,8-tetrahydroisoquinoline was used instead of 5,6,7,8-tetrahydroquinoline (yield, 53%).

$^1$H-NMR (CDCl$_3$): δ 1.77–1.86 (4H, m), 2.65–2.80 (4H, m), 6.96 (1H, d, J=6.6 Hz), 7.93–8.00 (2H, m); MW 149.19 (C$_9$H$_{11}$NO);Mass spectrum EI-MS m/z 149 (M)$^+$.

Synthesis Example 34d 5-Acetoxy-5,6,7,8-tetrahydroisoquinoline

This was synthesized by the same method of Synthesis Example 29d, except that 5,6,7,8-tetrahydroisoquinoline N-oxide was used instead of 5,6,7,8-tetrahydroquinoline N-oxide (yield, 40%).

$^1$H-NMR (CDCl$_3$): δ 1.80–2.20 (7H, m), 2.70–2.80 (1H, m), 5.93 (1H, t, J=5.4 Hz), 7.16 (1H, d, J=5.1 Hz), 8.38–8.42 (2H, m); MW 191.23 (C$_{11}$H$_{13}$NO$_2$); Mass spectrum EI-MS m/z 191 (M)$^+$.

Synthesis Example 35d 5-Hydroxy-5,6,7,8-tetrahydroisoquinoline

This was synthesized by the same method of Synthesis Example 30d, except that 5-acetoxy-5,6,7,8-tetrahydroisoquinoline was used instead of 8-acetoxy-5,6,7,8-tetrahydroquinoline (yield, 100%).

$^1$H-NMR (CDCl$_3$): δ 1.80–1.87 (2H, m), 1.97–2.07 (1H, m), 2.08–2.18 (1H, m), 2.55 (1H, br s), 2.70–2.84 (2H, m), 4.74 (1H, br s), 7.39 (1H, d, J=5.1 Hz), 8.33 (1H, m), 8.38 (1H, d); MW 149.19 (C$_9$H$_{11}$NO); Mass spectrum EI-MS m/z 149 (M)$^+$.

Synthesis Example 36d 1-t-Butoxycarbonyl-4-(5,6,7,8-tetrahydroisocuinolin-5-yl)-piperazine This was synthesized by the same method of Synthesis Example 30d, except that 5-hydroxy-5,6,7,8-tetrahydroisoquinoline was used instead of 8-hydroxy-5,6,7,8-tetrahydroquinoline.

$^1$H-NMR (CDCl$_3$): δ 1.46 (9H, m), 1.59–1.75 (2H, m), 1.95–2.09 (2H, m), 2.41–2.57 (2H, m), 2.69–2.78 (2H, m), 3.38–3.50 (4H, m), 3.78–3.8:3 (1H, m), 7.61 (1H, d, J=5.1 Hz), 8.32 (1H, s), 8.36 (1H, d); MW 317.43 (C$_{18}$H$_{27}$N$_3$O$_2$); Mass spectrum EI-MS m/z 317 (M)$^+$.

Synthesis Example 37d (the Inventive Compound) 2a-(4-(4-(5,6,7,8-Tetrahydroisoquinolin-5-yl)-piperazin-1-yl)butyl)-2a,3,4,5-tetrahydro-1H-benz[d]indol-2-one This was synthesized by the same method of Synthesis Example 21d, except that 1-t-butoxycarbonyl-4-(5,6,7,8-tetrahydroisoquinolin-5-yl)piperazine was used instead of 1-t-butoxycarbonyl-4-(6,7,8,9-tetrahydro-5H-benzocyclohepten-5-yl)piperazine yield, 59%).

$^1$H-NMR (CDCl$_3$): δ 1.00–1.11 (1H, m), 1.23–1.46 (1H, m), 1.60–1.90 (7H, m), 1.94–2.18 (3H, m), 2.18–2.77 (12H, m), 2.77–2.89 (1H, m), 3.74–3.77 (1H, m), 6.66 (1H, d, J=7.6 Hz), 6.80 (1H, d, J=7.8Hz), 7.11 (1H, dd), 7.31 (1H, br s), 7.31 (1H, br s), 7.57 (1H, d, J=5.1 Hz), 8.29 (1H, s), 8.33 (1H, d); MW 444.62 (C$_{28}$H$_{36}$N$_4$O); Mass spectrum EI-MS m/z 444 (M)$^+$.

Synthesis Example 38d 4-(1-Hydroxy-1,2,3,4-tetrahydronaphthalen-1-yl)-pyridine Ether solution (50 ml) of 4-bromopyridine (3.2 g, 20 mmol) was cooled using a dry ice-acetone mixture. 1.6 M Butyl lithium hexane solution (16 ml, 26 mmol) was added dropwise to the solution in small portions, and stirred for 30 minutes after completion of the dropwise addition. The reaction solution was mixed with α-tetralone (3.3 g, 23 mmol), returned to room temperature spending 20 minutes and then stirred for 2 hours. Ethyl acetate (100 ml) and water (50 ml) were added to the reaction mixture, and the ethyl acetate layer was separated, washed with water and dried with anhydrous sodium sulfate. The ethyl acetate solution was concentrated under a reduced pressure, diisopropyl ether (30 ml) was added to the resulting residue and then the thus precipitated crystals were collected by filtration to obtain 1.7 g (7.3 mmol, 37% in yield) of the title compound.

$^1$H-NMR (CDCl$_3$): δ 1.85 (1H, m), 2.04 (2H, m), 2.14 (1H, m), 2.42 (1H, br s), 2.9 (2H, m), 6.93 (1H, dd, J=1.0 Hz, 7.8 Hz), 7.12 (1H, t, J=6.3 Hz), 7.21 (2H, m), 7.27 (1H, dd, J=1.6 Hz, 4.5 Hz), 8.51 (1H, dd, J=1.6 Hz, 4.5 Hz); MW 225.29 (C$_{15}$H$_{15}$NO); Mass spectrum EI-MS m/z 225 (M)$^+$.

Synthesis Example 39d 1-(1,2,3,4-Tetrahydronaphthalen-1-yl)-piperidine Hydrochloride Ethanol (20 ml), concentrated hydrochloric acid (1.0 ml) and platinum oxide (50 mg) were added to 1-hydroxy-1-(4-pyridyl)-1,2,3,4-tetrahyonaphthalene (540 mg, 2.4 mmol), and 5 days of reduction reaction was carried out in a stream of hydrogen under 1 atmospheric pressure. The catalyst was removed from the reaction solution, the filtrate was concentrated under a reduced pressure, the residue was dried and mixed with isopropyl alcohol (1.0 ml) and ethyl acetate (10 ml) and then the thus precipitated crystals were collected by filtration to obtain 410 mg (1.9 mmol, 68% in yield) of the title compound.

$^1$H-NMR (CDCl$_3$): δ 1.43 (1H, m), 1.67 (2H, m), 1.78 (2H, m), 1.89 (2H, m), 2.25 (2H, m), 2.60–2.77 (5H, m), 3.28 (2H, t), 7.10 (4H, dd); MW 215.34 (C$_{15}$H$_{21}$N); Mass spectrum EI-MS m/z 215 (M)$^+$.

Synthesis Example 40d (the Inventive Compound) 2a-(4-(4-(1,2,3,4-Tetrahydronaphthalen-1-yl)-piperidin-1-yl)butyl)-2a,3,4,5-tetrahydro-1H-benz[cd]indol-2-one This was synthesized by the same method of Synthesis Example 7a, except that 1-(1,2,3,4-tetrahydronaphthalen-1-yl)piperidine hydrochloride was used instead of 1-indanylpiperazine hydrochloride (yield, 53%).

$^1$H-NMR (CDCl$_3$): δ 1.00–1.10 (1H, m), 1.20–1.50 (4H, m), 1.60–1.90 (14H, m), 2.00–2.25 (4H, m), 2.58–2.77 (4H, m), 2.77–2.95 (3H, m), 6.65 (1H, d, J=7.8 Hz), 6.80 (1H, d, J=7.8 Hz), 7.03–7.15 (5H, m), 7.37 (1H, s); MW 442.64 (C$_{30}$H$_{38}$N$_2$O); Mass spectrum EI-MS m/z 442 (M)$^+$.

Synthesis Example 41d (the Inventive Compound) 2a-(4-(4-(1-Indanyl)-piperazin-1-yl)propyl)-2a,3,4,5-tetrahydro-1H-benz[cd]indol-!-one This was synthesized by the same method of Synthesis Example 21a, except that 2a-(3-bromopropyl)-2a,3,4,5-tetrahydro-1H-benz[cd]indol-2-one was used instead of 2a-(4-bromobutyl)-2a,3,4,5-tetrahydro-1H-benz[cd]indol-2-one, and 1-t-butoxycarbonyl-4-(1-indanyl)piperazine was used instead of 1-t-butoxycarbonyl-4-(6,7,8,9-tetrahydro-5H-benzocyclohepten-5-yl)piperazine (yield, 30%).

$^1$H-NMR (CDCl$_3$): δ 1.30–1.41 (1H, m), 1.44–1.59 (1H, m), 1.75–1.88 (4H, m), 2.03–2.19 (4H, m), 2.19–2.31 (2H, m), 2.31–2.69 (8H, m), 2.75–2.97 (4H, m), 4.32 (1H, m), 6.64 (1H, d, J=7.6 Hz), 6.713 (1H, d, J=7.8 Hz), 7.09 (1H, dd), 7.12–7.25 (3H, m), 7.28–7.38 (2H, m); MW 415.58 (C$_{27}$H$_{33}$N$_3$O); Mass spectrum EI-MS m/z 415 (M)$^+$.

Synthesis Example 42d 2-(1-Benzyl-piperidin-4-yl)-1,2,3,4-tetrahydro-isoquinoline 1,2,3,4-Tetrahydroisoquinoline (700 mg, 5.3 mmol), acetic acid (3.2 g, 5.3 mmol), sodium triacetoxyborohydride (2.2 g, 11 mmol) and benzylpiperidone (1.0 g, 5.3 mmol) were stirred at room temperature for 3.5 hours in dichloroethane (7 ml). The reaction solution was alkalified by adding sodium hydroxide aqueous solution, the reaction product was extracted with ethyl acetate, and the organic layer was washed with water and saturated brine and then dried with anhydrous sodium sulfate. The solvent was removed by evaporation from the organic layer under a reduced pressure, and the thus obtained material was separated and purified by a silica gel column chromatography to obtain 900 mg (3.0 mmol, 56% in yield) of the title compound.

$^1$H-NMR (CDCl$_3$): δ 1.59–1.75 (2H, m), 1.84–1.87 (2H, m), 1.98–2.04 (2H, m), 2.48 (1H, tt, J=3.7 Hz, 11.5 Hz), 2.81–2.92 (4H, m), 2.96–2.99 (2H, m), 3.51 (2H, s), 3.78 (2H, s), 6.98–7.01 (1H, m), 7.06.–7.12 (3H, m), 7.22–7.33 (5H, m); MW 306.45 (C$_{21}$H$_2$N$_2$); Mass spectrum TSP m/z 307 (M+H)$^+$.

Synthesis Example 43d 4-(1,2,3,4-Tetrahydro-isoquinolin-2-yl)piperidine-1-carboxylic Acid Benzyl Ester 2-(1-Benzyl-piperidin-4-yl)-1,2,3,4-tetrahydroisoquinoline (280 mg, 0.90 mmol), benzyloxycarbonyl chloride (310 mg, 1.8 mmol) and potassium bicarbonate (230 mg, 2.3 mmol) were stirred at room temperature for 23 hours in dichloromethane (5 ml). The reaction solution was mixed with dichloromethane, washed with water and saturated brine and the dried with anhydrous sodium sulfate. The solvent was removed by evaporation from the organic layer under a reduced pressure, and the thus obtained material was separated and purified by a silica gel column chromatography to obtain 300 mg (0.86 mmol, 96% in yield) of the title compound.

$^1$H-NMR (CDCl$_3$): δ 1.51–1.65 (4H, m), 1.86–1.96 (2H, m), 2.64 (1H, tt, J=3.7 Hz, 11.4 Hz), 2.81–2.90 (6H, m), 3.78 (2H, s), 5.14 (2H, s), 6.99–7.03 (1H, m), 7.07–7.13 (3H, m), 7.28–7.39 (5H, m); MW 350.46 ($C_{22}H_{26}N_2O_2$); Mass spectrum TSP m/z 351 (M+H)$^+$.

Synthesis Example 44d 2-Piperidin-4-yl-1,2,3,4-tetrahydro-isoquinoline Dihydrobromide 4-(3,4-Dihydro-1H-isoquinolin-2-yl)piperidine-1-carboxylic acid benzyl ester (290 mg, 0.83 mmol) was mixed with 25% hydrobromic acid acetic acid solution (3 ml) and stirred at room temperature for 2 hours. The reaction solution was mixed with toluene, the solvent was removed by evaporation under a reduced pressure, and the thus precipitated crystals were washed with a small amount of cold toluene and collected by filtration to obtain 150 mg (0.40 mmol, 48% in yield) of the title compound. MW 378.15 ($C_{14}H_{22}Br_2N_2$); Mass spectrum EI-Ms m/z 216 (M–2HBr)$^+$.

Synthesis Example 45d (the Inventive Compound) 2a-(4-(4-(1,2,3,4-Tetrahydro-isoquinolin-2-yl)piperidin-1-yl)-butyl)-2a,3,4,5-tetrahydro-1H-benz[cd]indol-2-one This was synthesized by the same method of Synthesis Example 7d, except that 2-piperidin-4-yl-1,2,3,4-tetrahydro-isoquinoline dihydrobromide was used instead of 1-(1-indanyl)piperazine hydrochloride (yield, 98%).

$^1$H-NMR (CDCl$_3$): δ 1.00–1.14 (1H, m), 1.24–1.50 (2H, m), 1.54–2.00 (12H, m), 2.05–2.18 (2H, m), 2.18–2.33 (1H, m), 2.41–2.51 (1H, m), 2.60–2.70 (1H, m), 2.79–2.91 (5H, m), 2.91–3.00 (2H, m), 3.76 (2H, s), 6.66 (1H, d, J=7.8 Hz), 6.81 (1H, d, J=7.8 Hz), 6.99–7.01 (1H, m), 7.08–7.13 (4H, m), 7.19 (1H, br s); MW 443.64 ($C_{29}H_{37}N_3O$); Mass spectrum EI-MS m/z 443 (M)$^+$.

By dissolving the thus obtained free compound in hydrochloric acid-saturated methanol, its hydrochloride was obtained. MW 516.56 ($C_{23}H_{39}Cl_2N_3O$); Mass spectrum EI-MS m/z 443 (M–2HCl)$^+$.

Synthesis Example 46d 1-Hydroxy-1-pyridin-4-yl-indane

4-Bromopyridine hydrochloride (1.9 g, 10 mmol) was dried and then suspended in diethyl ether (30 ml), and the suspension was mixed with n-butyl lithium hexane solution (1.6 M, 12 ml, 19 mmol) at −60° C. and stirred for 3 hours. The reaction solution was mixed with 1-indanone (2.0 g, 15 mmol) and then the reaction solution was stirred for 18 hours while gradually returning to room temperature. Ethyl acetate (50 ml) and water (50 ml) were added to the reaction solution to extract the reaction product, and the ethyl acetate layer was washed with water and then dried with anhydrous sodium sulfate. The solvent was removed by evaporation from the extract under a reduced pressure, and the thus obtained material was separated and purified by a silica gel column chromatography to obtain 420 mg (2.0 mmol, 20% in yield) of the title compound.

$^1$H-NMR (CDCl$_3$): δ 2.49 (2H, t), 2.64 (1H, br s), 2.95–3.06 (1H, m), 3.17–3.29 (1H, m), 7.04 (1H, d), 7.23 (1H, t), 7.32 (4H, m), 8.51 (2H, dd); MW 211.26 ($C_{14}H_{13}NO$); Mass spectrum EI-MS m/z 211 (M)$^+$.

Synthesis Example 47d 4-Indan-1-yl-piperidine Monohydrochloride

Ethanol (20 ml), concentrated hydrochloric acid (0.5 ml) and platinum oxide (50 mg) were added to 1-hydroxy-1-pyridin-4-yl-indane (540 mg, 2.6 mmol), and catalytic reduction was carried out at ordinary temperature under ordinary pressure to obtain 420 mg (2.1 mmol, 62% in yield) of the title compound as crystals.

In this connection, the hydrochloride was converted into free base in the usual way and then used in the instrumental analyses.

$^1$H-NMR (CDCl$_3$): δ 1.13–1.39 (3H, m), 1.49 (1H, dt), 1.71 (1H, dt), 1.80 (1H, m), 1.94 (1H, m), 2.11 (1H, m), 2.53 (1H, dt), 2.57 (1H, dt), 3.05–3.07 (4H, m), 7.13–7.23 (4H, m); MW 201.31 ($C_{14}H_{19}N$); Mass spectrum EI-MS m/z 201 (M)$^+$.

Synthesis Example 48d (the Inventive Compound) 2a-(4-(4-Indan-1-yl-piperidin-1-yl)-butyl)-2a,3,4,5-tetrahydro-1H-benz[cd]indol-2-one This was synthesized by the same method of Synthesis Example 7d, except that 4-indan-1-yl-piperidine monohydrochloride was used instead of 1-(1-indanyl)piperazine hydrochloride (yield, 54%).

$^1$H-NMR (CDCl$_3$): δ 0.98–1.11 (1H, m), 1.22–1.97 (15H, m), 2.02–2.17 (3H, m), 2.17–2.31 (2H, m), 2.58–2.68 (1H, m), 2.75–3.00 (5H, m), 3.03–3.11 (1H, m), 6.65 (1H, d, J=7.6 Hz), 6.80 (1H, d, J=7.8 Hz), 7.08–7.21 (5H, m), 7.29 (1H, br s); MW 428.62 ($C_{29}H_{36}N_2O$); Mass spectrum EI-MS m/z 428 (M)$^+$.

By dissolving the thus obtained free compound in hydrochloric acid-saturated methanol, its hydrochloride was obtained. MW 465.08 ($C_{29}H_{37}ClN_2O$); Mass spectrum EI-MS m/z 428 (M–HCl)$^+$.

Synthesis Example 1e 1-t-Butoxycarbonyl-4-(1-phenyl-ethyl)-piperazine

This was synthesized by the same method of Synthesis Example 23d, except that 1-bromoethyl-benzene was used instead of 9-bromo-6,7,8,9-tetrahydrobenzocyclohepten-5-one (yield, 99%).

$^1$H-NMR (CDCl$_3$): δ 1.36 (3H, d, J=6.8 Hz), 1.43 (9H, s), 2.30–2.42 (4H, m), 3.34–3.41 (5H, m), 7.21–7.37 (5H, m); MW 290.41 ($C_{17}H_{26}N_{2O2}$); Mass spectrum EI-MS m/z 290 (M)$^+$.

Synthesis Example 2e (the Inventive Compound) 2a-(4-(4-(1-Phenyl-ethyl)-piperazin-1-yl)butyl)-2a,3,4,5-tetrahydro-1H-benz[cd]indol-2-one This was synthesized by the same method of Synthesis Example 21d, except that 1-t-butoxycarbonyl-4-(1-phenyl-ethyl)piperazine was used instead of 1-t-butoxycarbonyl-4-(6,7,8,9-tetrahydro-5H-benzocyclohepten-5-yl)piperazine (yield, 27%).

$^1$H-NMR (CDCl$_3$): δ 0.97–1.08 (1H, m), 1.22–1.43 (7H, m), 1.57–1.89 (6H, m), 2.04–2.68 (11H, m), 2.76–2.86 (1H, m), 6.64 (1H, d, J=7.8 Hz), 6.79 (1H, d, J=7.8 Hz), 7.10 (1H, dd), 7.19–7.31 (9H, m) MW 417.60 ($C_{27}H_{35}N_3O$); Mass spectrum EI-MS m/z 417 (M)$^+$.

By dissolving the thus obtained free compound in hydrochloric acid-saturated methanol, its hydrochloride was obtained. MW 490.51 ($C_{27}H_{37}Cl_2N_3O$); Mass spectrum EI-MS m/z 417 (M–2HCl)$^+$.

Synthesis Example 3e (the Inventive Compound) 2a-(4-(4-(4-Chloro-phenyl)-phenyl-methyl)-piperazin-1-yl)butyl)-2a,3,4,5-tetrahydro-1H-benz[cd]indol-2-one This was synthesized by the same method of Synthesis Example 7d, except that; 1-(4-chloro-phenyl)-phenylmethyl)-piperazine was used instead of 1-indanylpiperazine hydrochloride (yield, 86%).

$^1$H-NMR (CDCl$_3$): δ 1.00–1.43 (8H, m), 1.72–1.89 (2H, m), 2.04–2.89 (12H, m), 4.17 (1H, s), 6.64 (1H, d, J=7.6 Hz), 6.79 (1H, d, J=8.0 Hz), 7.10 (1H, dd), 7.14–7.37 (10H, m); MW 514.11 (C$_{32}$H$_{36}$ClN$_3$O); Mass spectrum EI-MS m/z 513:515=3:1 (M)$^+$.

By dissolving the thus obtained free compound in hydrochloric acid-saturated methanol, its hydrochloride was obtained. MW 587.03 (C$_{32}$H$_{38}$Cl$_3$N$_3$O); Mass spectrum EI-MS m/z 513:515=3:1 (M−2HCl)$^+$.

Synthesis Example 4e (the Inventive Compound) 2a-(4-(4-Benzyl-piperidin-1-yl)butyl)-2a,3,4,5-tetrahydro-1H-benz[cd]indol-2-one 2a-(4-Bromobutyl)-2a,3,4,5-tetrahydro-1H-benz[cd]indol-2-one (190 mg, 0.62 mmol), 4-benzyl-piperidine (110 mg, 0.65 mmol) and potassium carbonate (120 mg, 0.88 mmol) were stirred overnight at 60° C. in anhydrous N,N-dimethylformamide (2 ml). The solvent was removed by evaporation under a reduced pressure, and the residue was mixed with ethyl acetate and water. The reaction product was extracted with ethyl acetate, washed with saturated brine and dried with anhydrous sodium sulfate, the solvent was removed by evaporation under a reduced pressure, and then the thus obtained material was separated and purified by a silica gel column chromatography to obtain 210 mg (1.1 mmol, 85% in yield) of the title compound.

$^1$H-NMR (CDCl$_3$): δ 0.99–1.11 (1H, m), 1.21–1.65 (9H, m), 1.72–1.91 (2H, m), 2.02–2.31 (2H, m), 2.51 (2H, d, J=6.6 Hz), 2.59–2.69 (1H, m) 2.78–2.94 (3H, m), 6.65 (1H, d, J=7.4 Hz), 6.79 (1H, d, J=7.8 Hz), 7.08–7.30 (6H, m), 7.34 (1H, br s); MW 402.58 (C$_{27}$H$_{34}$N$_2$O); Mass spectrum EI-MS m/z 402 (M)$^+$.

By dissolving the thus obtained free compound in hydrochloric acid-saturated methanol, its hydrochloride was obtained. MW (C$_{27}$H$_{35}$ClN$_2$O) 439.04; Mass spectrum PB m/z 403 (M−HCl+H)$^+$.

Synthesis Example 5e (the Inventive Compound) 2a-(4-(4-Benzyl-piperazin-1-yl)butyl)-2a,3,4,5-tetrahydro-1H-benz[cd]indol-2-one This was synthesized by the same method of Synthesis Example 7d, except that 1-benzyl-piperazine was used instead of 1-indanylpiperazine hydrochloride (yield, 99%).

$^1$H-NMR (CDCl$_3$): δ 0.99–1.10 (1H, m), 1.22–1.48 (3H, m), 1.72–1.89 (3H, m), 2.05–2.18 (2H, m), 2.18–2.30 (2H, m), 2.57–2.59 (1H, m), 2.68–2.78 (1H, m), 6.65 (1H, d, J=7.8 Hz), 6.79 (1H, d, J=7.8 Hz), 7.10 (1H, dd), 7.22–7.32 (5H, m), 7.41 (1H, br s); MW 403.5 (C$_{26}$H$_{33}$N$_3$O); Mass spectrum EI-MS m/z 403 (M)$^+$.

By dissolving the thus obtained free compound in hydrochloric acid-saturated methanol, its hydrochloride was obtained. MW (C$_{26}$H$_{35}$Cl$_2$N$_3$O) 476.49; Mass spectrum EI-MS m/z 403 (M−2HCl)$^+$.

Synthesis Example 6e 2-(4-Benzyl-piperazin-1-yl)-2-methyl-propionitrile

Ice (about 8 g) was added to benzylpiperazine (3.5 g, 20 mmol) and stirred, to which were subsequently added dropwise concentrated hydrochloric acid (3.4 ml, 40 mmol), acetone (1.2 g, 20 mmol) and potassium cyanide aqueous solution (7 M, 3 ml, 21 mmol) in that order, and the mixture was stirred at room temperature for 1 hour. Crystals obtained by filtering the reaction solution were dissolved in chloroform, washed with sodium hydroxide aqueous solution and saturated brined and then dried with anhydrous sodium sulfate. The solvent was removed by evaporation under a reduced pressure, and the thus obtained material was separated and purified by a silica gel column chromatography to obtain 1.3 g (5.4 mmol, 27% in yield) of the title compound.

$^1$H-NMR (CDCl$_3$): δ 1.49 (6H, s), 2.52 (4H, br s), 2.68 (4H, br s), 3.51 (2H, s), 7.22–7.33 (5H, m); MW 243.35 (C$_{15}$H$_{21}$N$_3$); Mass spectrum FAB m/z 244 (M+H)$^+$.

Synthesis Example 7e 1-Benzyl-4-(1-methyl-1-phenyl-ethyl)-piperazine

In an atmosphere of argon and at room temperature, 2-(4-benzyl-piperazin-1-yl)-2-methyl-propionitrile (820 mg, 3.4 mmol) dissolved in diethyl ether (1.2 ml) and benzene (2.5 ml) was added dropwise to phenylmagnesium bromide ether solution (3.0 M, 2.0 ml, 6.0 mmol), and the mixture after completion of the dropwise addition was stirred for 3.5 hours. The reaction solution was mixed with 10% ammonium chloride aqueous solution (18 ml) and separated into water layer and organic layer. The reaction product was extracted from the organic layer with dilute hydrochloric acid, and then the water layer was neutralized with aqueous ammonia and the reaction product was again extracted with ethyl acetate. The ethyl acetate layer was washed with water and saturated brine and dried with anhydrous magnesium sulfate, the solvent was removed by evaporation under a reduced pressure, and then the thus obtained material was separated and purified by a silica gel column chromatography to obtain 300 mg (1.0 mmol, 30% in yield) of the title compound.

$^1$H-NMR (CDCl$_3$): δ 1.33 (6H, s), 2.44–2.50 (8H, m), 3.49 (2H, s), 7.16–7.30 (8H, m), 7.51–7.53 (2H, m); MW 294.44 (C$_{20}$H$_{26}$N$_2$); Mass spectrum EI-MS m/z 294 (M)$^+$.

Synthesis Example 8e (the Inventive Compound) 2a-(4-(4-(1-Methyl-1-phenyl-ethyl)-piperazin-1-yl)-butyl)-2a 3,4,5-tetrahydro-1H-benz[cd]indol-2-one 1-Benzyl-4-(1-methyl-1-phenyl-ethyl)-piperazine (290 mg, 1.0 mmol) was dissolved in ethanol (3 ml), and the solution was mixed with 10% palladium-carbon (60 mg) and stirred at room temperature for 15 hours in an atmosphere of hydrogen. The catalyst was removed by filtering the reaction solution, and the solvent was removed by evaporation under a reduced pressure to obtain crude 4-(1-methyl-1-phenyl-ethyl)-piperazine. The thus obtained crude 4-(1-methyl-1-phenyl-ethyl)-piperazine, 2a-(4-bromobutyl)-2a,3,4,5-tetrahydro-1H-benz[cd]indol-2-one (310 mg, 1.0 mmol) and potassium carbonate (210 mg, 1.5 mmol) were stirred at room temperature for 14 hours in anhydrous N,N-dimethylformamide (3 ml). The reaction solution was mixed with ethyl acetate and washed with water and saturated brine, the solvent was removed by evaporation under a reduced pressure and then the thus obtained residue was dissolved in dichloromethane. The dichloromethane solution was washed with water and saturated brine and dried with anhydrous sodium sulfate. The solvent was removed by evaporation from the organic layer under a reduced pressure and the thus obtained material was separated and purified by a silica gel column chromatography to obtain 33 mg (0.076 mmol, 7.7% in yield) of the title compound.

$^1$H-NMR (CDCl$_3$): δ 0.97–1.13 (1H, m), 1.21–1.49 (10H, m), 1.72–1.89 (3H, m), 2.04–2.18 (2H, m), 2.20–2.32 (2H, m), 2.32–2.57 (8H, m), 2.59–2.68 (1H, m), 2.78–2.88 (1H, m), 6.67 (1H, d, J=7.8 Hz), 6.79 (1H, d, J=7.6 Hz), 7.10 (1H, dd), 7.19 (1H, t, J=7.3 Hz), 7.28 (2H, dd, J=7.3 Hz), 7.50 (2H, d), 7.80 (1H, br s); MW 431.62 ($C_{28}H_{37}N_3O$); Mass spectrum EI-MS m/z 431 (M)$^+$.

Test Example 1 Binding Affinity for 5-HT$_7$ Rector

Cultured cells capable of expressing human serotonin 5-HT$_7$ receptor subtype were harvested in an assay buffer solution (50 mM Tris-HCl containing 10 mM MgCl$_2$ and 0.5 mM EDTA, pH 7.4) and homogenized with a Potter tripe homogenizer, and then the membrane fraction was centrifuged for 20 minutes at 39,000 g and at 4° C. The thus obtained pellet was re-suspended in 1 ml, per cells per one culture dish of 10 cm in diameter, of the assay buffer solution and homogenized again.

The binding test was carried out using 1 nM in final concentration of [$^3$H]-5CT (carboxamide tryptamine) and from 1 to 1,000 nM of each substance to be tested (the compound (1) of the invention among Synthesis Examples), and adjusting the final assay volume to 300 μl by adding 100 μl of the membrane fraction suspension and then incubating the reaction system at 37° C. for 30 minutes. The incubation was terminated by quickly filtering on a GF/B filter, subsequently carrying out washing with 6 ml of cold 50 mM Tris-HCl (pH 7.4). The radioactivity was measured using a liquid scintillation counter. Non-specific binding was determined by 10 μM metergoline, and the specific binding was calculated based on the difference therefrom. The IC$_{50}$ value was calculated from the inhibition curve of each compound, and the binding inhibition constant Ki was calculated from the value.

It was confirmed by this binding test that most of the compounds of the invention have a Ki value of 0.1 μM or less.

Test Example 2 Binding Affinity for 5-HT$_2$ Rector

Rat cerebral cortex was homogenized in 10 volumes of 0.32 M sucrose solution and centrifuged for 10 minutes at 900×g, and the resulting supernatant fluid was again centrifuged for 20 minutes at 11,500×g. The thus obtained precipitate was re-suspended in 50 mM Tris-HCl (pH 7.4) buffer and centrifuged for 20 minutes at 39,900×g, and the thus obtained precipitate was used as P2 fraction.

The P2 fraction was incubated at 37° C. for 15 minutes in 50 mM Tris-HCl (pH 7.4) buffer containing 1 nM of [$^3$H]ketanserin and each of the compounds of the invention and then filtered after the reaction using Whatman GF/B glass filter. The radioactivity on the filter was measured using a liquid scintillation counter. Non-specific binding was determined by 10 μM ketanserin, and the specific binding was calculated based on the difference therefrom. The IC$_{50}$ value was calculated from the inhibition curve of each compound, and the binding inhibition constant Ki was calculated from the value.

The Ki value of 5-HT$_2$, the Ki value of 5-HT$_7$ obtained in Test Example 1 and their ratio are shown in Table 1. As is evident from Table 1, compounds of the invention show their affinity for 5-HT$_7$ receptor more selectively.

TABLE 1

| (the inventive compound) | Ki (nM) of 5-HT$_2$ | Ki (nM) of 5-HT$_7$ | 5-HT$_2$/5-HT$_7$ |
|---|---|---|---|
| Compd. of Syn. Ex. 1a | 227 | 7 | 33 |
| Compd. of Syn. Ex. 17a | 807 | 9 | 90 |
| Compd. of Syn. Ex. 21a | 524 | 13 | 40 |
| Compd. of Syn. Ex. 1b | 151 | 9 | 17 |
| Compd. of Syn. Ex. 10b | >1000 | 7 | >143 |
| Compd. of Syn. Ex. 13b | 385 | 8 | 48 |
| Compd. of Syn. Ex. 14c | >1000 | 1.9 | >530 |
| Compd. of Syn. Ex. 17c | >1000 | 0.9 | >1100 |
| Compd. of Syn. Ex. 10d | >1000 | 9.8 | >100 |
| Compd. of Syn. Ex. 37d | 882 | 8.8 | 100 |
| Compd. of Syn. Ex. 2e | 456 | 30 | 15 |

Industrial Applicability:

The compound of the invention strongly inhibits [$^3$H]-5CT which binds to human serotonin 5-HT$_7$ receptor subtype expressed in a clonal cell line. In consequence, the compound (1) of the invention and pharmacologically acceptable salts thereof are useful as medicaments for the prevention or treatment of various diseases which are considered to be induced by the abnormality of central and peripheral serotonin controlling functions, such as mental diseases (manic-depressive psychosis, anxiety, schizophrenia, epilepsy, sleep disorders, biological rhythm disorders, migraine and the like), cardiovascular diseases (hypertension and the like) and gastrointestinal disorders.

What is claimed is:

1. A compound represented by formula (1):

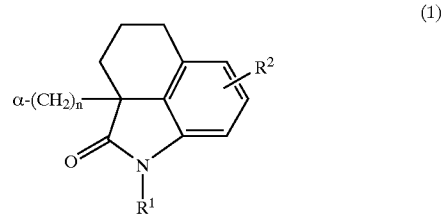

(1)

wherein $R^1$ represents a hydrogen atom, a lower alkyl group or an aralkyl group; $R^2$ represents a hydrogen atom, a halogen atom, a lower alkyl group, a hydroxy group, an alkoxy group, an acyl group, an acyloxy group, an alkoxycarbamoyl group, a nitro group, an amino group, a substituted amino group, a carbamoyl group or an alkylcarbamoyl group; n is an integer of from 2 to 6; and α represents the following formula (a), (b), (c), or (d):

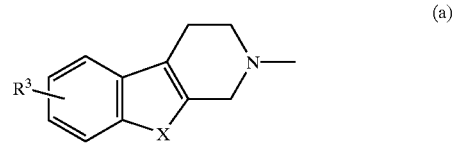

(a)

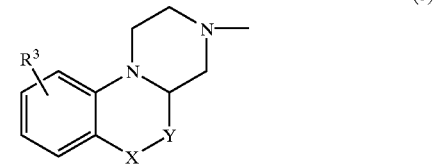

(b)

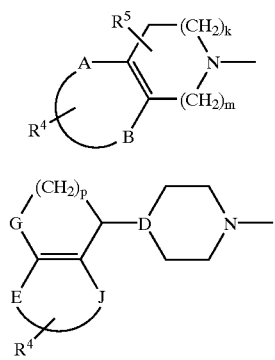

wherein
  in formulae (a) and (b), $R^3$ represents a hydrogen atom, a halogen atom, a lower alkyl group, a hydroxy group or an alkoxy group, X represents $NR^{10}$, $NCONR^{11}R^{12}$, S, SO, $SO_2$ or O, $R^{10}$ represents a hydrogen atom, a lower alkyl group, an alkenyl group, an oxoalkyl group, an aralkyl group, a cyanoalkyl group, a hydroxyalkyl group, an alkoxyalkyl group, an aminoalkyl group, a substituted aminoalkyl group, an alkoxycarbonylalkyl group, a carbamoylalkyl group, an alkylcarbamoylalkyl group, an acyl group or an alkoxycarbonyl, $R^{11}$ and $R^{12}$ independently represent a hydrogen atom or a lower alkyl group, and Y represents a methylene group or a carbonyl group,
  in formula (c), $R^4$ represents a hydrogen atom, a halogen atom, a lower alkyl group, a hydroxy group, a cyano group, a trihalomethyl group, an alkoxy group, an alkylthio group, an alkylsulfinyl group, an alkylsulfonyl group, an alkoxycarbonyl, a sulfamoyl group, an amino group, a substituted amino group, a carbamoyl group, an alkylcarbamoyl group, an acyl group or a carboxy group, $R^5$ represents a hydrogen atom, a lower alkyl group, a hydroxy group, an alkoxy group, an acyl group, a phenyl group or a substituted phenyl group, k is 0 or an integer of from 1 to 3, m is 0 or an integer of from 1 to 3, and each of A and B represents a group which forms a benzene ring, a thiophene ring, a furan ring, an imidazole ring or a pyrazole ring via a double bond, with the proviso that k+m is an integer of from 1 to 3, and
  in formula (d), $R^4$ is as defined in the foregoing, G represents $CH_2$, S, O or C=O, D represents CH or N, p is an integer of from 1 to 3, and each of E and J represents a group which forms a benzene ring or a pyridine ring via a double bond or a pharmaceutically acceptable salt thereof.

2. A compound according to claim 1, which is represented by formula (1a):

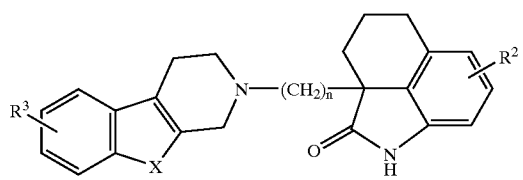

wherein $R^2$, $R^3$, X and n are as defined in the foregoing, or a pharmaceutically acceptable salt thereof.

3. A compound according to claim 2, which is represented by formula (1a-1):

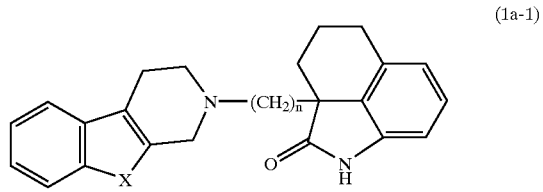

wherein X and n are as defined in the foregoing, or a pharmaceutically acceptable salt thereof.

4. A compound according to claim 1, which is represented by formula (1b):

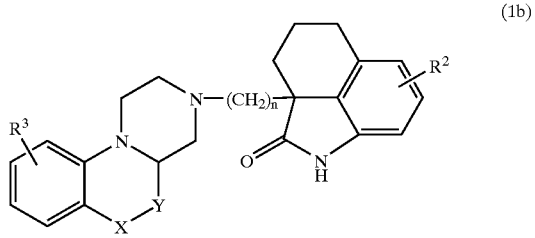

wherein $R^2$, $R^3$, X, Y and n are as defined in the foregoing, or a pharmaceutically acceptable salt thereof.

5. A compound according to claim 4, which is represented by formula (1b-1):

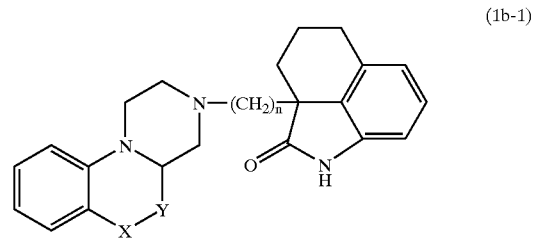

wherein X, Y and are as defined in the foregoing, or a pharmaceutically acceptable salt thereof.

6. A compound according to claim 1, which is represented by formula (1c):

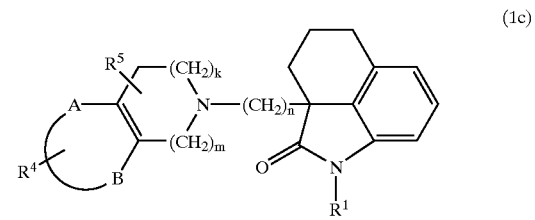

wherein $R^1$, $R^4$, $R^5$, A, B, k, m and n are as defined in the foregoing, or a pharmaceutically acceptable salt thereof.

7. The compound or a pharmaceutically acceptable salt thereof according to claim 6, wherein k+m is 2.

8. The compound or a pharmaceutically acceptable salt thereof according to claim 6 or 7, wherein n is 4.

9. A compound according to claim 1, which is represented by formula (1d):

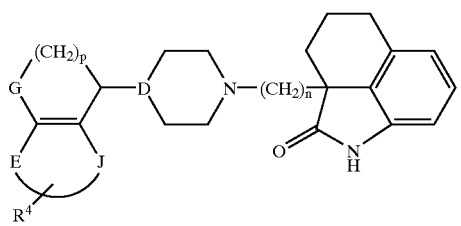

wherein R⁴, G, D, E, J, p and n are as defined in the foregoing, or a pharmaceutically acceptable salt thereof.

10. A compound represented by formula (1e):

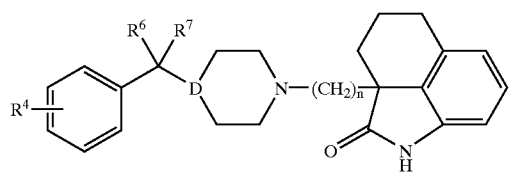

wherein $R^4$ represents a hydrogen atom, a halogen atom, a lower alkyl group, a hydroxy group, a cyano group, a trihalomethyl group, an alkoxy group, an alkylthio group, an alkylsulfinyl group, an alkylsulfonyl group, an amino group, a substituted amino group, a carbamoyl group, an alkylcarbamoyl group, an acetyl group, or a carboxy group, $R^6$ and $R^7$ independently represent a hydrogen atom, a lower alkyl group, a hydroxy group, an alkoxy group, an acetyl group, a phenyl group or a substituted phenyl group, D represents CH or N, and n is an integer of 2 to 6, or a pharmaceutically acceptable salt thereof.

11. A pharmaceutical composition which comprises any one of the compounds of claims 1 to 9 or a pharmaceutically acceptable salt thereof.

12. A pharmaceutical composition which comprises a compound of claim 10 or a pharmaceutically acceptable salt thereof.

* * * * *